United States Patent
Hosokawa et al.

(10) Patent No.: US 8,022,253 B2
(45) Date of Patent: Sep. 20, 2011

(54) AROMATIC AMINE DERIVATIVE AND ORGANIC ELECTROLUMINESCENCE DEVICE USING THE SAME

(75) Inventors: Chishio Hosokawa, Chiba (JP); Yoriyuki Takashima, Chiba (JP); Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 759 days.

(21) Appl. No.: 11/736,884

(22) Filed: Apr. 18, 2007

(65) Prior Publication Data

US 2008/0004445 A1    Jan. 3, 2008

(30) Foreign Application Priority Data

Apr. 18, 2006    (JP) .................................. 2006-114904

(51) Int. Cl.
*C07C 211/00* (2006.01)
*C07C 13/48* (2006.01)
*C07C 13/465* (2006.01)
*C07C 15/20* (2006.01)
*H01J 1/62* (2006.01)
*H01J 63/04* (2006.01)

(52) U.S. Cl. ........... 564/431; 564/434; 313/503; 585/26
(58) Field of Classification Search .................. None
See application file for complete search history.

(56) References Cited

U.S. PATENT DOCUMENTS

| 7,029,764 B2 | 4/2006 | Hsu et al. |
| 2004/0137270 A1 | 7/2004 | Seo et al. |
| 2004/0146742 A1 | 7/2004 | Hsu et al. |
| 2004/0209118 A1* | 10/2004 | Seo et al. ...................... 428/690 |
| 2005/0067951 A1 | 3/2005 | Richter et al. |
| 2006/0093856 A1 | 5/2006 | Helber et al. |
| 2007/0114917 A1 | 5/2007 | Funahashi et al. |

FOREIGN PATENT DOCUMENTS

| DE | 102 03 328 A1 | 8/2003 |
| EP | 1 437 395 A2 | 7/2004 |
| JP | 62-018565 | 1/1987 |
| JP | 10-302960 | 11/1998 |
| JP | 11-260551 | 9/1999 |
| JP | 2003-201472 | 7/2003 |
| JP | 2004-124106 | 4/2004 |

(Continued)

OTHER PUBLICATIONS

JP2004196716 Machine Translation 83 pages.*

(Continued)

*Primary Examiner* — Daniel Sullivan
*Assistant Examiner* — Clinton Brooks
(74) *Attorney, Agent, or Firm* — Oblon, Spivak, McClelland, Maier & Neustadt, L.L.P.

(57) ABSTRACT

To attain an organic electroluminescence device having a long lifetime and high luminous efficiency, and is capable of emitting blue light having a high color purity, and an aromatic amine derivative for realizing the device, the present invention provides an aromatic amine derivative having a specific structure, and an organic electroluminescence device including an organic thin film layer composed of one or more layers including at least a light emitting layer and interposed between a cathode and an anode, in which at least one layer of the organic thin film layer contains the aromatic amine derivative alone or as a component of a mixture.

15 Claims, 2 Drawing Sheets

FOREIGN PATENT DOCUMENTS

| | | |
|---|---|---|
| JP | 2004-196716 | 7/2004 |
| JP | 2004-204238 | 7/2004 |
| JP | 2005-082701 | 3/2005 |
| JP | 2005-516059 | 6/2005 |
| JP | 2006-251350 | 9/2006 |
| WO | WO 03/064373 A1 | 8/2003 |
| WO | WO 2006/049860 A1 | 5/2006 |

OTHER PUBLICATIONS

Supplementary European Search Report issued Jan. 21, 2011, in EP 07 74 1809.

Shin-ichiro Kato, et al., "Novel 2,1,3-Benzothiadiazole-Based red-Fluorescent Dyes with Enhanced Two-Photo Absorption Cross-Sections", Chem. Eur. J., 2006, 12, 2303-2317. XP-002615530.

* cited by examiner

AROMATIC AMINE DERIVATIVE AND ORGANIC ELECTROLUMINESCENCE DEVICE USING THE SAME

TECHNICAL FIELD

The present invention relates to an aromatic amine derivative and an organic electroluminescence device using the derivative, in particular, an organic electroluminescence device having a long lifetime and high luminous efficiency, and capable of emitting blue light having a high color purity, and an aromatic amine derivative for realizing the device.

BACKGROUND ART

A large number of organic EL devices each using an organic substance have been developed because of their potential to find applications in solid light emission type, inexpensive, large-area, full-color display devices. In general, an EL device is constituted of a light emitting layer and a pair of opposing electrodes between which the layer is interposed. Light emission is the following phenomenon: when an electric field is applied between both the electrodes, an electron is injected from a cathode side and a hole is injected from an anode side, and, furthermore, the electron recombines with the hole in the light emitting layer to produce an excited state, and energy generated upon return of the excited state to a ground state is emitted as light.

A conventional organic EL device has been driven at a voltage higher than the voltage at which an inorganic light emitting diode is driven, and has had emission luminance and luminous efficiency lower than those of the diode. In addition, the properties of the device have deteriorated remarkably, so the device has not been put into practical use. Although a recent organic EL device has been gradually improved, additionally high luminous efficiency and an additionally long lifetime of the device are requested. For example, a technique involving the use of a single monoanthracene compound as an organic light emitting material has been disclosed (Patent Document 1). However, the technique provides a luminance as low as 1,650 cd/m$^2$ at a current density of, for example, 165 mA/cm$^2$, and provides extremely low efficiency, specifically, 1 cd/A, so the technique is not practical. In addition, a technique involving the use of a single bisanthracene compound as an organic light emitting material has been disclosed (Patent Document 2). However, even the technique provides an efficiency as low as about 1 to 3 cd/A, so an improvement for putting the technique into practical use has been demanded. Meanwhile, a long-lifetime organic EL device obtained by adding, for example, styrylamine to a distyryl compound to be used as an organic light emitting material has been proposed (Patent Document 3). However, the device does not have a sufficient lifetime, and the additional improvement of the device has been demanded.

In addition, techniques each involving the use of each of a monoanthracene or bisanthracene compound and a distyryl compound in an organic light emitting medium layer have been disclosed (Patent Document 4). However, in each of those techniques, the conjugate structure of the styryl compound lengthens the wavelength of an emission spectrum, with the result that a color purity is deteriorated. Further, Patent Document 5 discloses a blue light emitting device using a diaminochrysene derivative.

The blue light emitting device is excellent in luminous efficiency. However, the device does not have a sufficient lifetime, and the additional improvement of the device has been demanded.

In addition, furthermore, Patent Document 6 discloses an organic EL device using a tetraarylethene derivative. However, when the tetraarylethene derivative is used in the light emitting layer of the device, a luminescent color becomes a cyan color, so blue light having a high color purity cannot be emitted.

Patent Document 1: JP 11-3782 A
Patent Document 2: JP 8-12600 A
Patent Document 3: WO94/006157 A
Patent Document 4: JP 2001-284050 A
Patent Document 5: WO04/044088 A
Patent Document 6: JP 11-260551 A

DISCLOSURE OF THE INVENTION

Problem to be Solved by the Invention

The present invention has been made with a view to solving the above problems, and an object of the present invention is to provide an organic EL device having a long lifetime and high luminous efficiency, and capable of emitting blue light having a high color purity, and an aromatic amine derivative for realizing the device.

Means for Solving the Problem

The inventors of the present invention have made extensive studies with a view to developing an aromatic amine derivative having the above preferable nature and an organic EL device using the derivative. As a result, the inventors have found that the object can be achieved with the utilization of an aromatic amine derivative having a specific structure represented by any one of the following general formulae (I) to (VIII). The present invention has been completed on the basis of such finding.

That is, provided is an aromatic amine derivative represented by any one of the following general formulae (I) to (VIII):

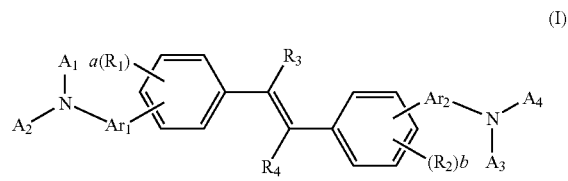

(I)

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$A_1$ to $A_4$ each independently represent a substituted or unsubstituted aryl group having 5 to 50 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond, a substituted or unsubstituted aryl group having 5 to 50 carbon atoms, or a substituted or unsubstituted heterocyclic group having 5 to 50 carbon atoms; and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring, provided that at least one of $A_1$ and $A_2$, and at least one of $A_3$ and $A_4$ each represent a substituted or unsubstituted nitrogen-containing heterocyclic group having 5 to 25 ring atoms;

(II)

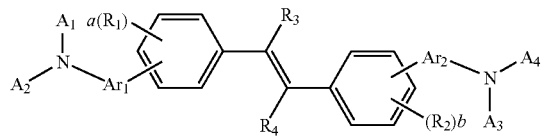

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond, a substituted or unsubstituted aryl group having 5 to 50 carbon atoms, or a substituted or unsubstituted heterocyclic group having 5 to 50 carbon atoms; and $A_1$ to $A_4$ each independently represent a substituted or unsubstituted, saturated or unsaturated aryl group having 10 to 50 carbon atoms;

(III)

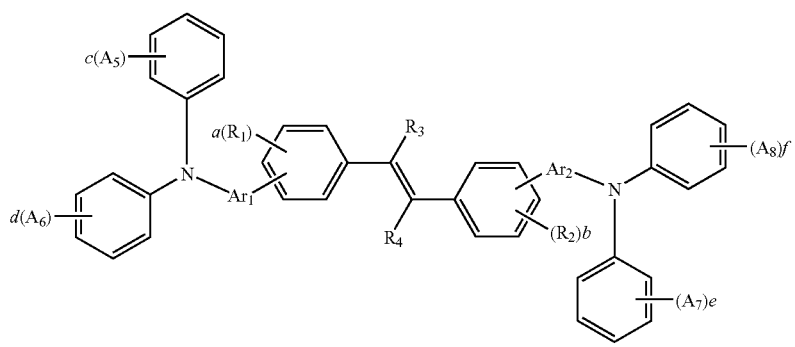

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; and c, d, e, and f each independently represent an integer of 0 to 5, when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of c and d, and at least one of e and f each represent 2 or more;

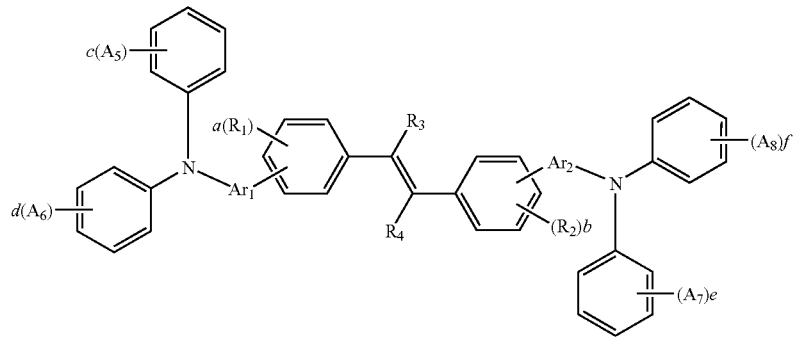

(IV)

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond, a substituted or unsubstituted aryl group having 5 to 50 carbon atoms, or a substituted or unsubstituted heterocyclic group having 5 to 50 carbon atoms;

$A_5$ to $A_8$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond, a substituted or unsubstituted aryl group having 5 to 50 carbon atoms, or a substituted or unsubstituted heterocyclic group having 5 to 50 carbon atoms;

$A_5$ to $A_8$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; and c, d, e, and f each independently represent an integer of 0 to 5, when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of $A_5$ and $A_6$, and at least one of $A_7$ and $A_8$ each represent a substituted or unsubstituted silyl group having 1 to 20 carbon atoms;

alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$Ar_1$ and $Ar_2$ each independently represent a single bond, a substituted or unsubstituted aryl group having 5 to 50 carbon atoms, or a substituted or unsubstituted heterocyclic group having 5 to 50 carbon atoms;

$A_5$ to $A_8$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; and (V)

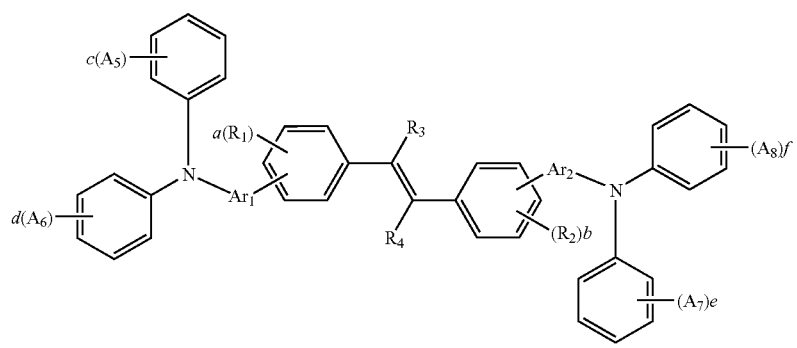

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted c, d, e, and f each independently represent an integer of 0 to 5, when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of $A_5$ and $A_6$, and at least one of $A_7$ and $A_8$ each represent a substituted or unsubstituted cycloalkyl group having 3 to 50 carbon atoms;

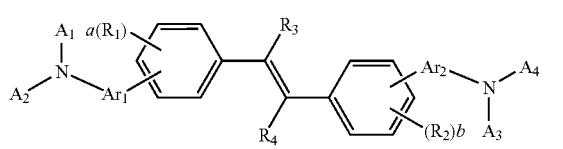

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$A_1$ to $A_4$ each independently represent a substituted or unsubstituted aryl group having 5 to 50 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond, a substituted or unsubstituted aryl group having 5 to 50 carbon atoms, or a substituted or unsubstituted heterocyclic group having 5 to 50 carbon atoms; and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring, provided that $Ar_1$ and $Ar_2$ are different from each other, and a case where both of $Ar_1$ and $Ar_2$ represent a heterocyclic group is excluded;

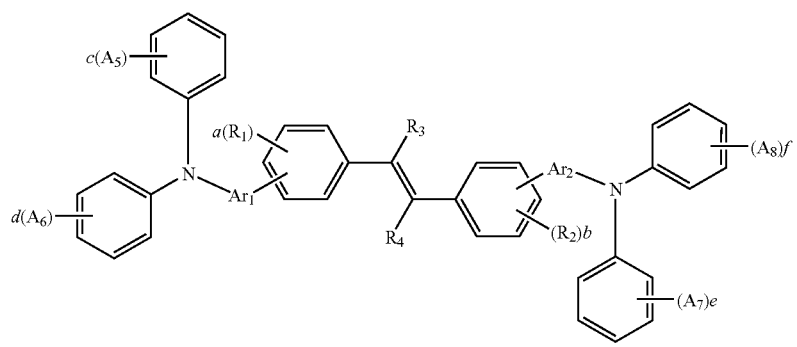

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$A_5$ to $A_8$ each independently represent a substituted or unsubstituted aryl group having 5 to 50 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond; and c, d, e, and f each independently represent an integer of 0 to 5, when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of c and d, and at least one of e and f each represent 2 or more;

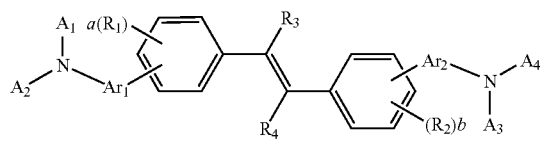

(VIII)

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

a and b each independently represent an integer of 0 to 4, when a represents 2 or more, multiple $R_1$s may be identical to or different from each other, and when b represents 2 or more, multiple $R_2$s may be identical to or different from each other;

$R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms;

$Ar_1$ represents a substituted or unsubstituted aryl group having 5 to 50 carbon atoms, or a substituted or unsubstituted heterocyclic group having 5 to 50 carbon atoms;

$Ar_2$ represents a single bond; and $A_1$ to $A_4$ each independently represent a substituted or unsubstituted, saturated or unsaturated aryl group having 10 to 50 carbon atoms.

In the general formula (I), $R_1$ to $R_4$ each independently represent a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 5 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted silyl group having 1 to 20 carbon atoms, a substituted or unsubstituted heterocyclic group having 5 to 50 ring carbon atoms, or a halogen atom.

a and b each independently represent an integer of 0 to 4, when a or b represents 2 or more, multiple $R_1$s or multiple $R_2$s may be identical to or different from each other, $A_1$ to $A_4$ each independently represent a substituted or unsubstituted aryl group having 5 to 50 ring carbon atoms, or a substituted or unsubstituted heterocyclic group having 5 to 50 ring carbon atoms, $Ar_1$ and $Ar_2$ each independently represent a substituted or unsubstituted arylene group having 5 to 50 ring carbon atoms, or a substituted or unsubstituted divalent heterocyclic group having 5 to 50 ring carbon atoms, and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring.

Further, the present invention provides an organic EL device including an organic thin film layer composed of one or more layers including at least a light emitting layer and interposed between a cathode and an anode, in which at least one layer of the organic thin film layer contains the aromatic amine derivative alone or as a component of a mixture.

Effects of the Invention

An organic EL device using the aromatic amine derivative of the present invention provides emission luminance sufficient for practical use even at a low applied voltage, has high luminous efficiency, hardly deteriorates even after long-term use, and has a long lifetime.

BEST MODE FOR CARRYING OUT THE INVENTION

Figure 1:
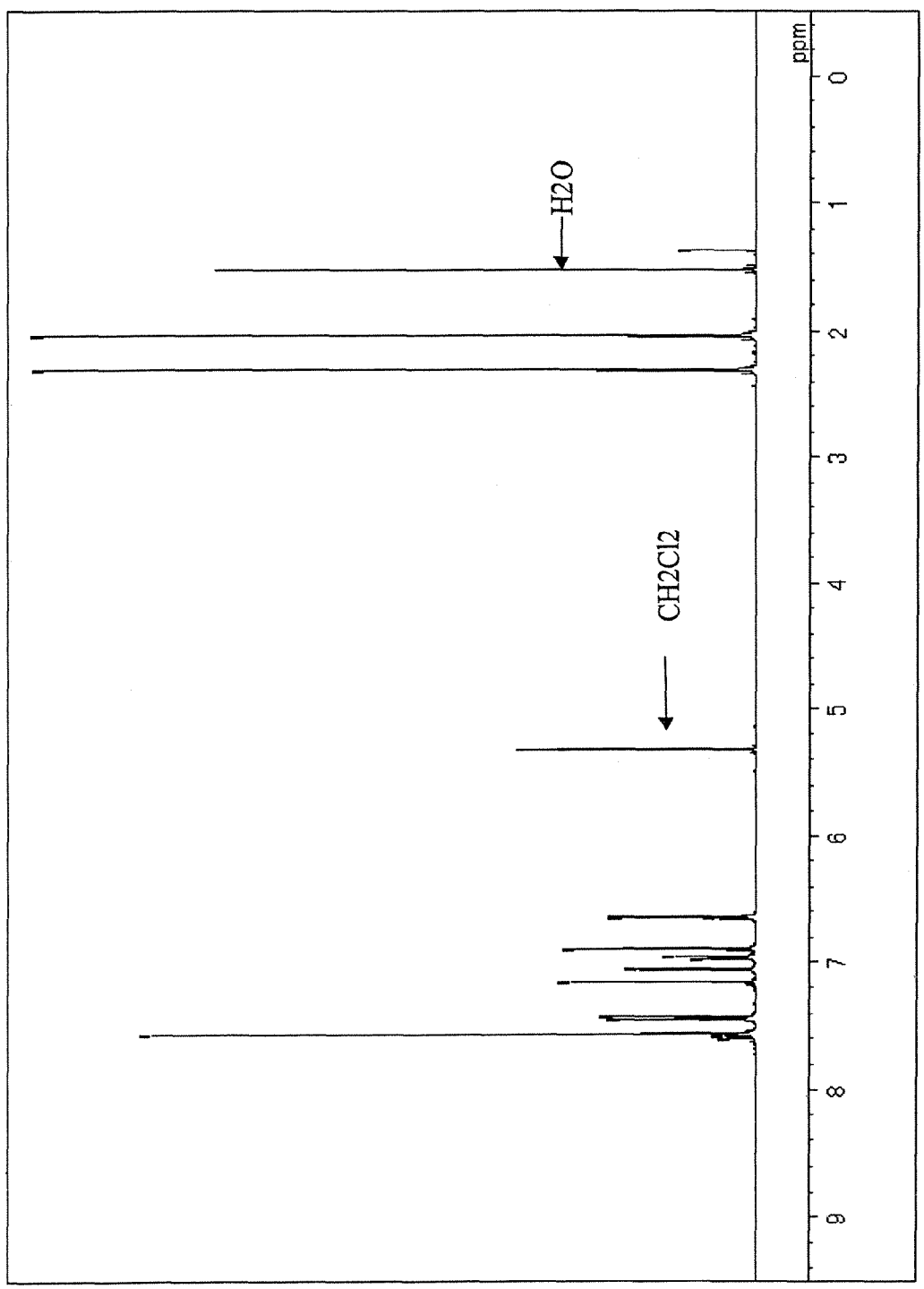
FIG. 1 is a view showing an $^1$H-NMR spectrum of an aromatic amine derivative of the present invention obtained in Synthesis Example 2.

An aromatic amine derivative of the present invention is a compound represented by any one of the following general formulae (I) to (VIII);

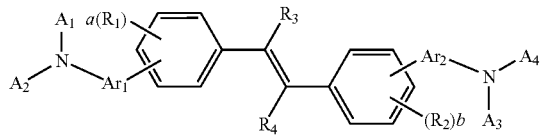

(I)

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $A_1$ to $A_4$ each independently represent a substituted or unsubstituted aryl group having 5 to 50 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond, a substituted or unsubstituted aryl group having 5 to 50 carbon atoms, or a substituted or unsubstituted heterocyclic group having 5 to 50 carbon atoms; and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring, provided that at least one of $A_1$ and $A_2$, and at least one of $A_3$ and $A_4$ each represent a substituted or unsubstituted, nitrogen-containing heterocyclic group having 5 to 25 ring atoms;

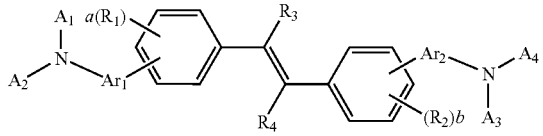

(II)

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond, a substituted or unsubstituted aryl group having 5 to 50 carbon atoms, or a substituted or unsubstituted heterocyclic group having 5 to 50 carbon atoms; and $A_1$ to $A_4$ each independently represent a substituted or unsubstituted, saturated or unsaturated aryl group having 10 to 50 carbon atoms;

(III)

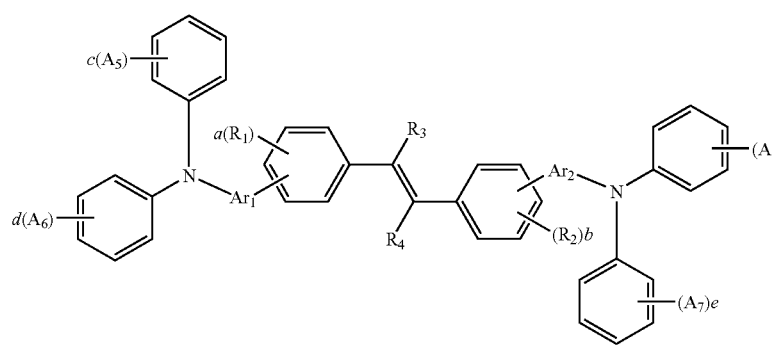

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond, a substituted or unsubstituted aryl group having 5 to 50 carbon atoms, or a substituted or unsubstituted heterocyclic group having 5 to 50 carbon atoms; $A_5$ to $A_8$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; and c, d, e, and f each independently represent an integer of 0 to 5, when any one of c, d, e, and f represents 2 or more, corresponding multiple $A_1$s, $A_2$s, $A_3$s, or $A_4$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of c and d, and at least one of e and f each represent 2 or more;

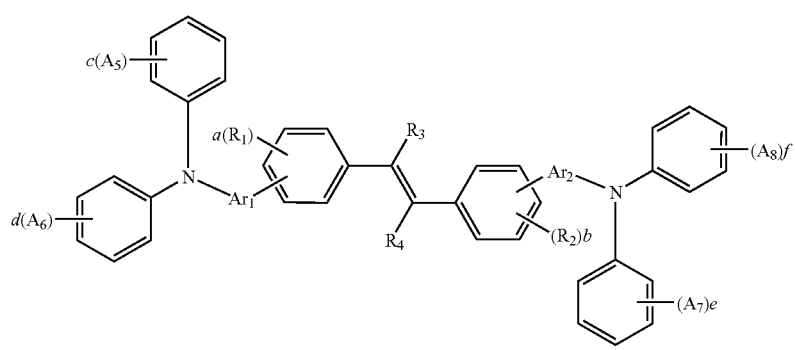

(IV)

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond, a substituted or unsubstituted aryl group having 5 to 50 carbon atoms, or a substituted or unsubstituted heterocyclic group having 5 to 50 carbon atoms; $A_5$ to $A_8$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; and c, d, e, and f each independently represent an integer of 0 to 5, when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of $A_5$ and $A_6$, and at least one of $A_7$ and $A_8$ each represent a substituted or unsubstituted silyl group having 1 to 20 carbon atoms;

substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond, a substituted or unsubstituted aryl group having 5 to 50 carbon atoms, or a substituted or unsubstituted heterocyclic group having 5 to 50 carbon atoms; $A_5$ to $A_8$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino (V)

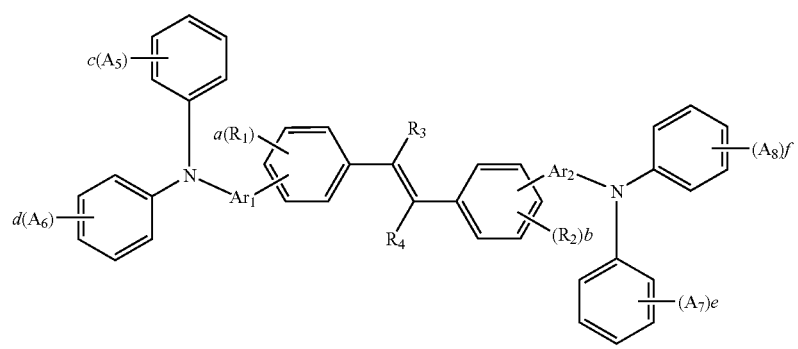

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a group having 1 to 20 carbon atoms, a substituted or unsubstituted silyl group having 1 to 20 carbon atoms, or a substituted or unsubstituted heterocyclic group having 5 to 50 carbon atoms; and c, d, e, and f each independently represent an integer of 0 to 5, when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring, provided that at least one of $A_5$ and $A_6$, and at least one of $A_7$ and $A_8$ each represent a substituted or unsubstituted cycloalkyl group having 3 to 50 carbon atoms;

(VI)

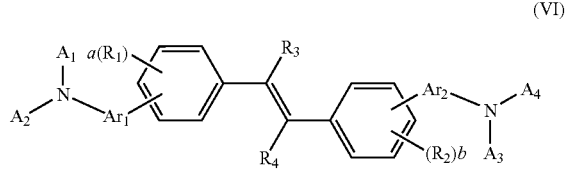

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $A_1$ to $A_4$ each independently represent a substituted or unsubstituted aryl group having 5 to 50 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond, a substituted or unsubstituted aryl group having 5 to 50 carbon atoms, or a substituted or unsubstituted heterocyclic group having 5 to 50 carbon atoms; and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring, provided that $Ar_1$ and $Ar_2$ are different from each other, and a case where both of $Ar_1$ and $Ar_2$ each represent a heterocyclic group is excluded;

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $A_1$ to $A_4$ each independently represent a substituted or unsubstituted aryl group having 5 to 50 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond; and c, d, e, and f each independently represent an integer of 0 to 5, when anyone of c, d, e, and f represents 2 or more, corresponding multiple $A_1$s, $A_2$s, $A_3$s, or $A_4$s may be identical to or different from each other, or may be coupled with each other to form a saturated or unsaturated ring, and $A_1$ and $A_2$, or $A_3$ and $A_4$ may be coupled with each other to form a saturated or unsaturated ring, provided that at least one of c and d, and at least one of e and f each represent 2 or more;

(VII)

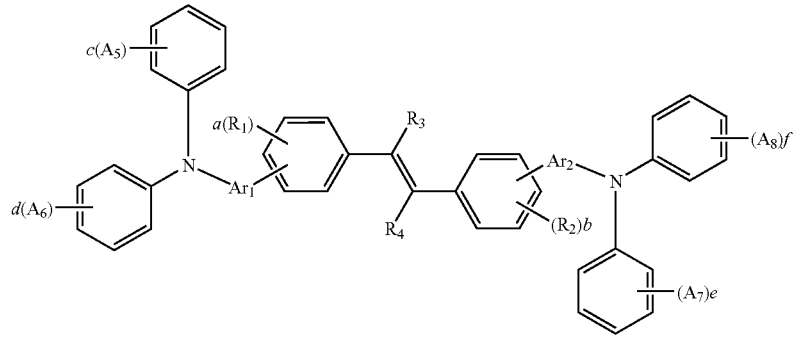

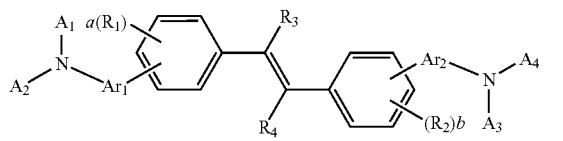

(VIII)

where: $R_1$ and $R_2$ each independently represent a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; a and b each independently represent an integer of 0 to 4, when a represents 2 or more, multiple $R_1$s may be identical to or different from each other, and when b represents 2 or more, multiple $R_2$s may be identical to or different from each other; $R_3$ and $R_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 5 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms; $Ar_1$ represents a substituted or unsubstituted aryl group having 5 to 50 carbon atoms, or a substituted or unsubstituted heterocyclic group having 5 to 50 carbon atoms; $Ar_2$ represents a single bond; and $A_1$ to $A_4$ each independently represent a substituted or unsubstituted, saturated or unsaturated aryl group having 10 to 50 carbon atoms.

Examples of the alkyl group having 1 to 50 carbon atoms represented by each of $R_1$ to $R_4$ include a methyl group, an ethyl group, a propyl group, an isopropyl group, a butyl group, a sec-butyl group, a tert-butyl group, a pentyl group, a hexyl group, a heptyl group, an octyl group, a stearyl group, a 2-phenylisopropyl group, a trichloromethyl group, a trifluoromethyl group, a benzyl group, an α-phenoxybenzyl group, an α,α-dimethylbenzyl group, an α,α-methylphenylbenzyl group, an α,α-ditrifluoromethylbenzyl group, a triphenylmethyl group, and an α-benzyloxybenzyl group.

Examples of the aryl group having 5 to 50 carbon atoms represented by each of $R_1$ to $R_4$ include a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, a terphenyl group, a 3,5-dichlorophenyl group, a naphthyl group, 5-methyl naphthyl group, an anthryl group, and a fluorenyl group.

Examples of the aralkyl group having 1 to 50 carbon atoms represented by each of $R_1$ to $R_4$ include a benzyl group, a 1-phenylethyl group, a 2-phenylethyl group, a 1-phenylisopropyl group, a 2-phenylisopropyl group, a phenyl-t-butyl group, an α-naphtylmethyl group, a 1-α-naphtylethyl group, a 2-α-naphtylethyl group, a 1-α-naphtylisopropyl group, a 2-α-naphtylisopropyl group, a β-naphtylmethyl group, a 1-β-naphtylethyl group, a 2-β-naphtylethyl group, a 1-β-naphtylisopropyl group, a 2-β-naphtylisopropyl group, a 1-pyrolylmethyl group, a 2-(1-pyrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, a m-nitrobenzyl group, an o-nitrobenzyl group, a p-cyanobenzyl group, a m-cyanobenzyl group, an o-cyanobenzyl group, a 1-hydroxy-2-phenylisopropyl group, and a 1-chloro-2-phenylisopropyl group.

Examples of the cycloalkyl group having 5 to 50 carbon atoms represented by each of $R_1$ to $R_4$ include a cyclopropyl group, a cyclobutyl group, a cyclopentyl group, a cyclohexyl group, a cycloheptyl group, a cyclooctyl group, a cyclononyl group, a bicycloheptyl group, a bicyclooctyl group, a tricycloheptyl group, an adamantyl group. Of those, a cyclopentyl group, a cyclohexyl group, a cycloheptyl group, a bicycloheptyl group, a bicyclooctyl group, and an adamantyl group is preferred.

Examples of the alkoxyl group having 1 to 50 carbon atoms represented by each of $R_1$ to $R_4$ include a methoxy group, an ethoxy group, a propoxy group, an isopropoxy group, a butoxy group, an isobutoxy group, a sec-butoxy group, a tert-butoxy group, each kinds of pentyloxy groups, and each of hexyloxy groups.

$R_1$ to $R_4$ each represent a substituted or unsubstituted, a substituted or unsubstituted, a substituted or unsubstituted silyl group having 1 to 20 carbon atoms, or a substituted or unsubstituted heterocyclic group having 5 to 50 carbon atoms.

Examples of the aryloxy group having 5 to 50 carbon atoms represented by each of $R_1$ to $R_4$ include a phenoxy group, a tolyloxy group, and a naphtyloxy group.

Examples of the arylamino group having 5 to 50 carbon atoms represented by each of $R_1$ to $R_4$ include a diphenylamino group, a ditolylamino group, a dinaphthylamino group, and a naphthylphenylamino group.

Examples of the alkylamino group having 1 to 20 carbon atoms represented by each of $R_1$ to $R_4$ include a dimethylamino group, a diethylamino group, and a dihexylamino group.

Examples of the silyl group having 1 to 20 carbon atoms represented by each of $R_1$ to $R_4$ include a silyl group, a trimethylsilyl group, a triethylsilyl group, a tripropylsilyl group, a triphenylsilyl group, butyldimethylsilyl group, propyldimethylsilyl group, vinyldimethylsilyl group, and t-butyldimethylsilyl group.

Examples of the heterocyclic group having 5 to 50 carbon atoms represented by each of $R_1$ to $R_4$ include residual groups of an imidazole, a benzoimidazole, pyrrole, furan, thiophene, benzothiophene, oxadiazoline, indoline, carbazole, pyridine, quinoline, isoquinoline, benzoquinone, pyralozine, imidazolidine, and piperidine.

In each of the general formulae (I) to (VIII), a and b each independently represent an integer of 0 to 4, when a represents 2 or more, multiple $R_1$s may be identical to or different from each other, and when b represents 2 or more, multiple $R_2$s may be identical to or different from each other.

In each of the general formulae (I) to (VIII), $Ar_1$ represents a substituted or unsubstituted aryl group having 5 to 50 carbon atoms, or a substituted or unsubstituted heterocyclic group having 5 to 50 carbon atoms, and specific examples of $Ar_1$ include the same examples as those described for each of $R_1$ to $R_4$.

In each of the general formulae (I) to (VI), $Ar_2$ represents a single bond, a substituted or unsubstituted aryl group having 5 to 50 carbon atoms, or a substituted or unsubstituted heterocyclic group having 5 to 50 carbon atoms, and, in each of the general formulae (VII) and (VIII), $Ar_2$ represents a single bond, and specific examples of $Ar_2$ include the same examples as those described for each of $R_1$ to $R_4$.

In the general formula (I), $A_1$ to $A_4$ each independently represent a substituted or unsubstituted aryl group having 5 to 50 carbon atoms, or a substituted or unsubstituted heterocyclic group having 5 to 50 carbon atoms, specific examples of each of $A_1$ to $A_4$ include the same examples as those described for each of $R_1$ to $R_4$, and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring; provided that at least one of $A_1$ and $A_2$, and at least one of $A_3$ and $A_4$ each represent a substituted or unsubstituted, nitrogen-containing heterocyclic group having 5 to 25 ring atoms.

In the general formula (II), $A_1$ to $A_4$ each independently represent a substituted or unsubstituted, saturated or unsaturated aryl group having 10 to 50 carbon atoms, and specific examples of each of $A_1$ to $A_4$ include the same examples as those described for each of $R_1$ to $R_4$.

In each of the general formulae (III) to (V), $A_1$ to $A_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted silyl group having 1 to 20 carbon atoms, or a substituted or unsubstituted heterocyclic group having 5 to 50 carbon atoms, specific examples of each of $A_5$ to $A_8$ include the same examples as those described for each of $R_1$ to $R_4$. c, d, e, and f each independently represent an integer of 0 to 5. When any one of c, d, e, and f represents 2 or more, corresponding multiple $A_1$s, $A_2$s, $A_3$s, or $A_4$s may be identical to or different from each other, or may be coupled with each other to form a saturated or unsaturated ring, and $A_1$ and $A_2$, or $A_3$ and $A_4$ may be coupled with each other to form a saturated or unsaturated ring.

It should be noted that, in the general formula (III), at least one of c and d, and at least one of e and f each represent 2 or more. In addition, in the general formula (IV), at least one of $A_5$ and $A_6$, and at least one of $A_7$ and $A_8$ each represent a substituted or unsubstituted silyl group having 1 to 20 carbon atoms. In addition, in the general formula (V), at least one of $A_5$ and $A_6$, and at least one of $A_7$ and $A_8$ each represent a substituted or unsubstituted cycloalkyl group having 3 to 50 carbon atoms.

Particularly preferable examples of the above heterocyclic ring include rings each derived from pyridine, quinoline, isoquinoline, dibenzofuran, or dibenzothiophene. In addition, particularly preferable examples of the above aryl group include a β-naphthyl group, an m-biphenyl group, a p-biphenyl group, a terphenyl group, and a fluorenyl group. Particularly preferable examples of the silyl group include a trimethylsilyl group and a triphenylsilyl group. A cyclopentyl group or a cyclohexyl group is a preferable cycloalkyl group.

In the general formula (VI), $A_1$ to $A_4$ each independently represent a substituted or unsubstituted aryl group having 5 to 50 carbon atoms, or a substituted or unsubstituted heterocyclic group having 5 to 50 carbon atoms, specific examples of each of $A_1$ to $A_4$ include the same examples as those described for each of $R_1$ to $R_4$, and when $A_1$ to $A_4$ each represent an aryl group, $A_1$ and $A_2$, $Ar_1$ and $A_1$, $A_3$ and $A_4$, or $Ar_2$ and $A_3$ may be coupled with each other to form a saturated or unsaturated ring; provided that $Ar_1$ and $Ar_2$ are different from each other, and the case where both of $Ar_1$ and $Ar_2$ each represent a heterocyclic group is excluded.

In the general formula (VII), at least one of c and d, and at least one of e and f each represent 2 or more. Preferable examples when at least one of c and d, and at least one of e and f each represent 2 include a 3,4-dimethylphenyl group, a 3,5-dimethylphenyl group, and a 2,4-dimethylphenyl group. Preferable examples when at least one of c and d, and at least one of e and f each represent 3 include a 2,4,6-trimethylphenyl group and a 3,4,5-trimethylphenyl group.

The aromatic amine derivative of the present invention is preferably a doping material for an organic electroluminescence device.

In addition, the present invention provides an organic EL device having an organic thin film layer composed of one or more layers including at least a light emitting layer and interposed between a cathode and an anode, in which at least one layer of the organic thin film layer contains the aromatic amine derivative alone or as a component of a mixture.

In addition, the organic electroluminescence device of the present invention is preferably such that the light emitting layer contains the aromatic amine derivative alone or as a component of a mixture.

In each of the general formulae (I) to (VIII), two arbitrary adjacent groups of $A_1$ to $A_8$ are coupled with each other to form a saturated or unsaturated ring in some cases.

Examples of the ring include: cycloalkanes each having 4 to 12 carbon atoms such as cyclobutane, cyclopentane, cyclohexane, adamantane, and norbornane; cycloalkenes each having 4 to 12 carbon atoms such as cyclobutene, cyclopentene, cyclohexene, cycloheptene, and cyclooctene; cycloalkadienes each having 6 to 12 carbon atoms such as cyclohexadiene, cycloheptadiene, and cyclooctadiene; aromatic rings each having 6 to 50 carbon atoms such as benzene, naphthalene, phenanthrene, anthracene, pyrene, chrysene, and acenaphthylene; and heterocyclic rings each having 5 to 50 carbon atoms such as imidazole, pyrrole, furan, thiophene, and pyridine.

Examples of a substituent for each group include a substituted or unsubstituted aryl group having 5 to 50 ring carbon atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring carbon atoms, a substituted or unsubstituted aryloxy group having 5 to 50 ring carbon atoms, a substituted or unsubstituted arylthio group having 5 to 50 ring carbon atoms, a substituted or unsubstituted alkoxycarbonyl group having 1 to 50 carbon atoms, an amino group, a halogen atom, a cyano group, a nitro group, a hydroxyl group, and a carboxyl group.

Specific examples of the aromatic amine derivative represented by any one of the general formulae (I) to (VIII) of the present invention are shown below. However, the aromatic amine derivative is not limited to these exemplified compounds. It should be noted that Me represents a methyl group.

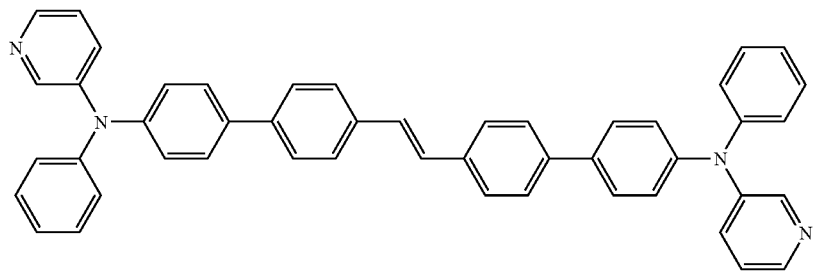
D-1-1
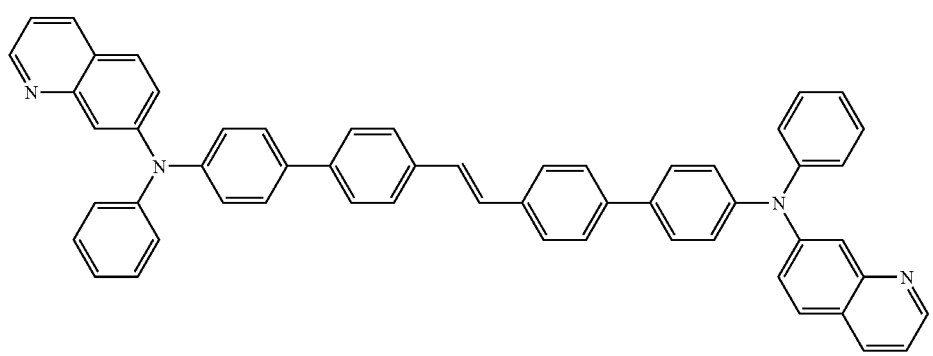
D-1-2
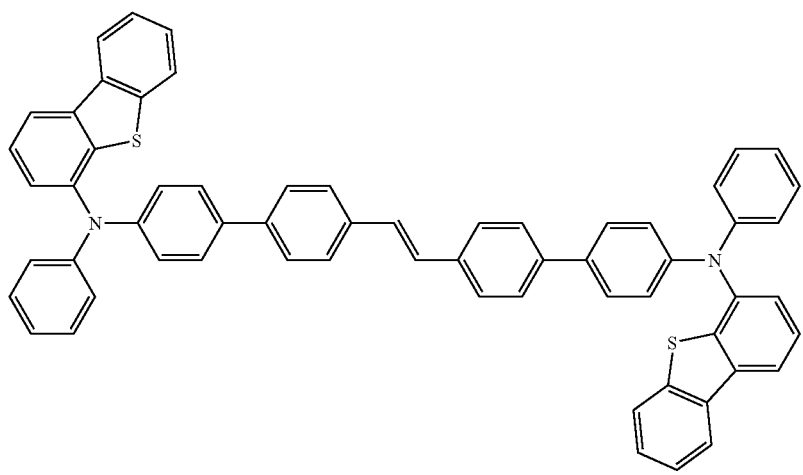
D-1-3
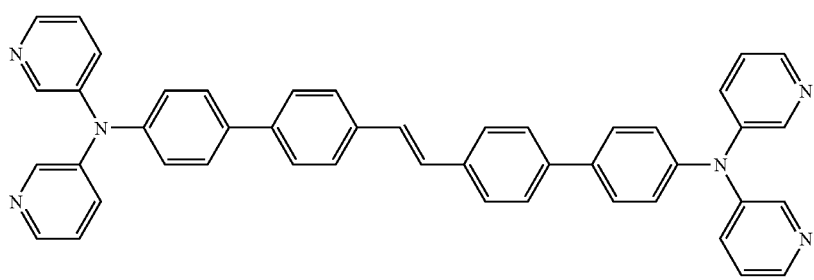
D-1-4

-continued
D-1-5
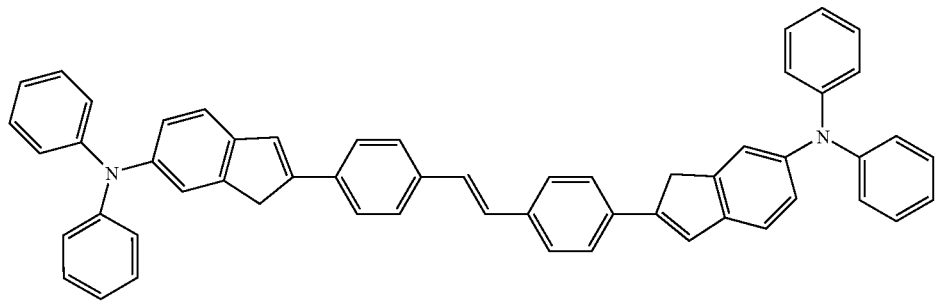
D-1-6
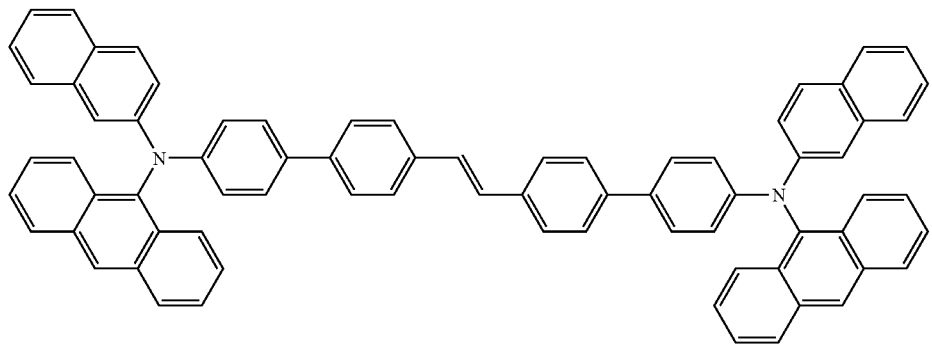
D-1-7
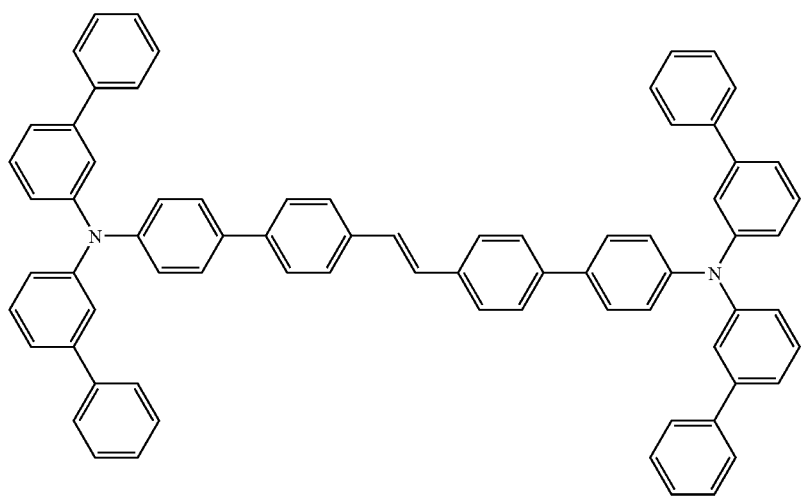
D-1-8
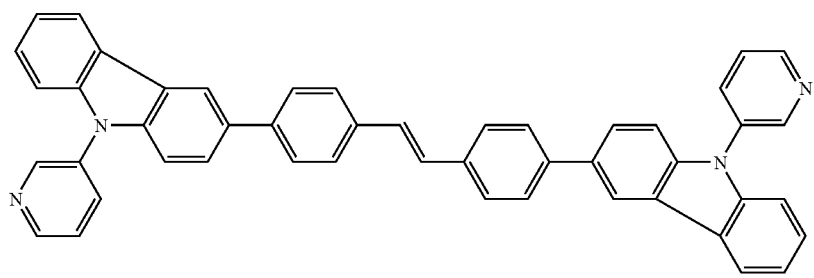

-continued
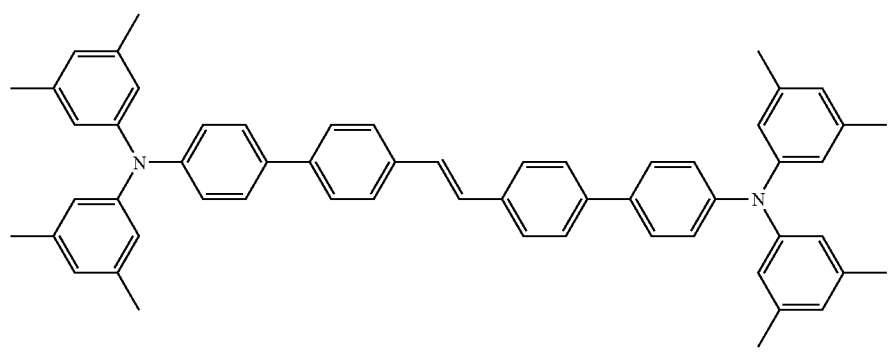
D-2-1
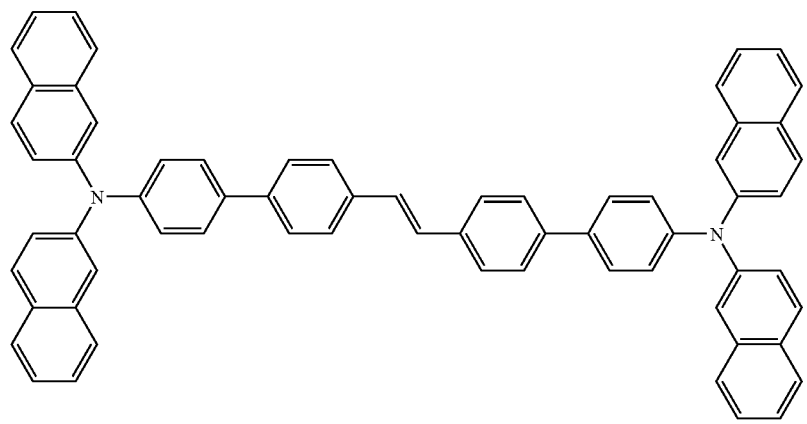
D-2-2
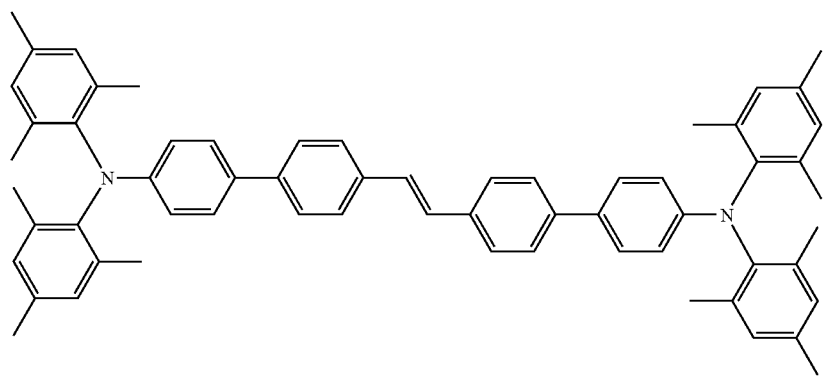
D-2-3
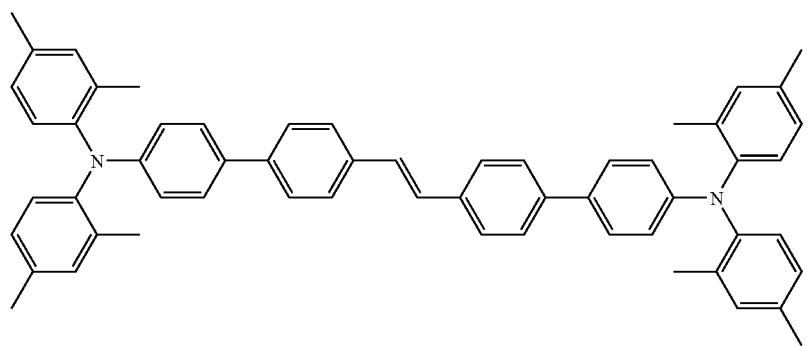
D-2-4

-continued
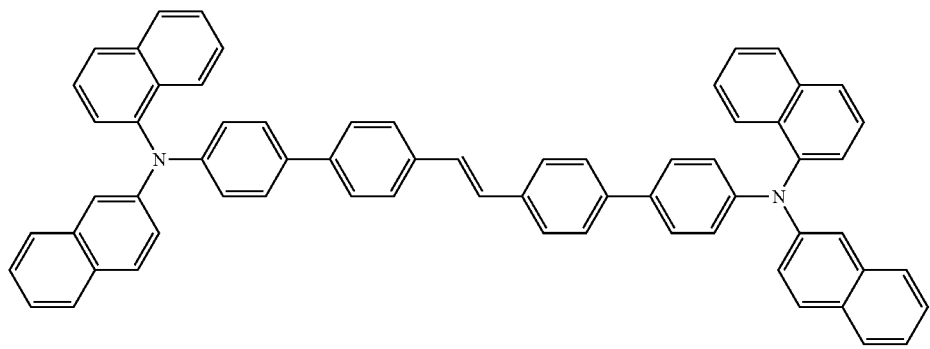
D-2-5
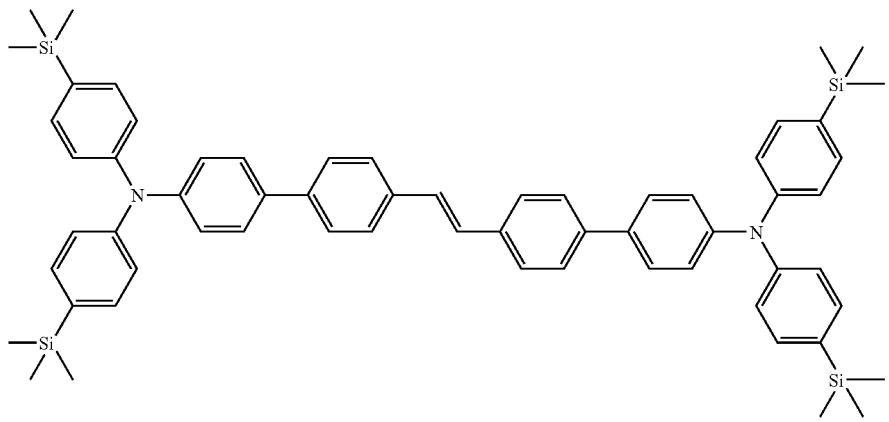
D-2-6
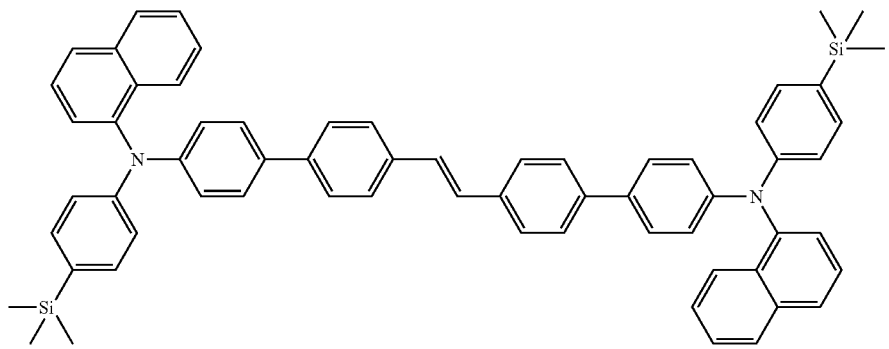
D-2-7
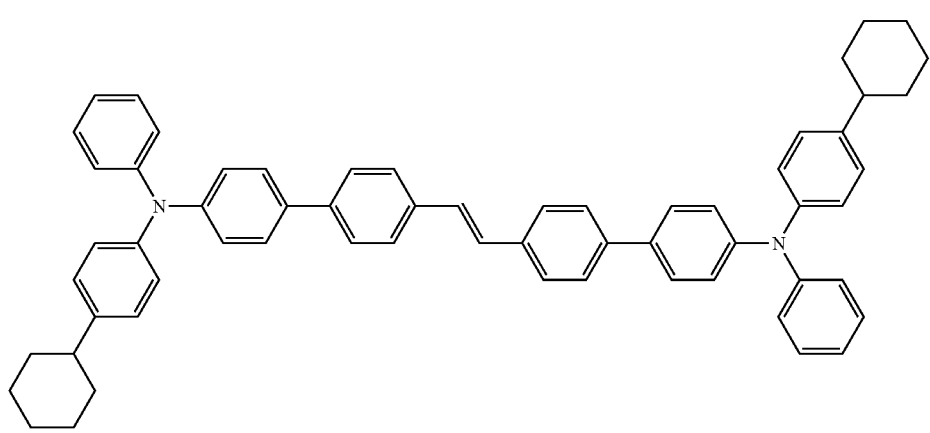
D-2-8

-continued
D-3-1
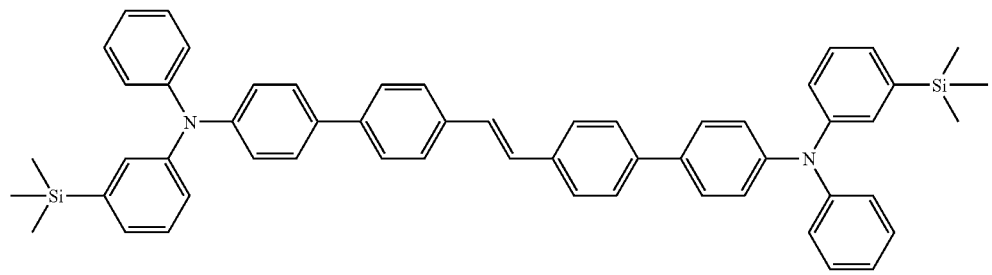
D-3-2
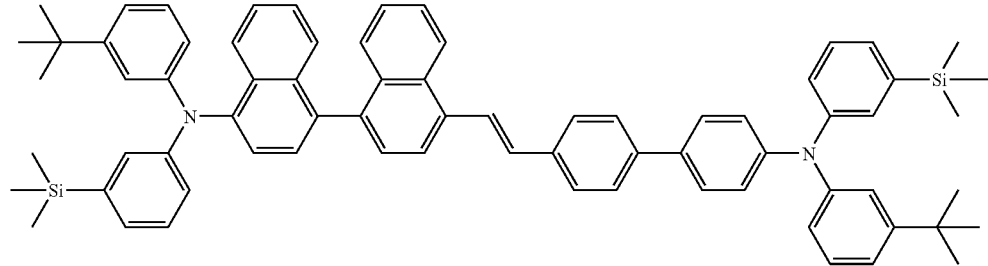
D-3-3
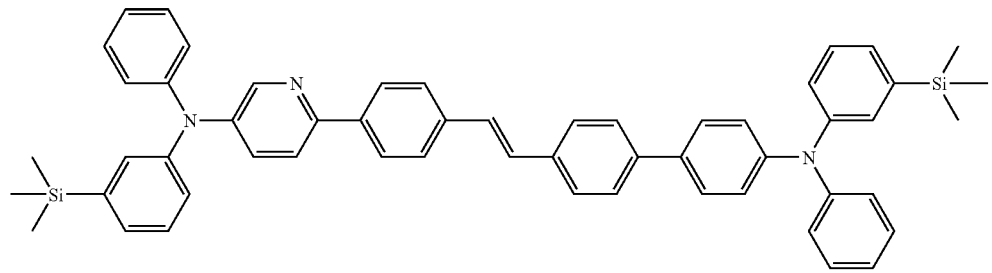
D-3-4
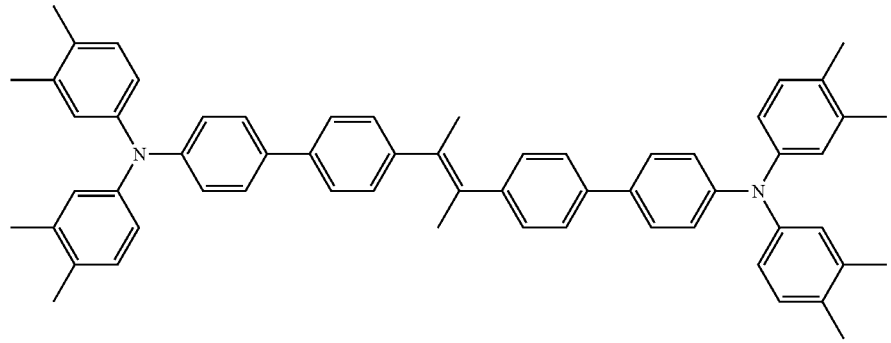
D-3-5
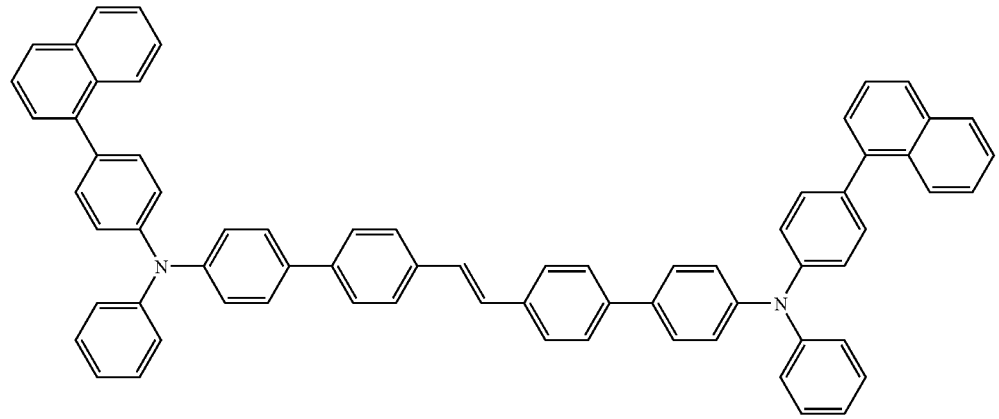

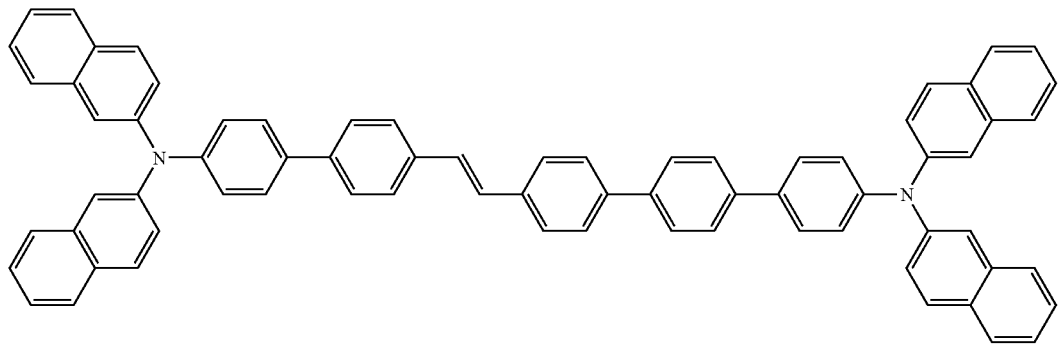
D-3-6
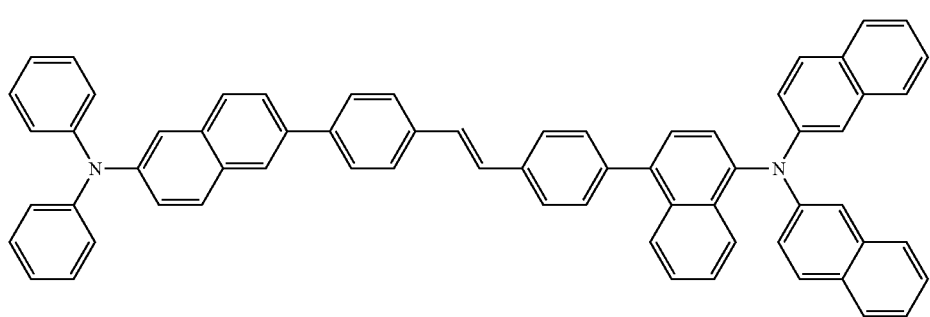
D-3-7
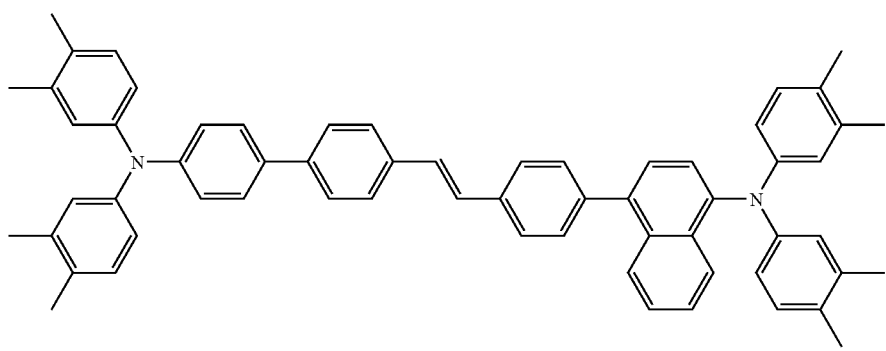
D-3-8
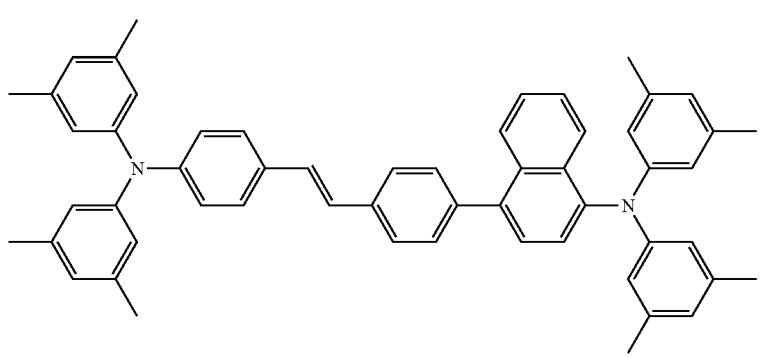
D-4-1

-continued
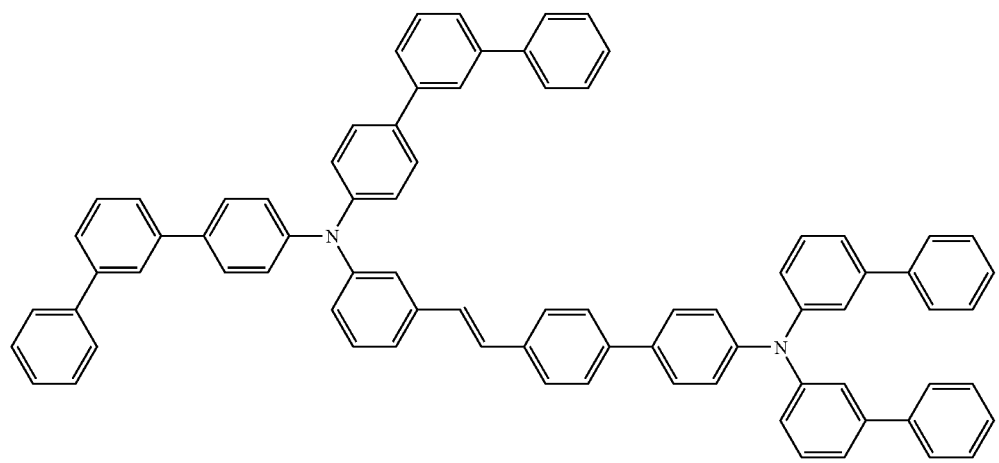
D-4-2
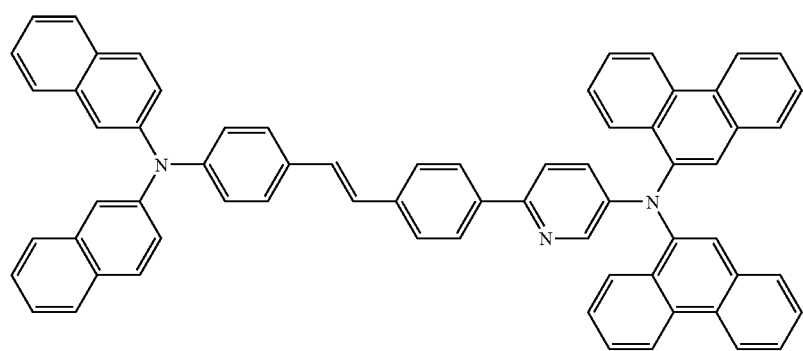
D-4-3
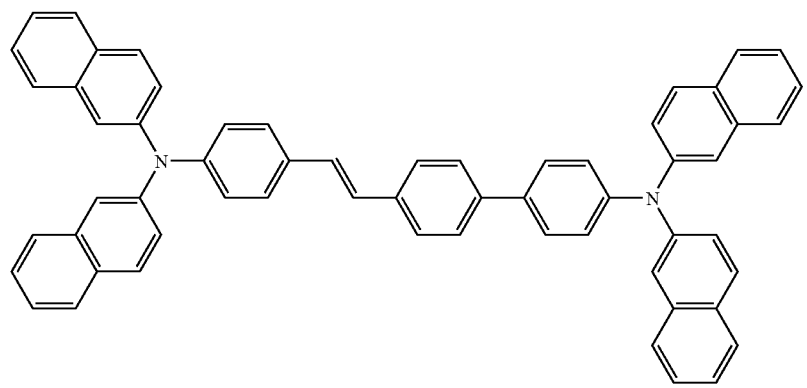
D-4-4
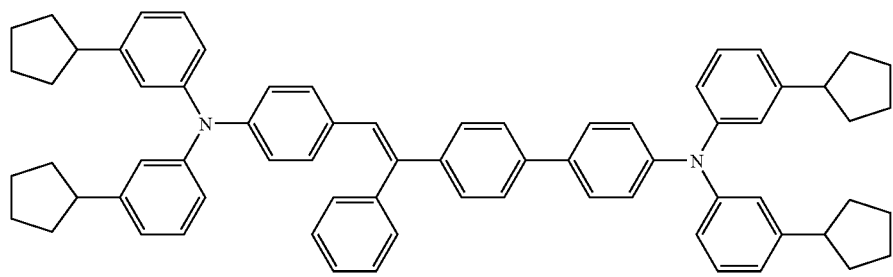
D-4-5

-continued
D-4-6
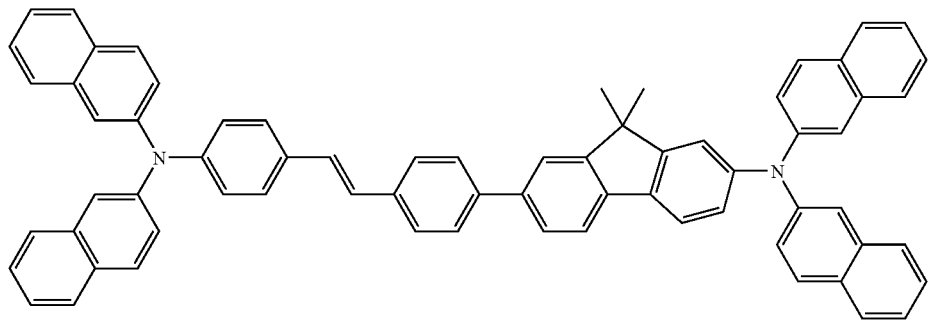
D-4-7
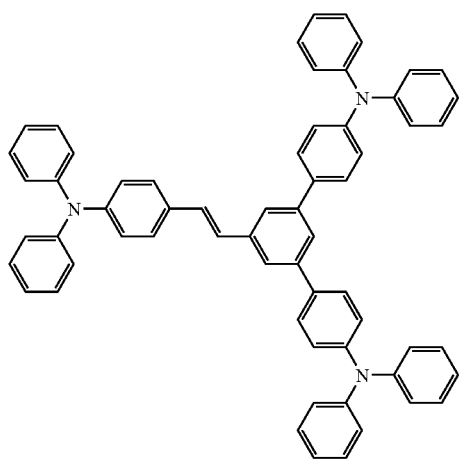
D-4-8
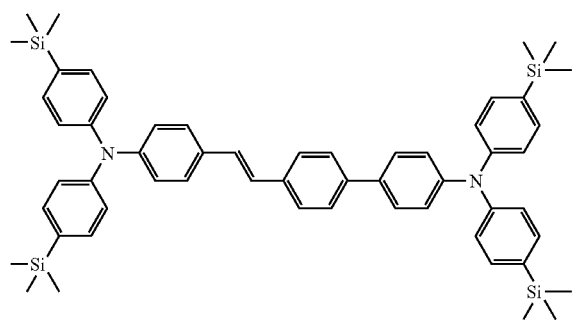
D-5-1
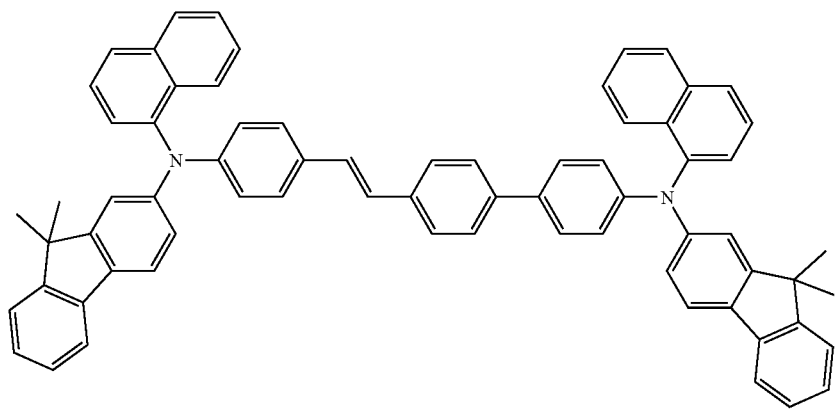
D-5-2
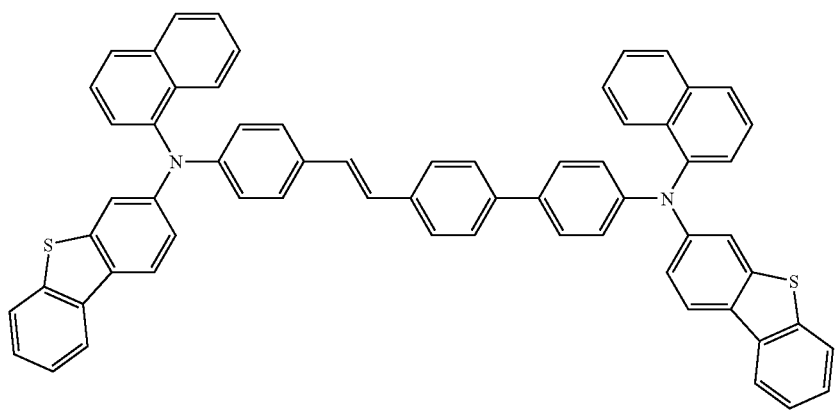

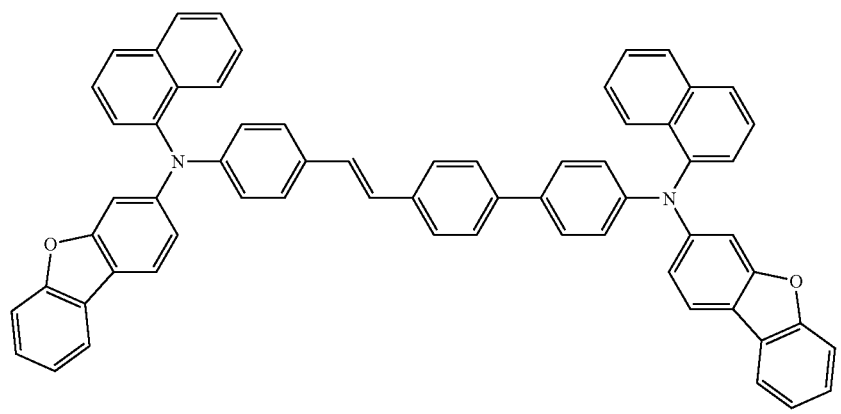
D-5-3
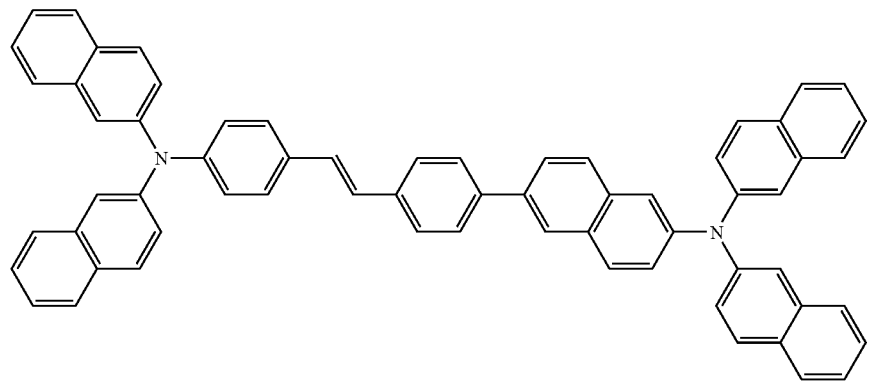
D-5-4
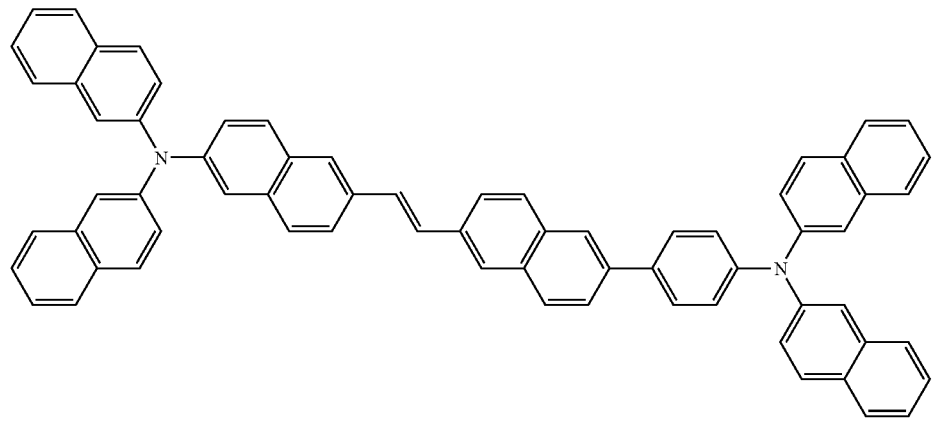
D-5-5
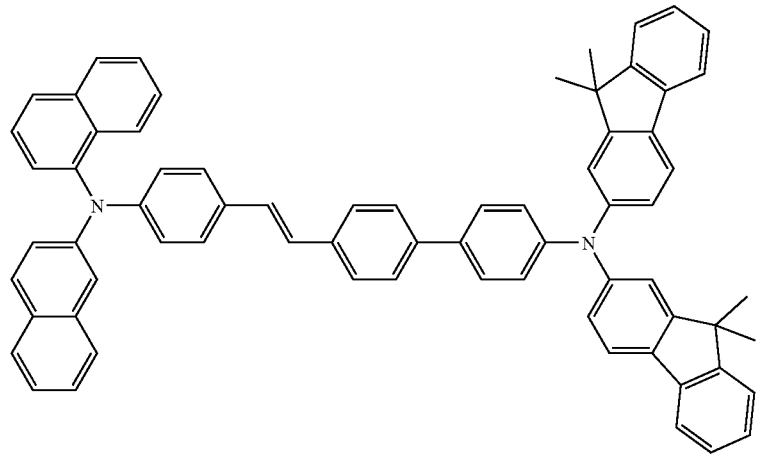
D-5-6

D-5-7

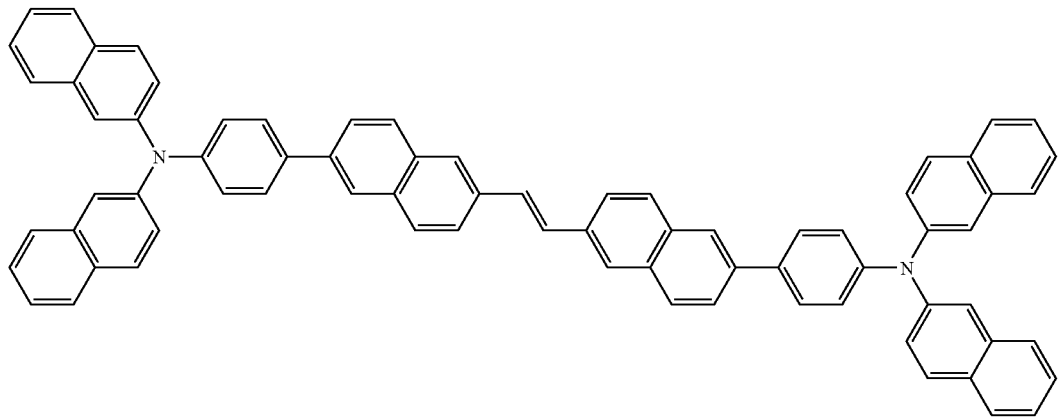

D-5-8

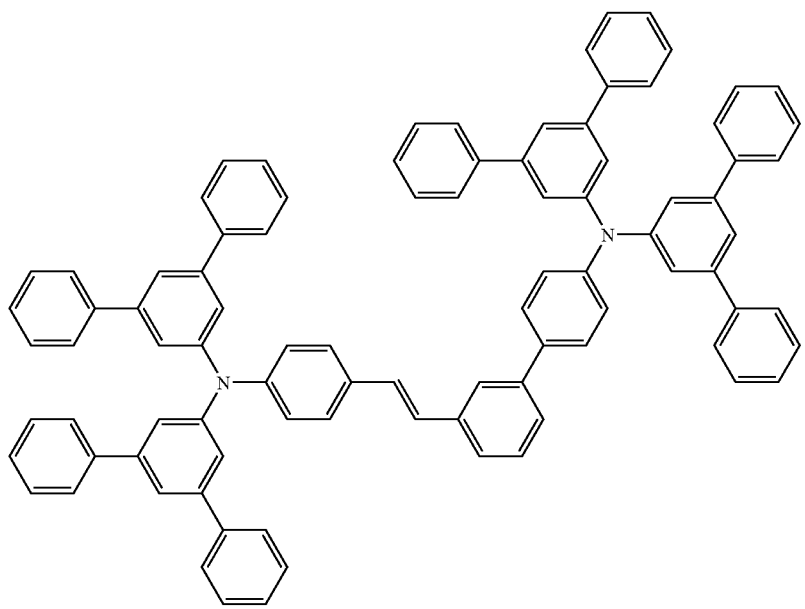

Next, a method of producing the aromatic amine derivative of the present invention will be described.

The method of producing the aromatic amine derivative represented by any one of the general formulae (I) to (VIII) of the present invention is not particularly limited, and the derivative has only to be produced by a known method. For example, an aromatic amine is produced by aminating a halogen derivative obtained by a method described in, for example, Journal of Chemistry, vol. 38, p. 493 to 499 (1973), Journal of Organometallic Chemistry, vol. 616, p. 80 to 88 (2000), or Organic Letter, vol. 6, p. 2933 to 2936 (2004) with diarylamine (for example, Journal of Chemistry, vol. 65, p. 1158 to 1174 (2000)).

The aromatic amine derivative of the present invention is preferably used as a material for an organic EL device, and is more preferably used as a light emitting material for an organic EL device, in particular, a doping material for an organic EL device.

The organic EL device of the present invention is an organic electroluminescence device having an organic compound layer composed of one or more layers including at least a light emitting layer and interposed between a pair of electrodes, in which at least one layer of the organic compound layer contains at least one kind of the aromatic amine derivative of the present invention.

In the organic EL device of the present invention, the light emitting layer preferably contains at least one kind of the aromatic amine derivative; the content of the aromatic amine derivative of the present invention in the light emitting layer is preferably 0.01 to 20 wt %, more preferably 0.5 to 20 wt %, particularly preferably 1 to 20 wt %, or most preferably 5 to 20 wt %.

In addition, when the aromatic amine derivative of the present invention is used as a light emitting material of an organic EL device, the light emitting layer preferably contains at least one kind of the aromatic amine derivative and at least one kind selected from the compounds represented by the following general formulae (2a) to (2d), and the at least one kind selected from the compounds represented by the following general formulae (2a) to (2d) is preferably a host material.

Hereinafter, the general formulae (2a) to (2d) will be described:

General Formula (2a)

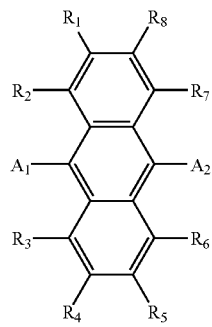

(2a)

where: $A_1$ and $A_2$ each independently represent a group derived from a substituted or unsubstituted aromatic ring having 6 to 20 ring carbon atoms, the aromatic ring may be substituted by at least one substituent, the at least one substituent is selected from a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group, and when the aromatic ring is substituted by two or more substituents, the substituents may be identical to or different from each other, and adjacent substituents may be bonded to each other to form a saturated or unsaturated cyclic structure; and $R_1$ to $R_8$ are each independently selected from a hydrogen atom, a substituted or unsubstituted aryl group having 6 to 50 ring carbon atoms, a substituted or unsubstituted heteroaryl group having 5 to 50 ring atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group.

In the general formula (2a), $A_1$ and $A_2$ described above preferably represent different groups.

In the general formula (2a), at least one of $A_1$ and $A_2$ preferably represents a substituent having a substituted or unsubstituted fused ring group having 10 to 30 ring atoms.

The substituted or unsubstituted fused ring group having 10 to 30 ring atoms is preferably a substituted or unsubstituted naphthalene ring.

Examples of the group derived from substituted or unsubstituted aromatic ring having 6 to 20 carbon atoms in any one of $A_1$ or $A_2$ in the general formula (2a) include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group. The group derived from a substituted or unsubstituted aromatic ring having 10 to 14 carbon ring atoms is preferred. Especially, a 1-naphthyl group, a 2-naphthyl group, and a 9-phenanthryl group are preferred.

Examples of the substituted or unsubstituted aryl group having 6 to 50 carbon ring atoms as the substituent of the above-mentioned aromatic ring include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group; a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4"-t-butyl-p-terphenyl-4-yl group. The substituted or unsubstituted aryl group having 6 to 18 carbon ring atoms is preferred. Especially, a phenyl group, a 1-naphthyl group, a 2-naphthyl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, an o-tolyl group, a m-tolyl group, a p-tolyl group, and a p-t-butylphenyl group are preferred.

$A_1$ and $A_2$ in the general formula (2a) each independently represent a substituted or unsubstituted aromatic ring group having 10 to 30 ring carbon atoms (except an anthracene residue). Substituents for $A_1$ and $A_2$ are each independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, or a hydroxyl group.

Examples of the aromatic ring group having 10 to 30 ring carbon atoms (except an anthracene residue) represented by each of $A_1$ and $A_2$ in the general formula (2a) include: a substituted or unsubstituted α-naphthyl group and a substituted or unsubstituted β-naphthyl group; a substituted or unsubstituted phenanthrenyl group; a substituted or unsubstituted chrysenyl group; a substituted or unsubstituted tetracenyl group; a substituted or unsubstituted pyrenyl group; a substituted or unsubstituted phenylnaphthyl group; a substituted or unsubstituted naphthylnaphthyl group; a substituted or unsubstituted naphthylphenyl group; a substituted or unsubstituted phenylpyrenyl group; a substituted or unsubstituted pyrenylphenyl group; a substituted or unsubstituted naphthylnaphthylnaphthyl group; a substituted or unsubstituted naphthylnaphthylphenyl group; a substituted or unsubstituted naphthylphenylphenyl group; a substituted or unsubstituted naphthylphenylnaphthyl group; a substituted or unsubstituted phenylnaphthylnaphthyl group; a substituted or unsubstituted phenylnaphthylphenyl group; and a substituted or unsubstituted phenylphenylnaphthyl group. Of those, a substituted or unsubstituted α-naphthyl group, a substituted or unsubstituted β-naphthyl group, a substituted or unsubstituted phenylnaphthyl group, a substituted or unsubstituted naphthylnaphthyl group, or a substituted or unsubstituted naphthylphenyl group is preferable.

Examples of groups of a substituted or unsubstituted aryl group having 6 to 50 ring carbon atoms in any one of $R_1$ to $R_8$ in the general formula (2a) include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group.

Examples of groups of a substituted or unsubstituted heteroaryl group having 5 to 50 ring carbon atoms in any one of $R_1$ to $R_8$ in the general formula (2a) include a 1-pyrolyl group, a 2-pyrolyl group, a 3-pyrolyl group, a pyradinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenadinyl group, a 2-phenadinyl group, a 1-phenothiadinyl group, a 2-phenothiadinyl group, a 3-phenothiadinyl group, a 4-phenothiadinyl group, a 10-phenothiadinyl group, a 1-phenoxadinyl group, a 2-phenoxadinyl group, a 3-phenoxadinyl group, a 4-phenoxadinyl group, a 10-phenoxadinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Examples of substituents for a substituted or unsubstituted alkyl group having 1 to 50 carbon atoms in any one of $R_1$ to $R_8$ in the general formula (2a) and the above aromatic ring include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group.

Examples of substituents for a substituted or unsubstituted cycloalkyl group having 3 to 50 carbon atoms in any one of $R_1$ to $R_8$ in the general formula (2a) and the above aromatic ring include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

Examples of substituents for a substituted or unsubstituted alkoxy group having 1 to 50 ring carbon atoms in any one of $R_1$ to $R_8$ in the general formula (2a) and the above aromatic ring is represented by —OY, and Y includes the same examples as a substituted or unsubstituted alkyl group having 1 to 50 carbon atoms in substituents of any one of $R_1$ to $R_8$ in the general formula (2a) and in the above aromatic ring.

Examples of substituents for a substituted or unsubstituted aralkyl group having 6 to 50 carbon atoms in any one of $R_1$ to $R_8$ in the general formula (2a) and the above aromatic ring include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

The substituted or unsubstituted aryloxy group having 5 to 50 ring atoms, and the substituted or unsubstituted arylthio group having 5 to 50 ring atoms each corresponding to any one of $R_1$ to $R_8$ and the substituents for the aromatic ring in the general formula (2a) are represented by —OY' and —SY", respectively. Examples of each of Y' and Y" include examples similar to those described for the substituted or unsubstituted aryl group having 6 to 50 ring atoms corresponding to any one of $R_1$ to $R_8$ and the substituents for the aromatic ring described above.

The substituted or unsubstituted alkoxycarbonyl group having 1 to 50 carbon atoms corresponding to any one of $R_1$ to $R_8$ and the substituents for the aromatic ring in the general formula (2a) is represented by —COOZ. Examples of Z include examples similar to those described for the substituted or unsubstituted alkyl group having 1 to 50 carbon atoms corresponding to any one of $R_1$ to $R_8$ and the substituents for the aromatic ring described above.

Examples of the silyl group corresponding to any one of $R_1$ to $R_8$ and the substituents for the aromatic ring in the general formula (2a) include a trimethylsilyl group, a triethylsilyl group, a t-butyldimethylsilyl group, a vinyldimethylsilyl group, a propyldimethylsilyl group, and a triphenylsilyl group.

Examples of the halogen atom corresponding to any one of $R_1$ to $R_8$ and the substituents for the aromatic ring in the general formula (2a) include fluorine, chlorine, bromine, and iodine.

Examples of substituents for a substituent in any of $R_1$ to $R_8$ and the above aromatic ring include a halogen atom, a hydroxyl group, a nitro group, a cyano group, an alkyl group, an aryl group, a cycloalkyl group, an alkoxy group, an aromatic heterocyclic group, an aralkyl group, an aryloxy group, an arylthio group, an alkoxycarbonyl group, and a carboxyl group.

The anthracene derivative represented by the general formula (2a) is preferably a compound having a structure represented by the following general formula (2a'):

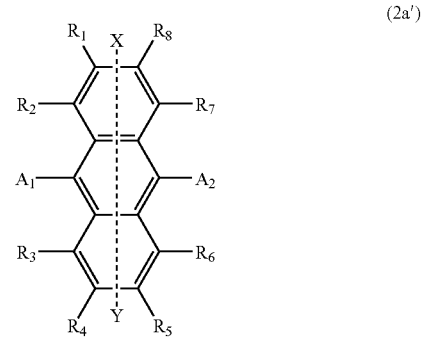

(2a')

where $A_1$ and $A_2$, and $R_1$ to $R_8$ each independently have the same meaning as that in the general formula (2a), and specific examples of each of them include examples similar to those described above, provided that the case where, in the general formula (2a'), groups symmetrical with respect to an X-Y axis shown on central anthracene are bonded to 9- and 10-positions of the anthracene is excluded.

Specific examples of the anthracene derivative represented by the general formula (2a) to be used in the organic EL device of the present invention include various known anthracene derivatives such as an anthracene derivative having two anthracene skeletons in any one of its molecules described in paragraphs [0043] to [0063] of Japanese Patent Application Laid-Open No. 2004-356033 and a compound having one anthracene skeleton described in p. 27 and 28 of WO2005/061656. Representative specific examples are shown below:

51                                                52
2a-1                                              2a-2
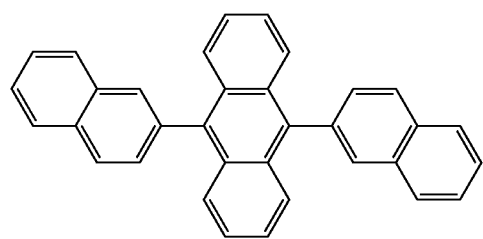                              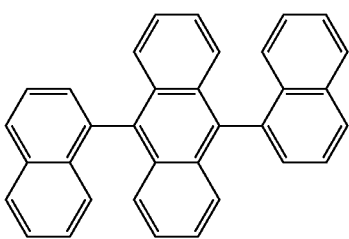
2a-3                                              2a-4
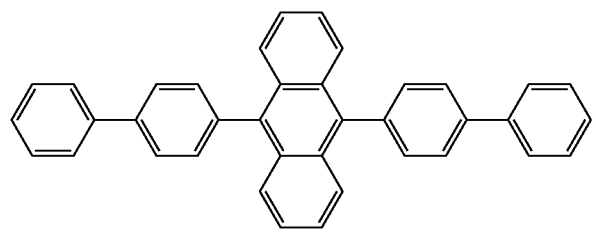                              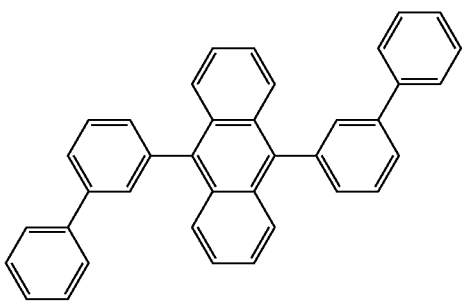
                                                  2a-6
                                                  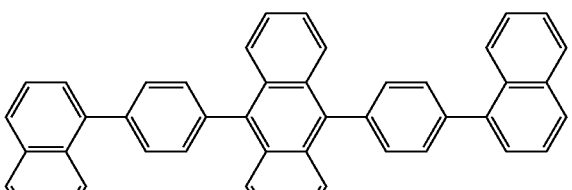
2a-5
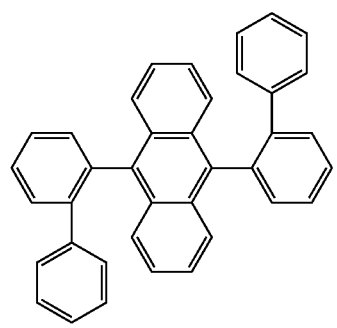
                                                  2a-8
                                                  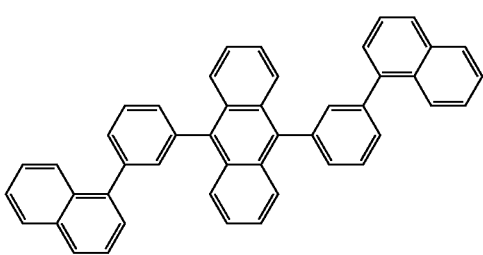
2a-9                                              2a-10
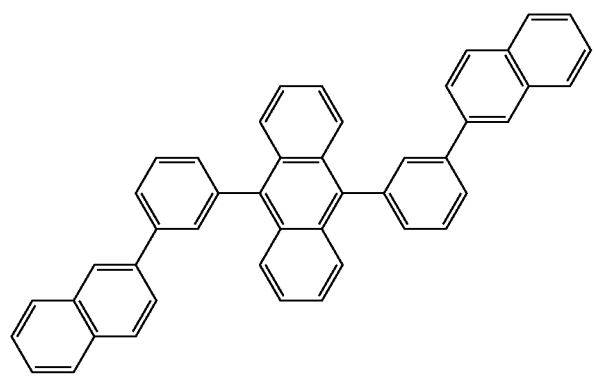                              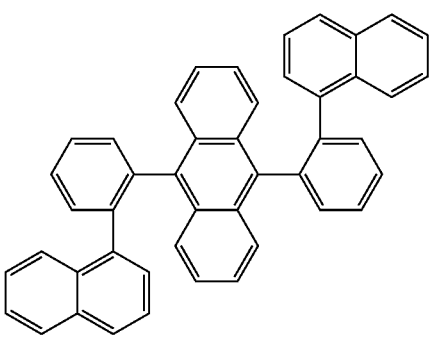

-continued
2a-11
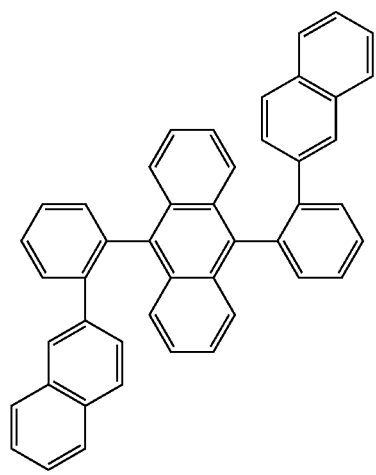
2a-12
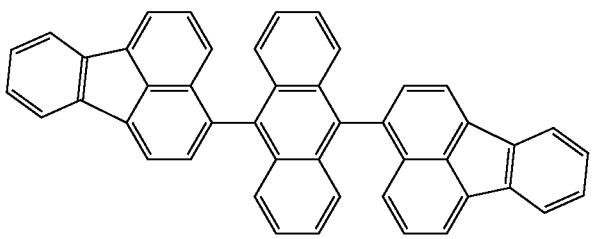
2a-13
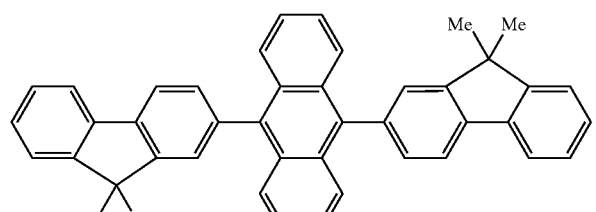
2a-14
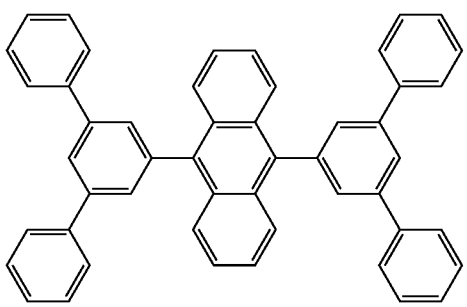
2a-15
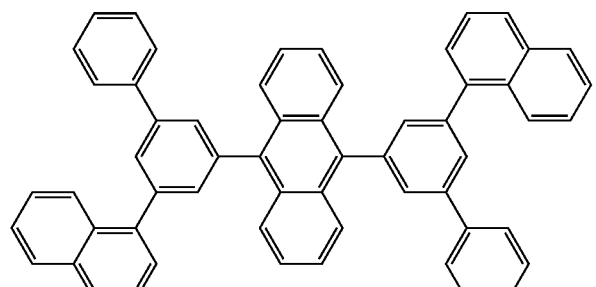
2a-16
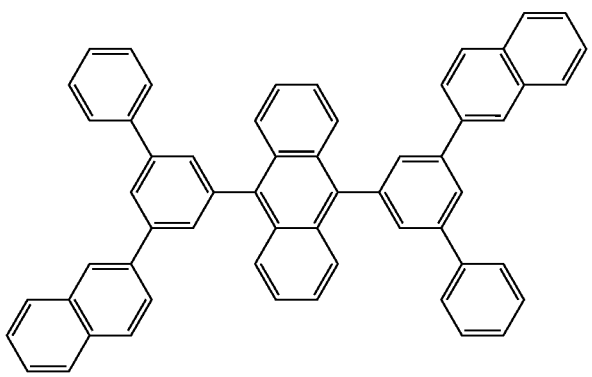
2a-17
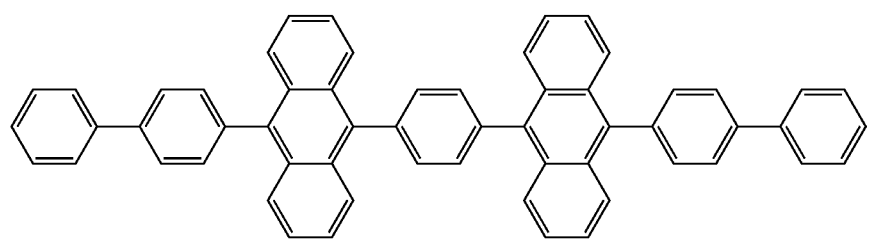

-continued
2a-18
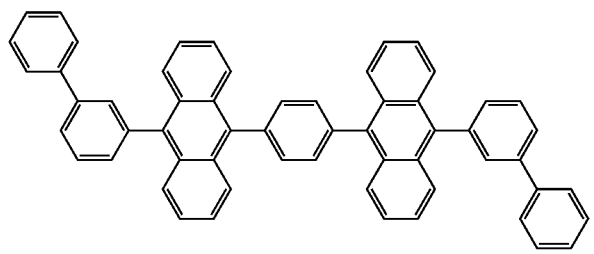
2a-19
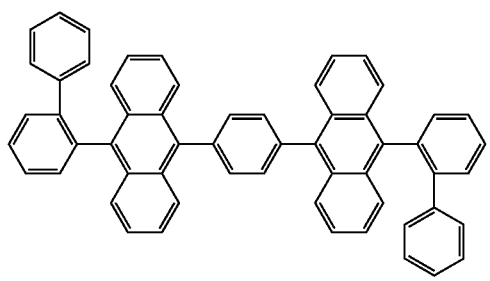
2a-20
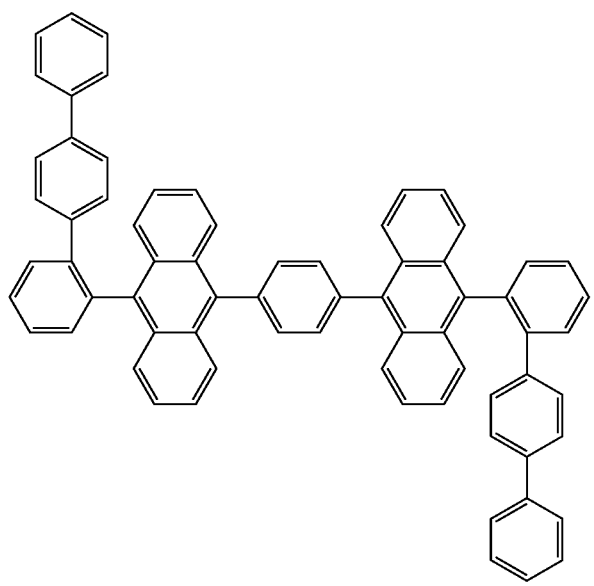
2a-21
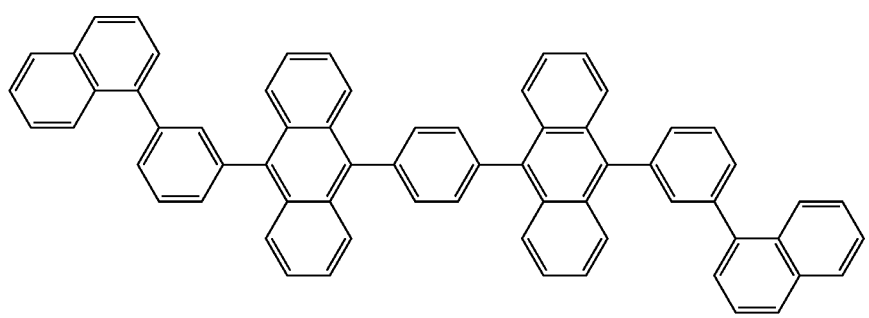
2a-22
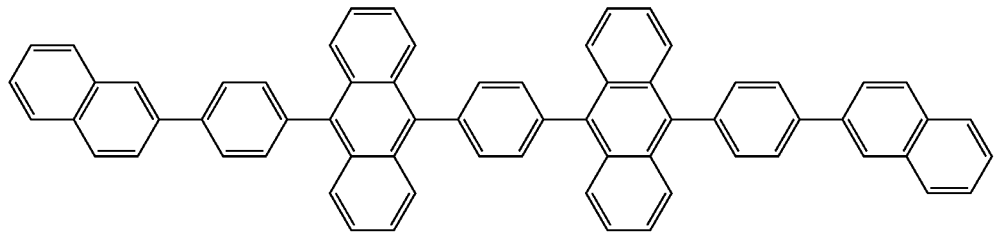

2a-23
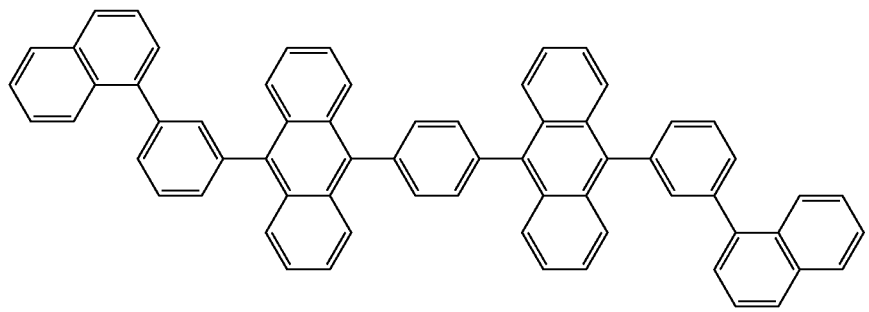
2a-24
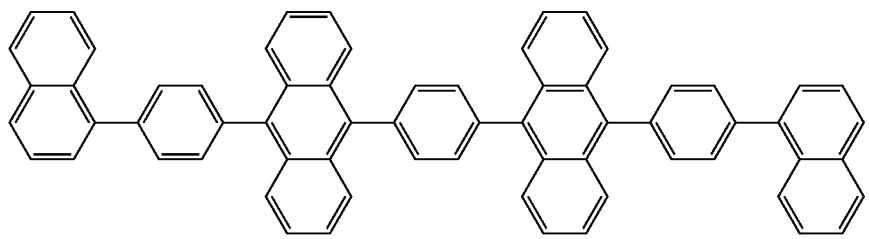
2a-25        2a-26
2a-27        2a-28
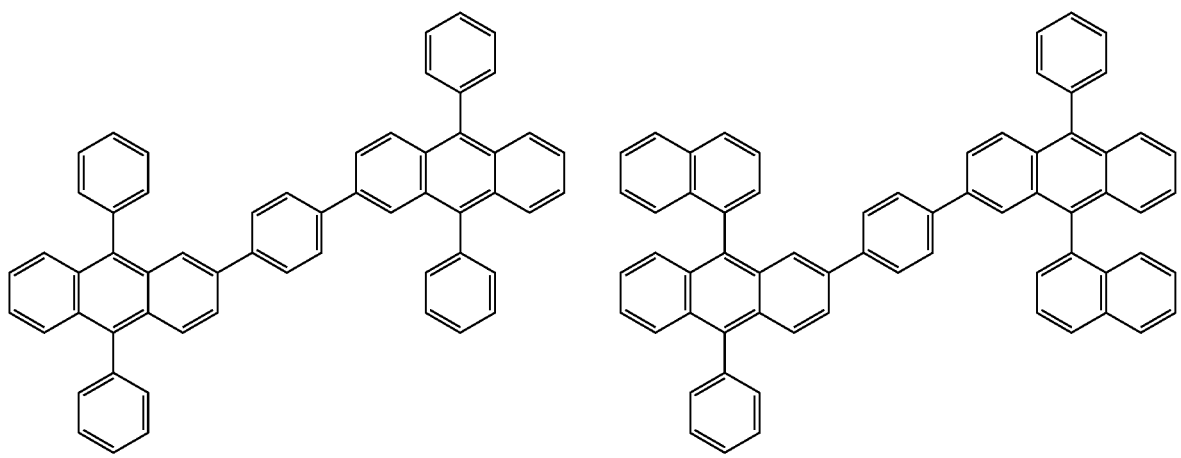
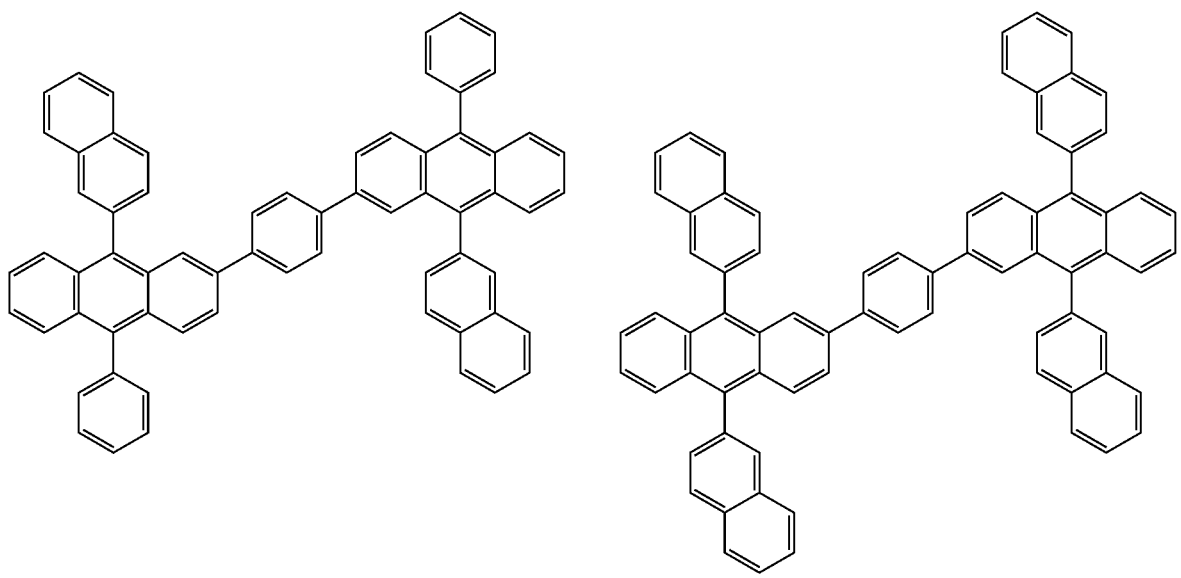

-continued
2a-29
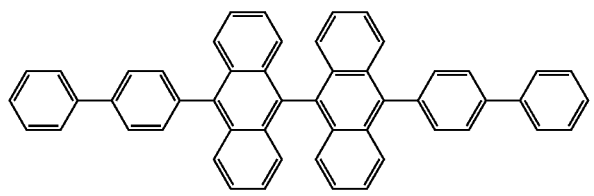
2a-30
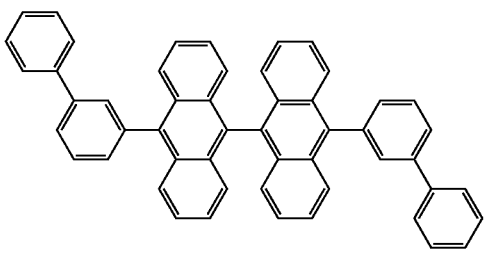
2a-31
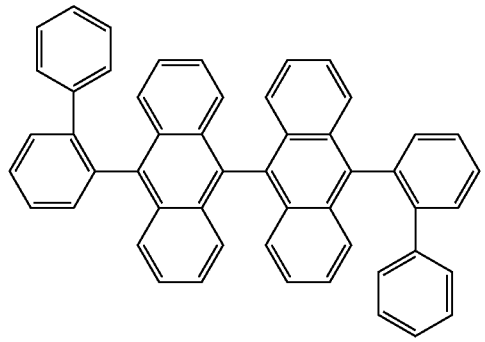
2a-32
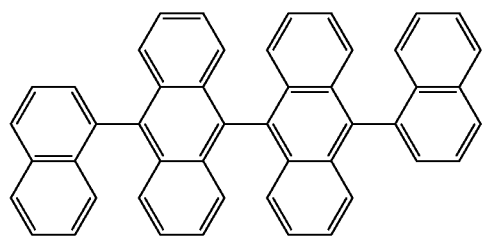
2a-33
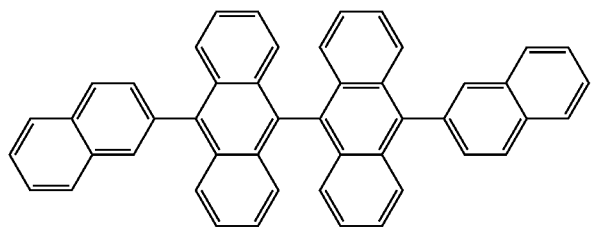
2a-34
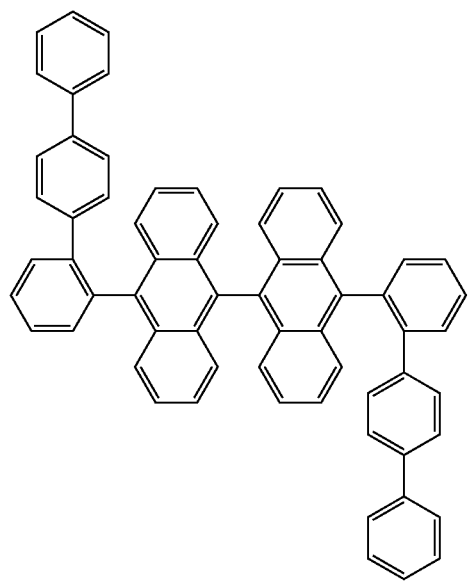
2a-35
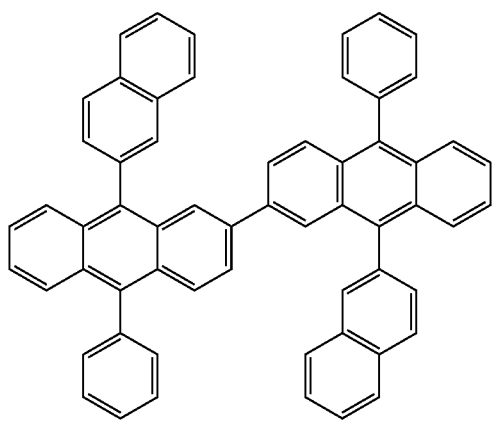
2a-36
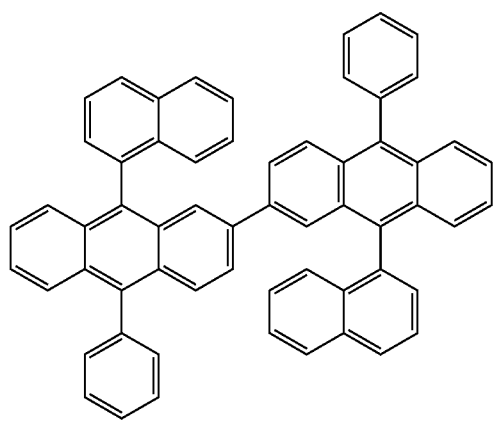

-continued
2a-37
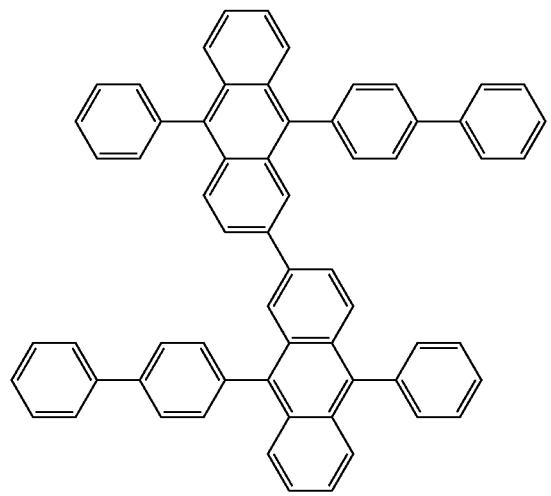
2a-38
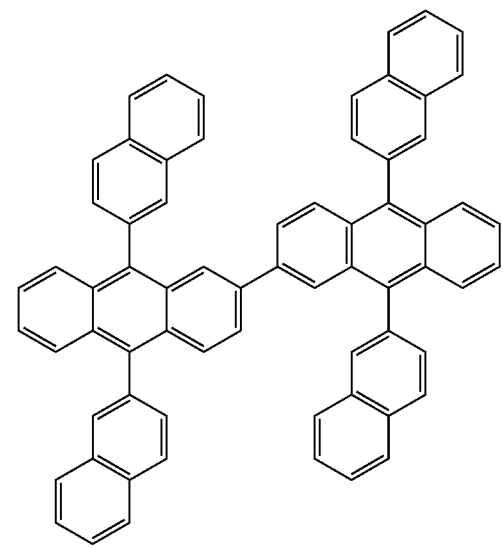
2a-39
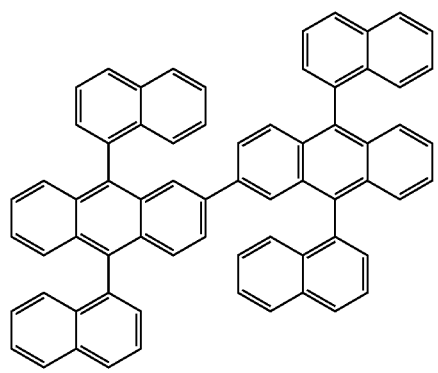
2a-40
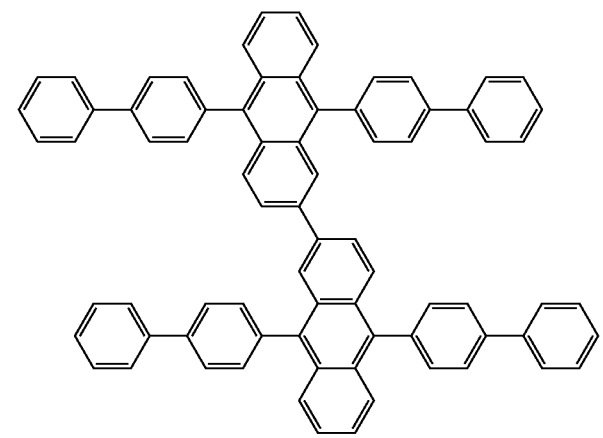
2a-41
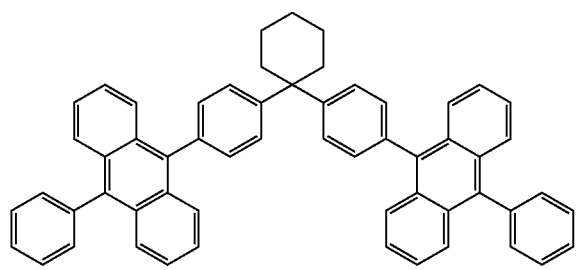
2a-42
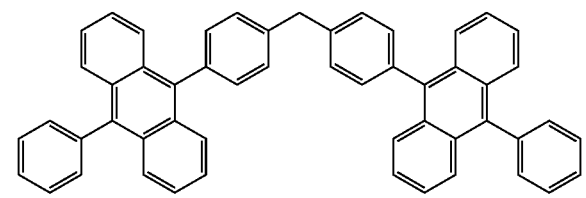
2a-43
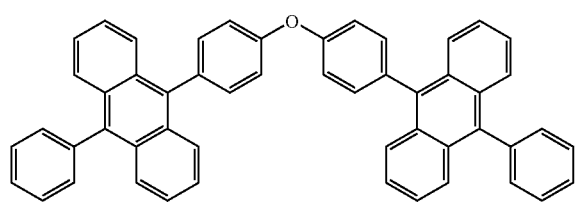
2a-44
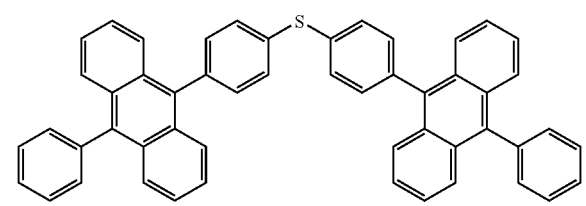

-continued
2a-45
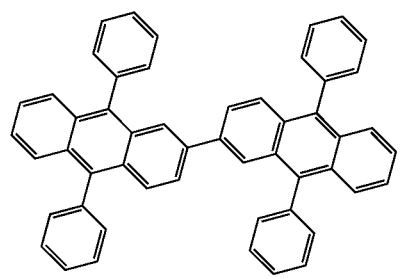
2a-46
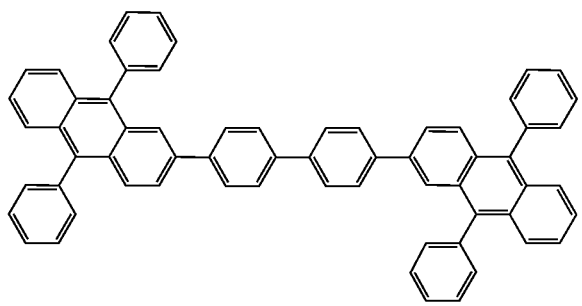
2a-47
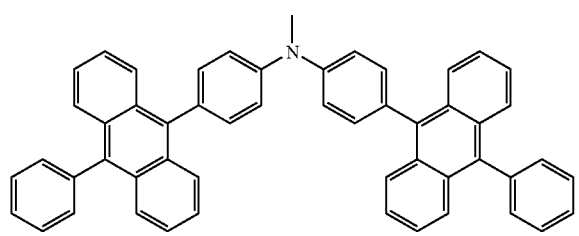
2a-48
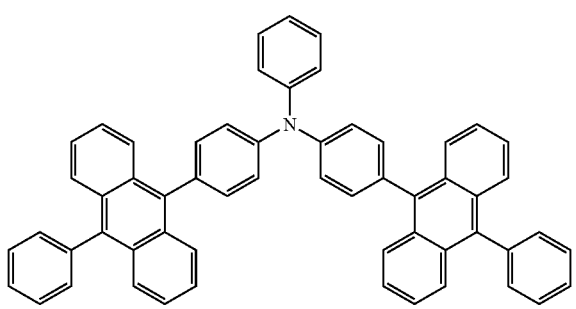
2a-49
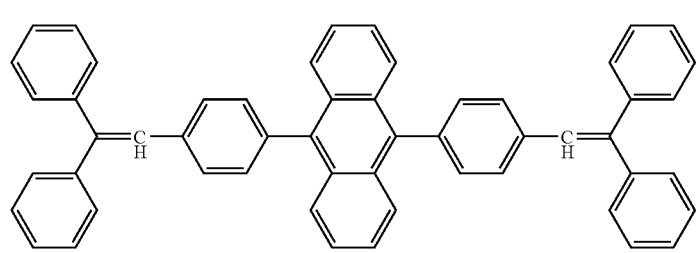
2a-50
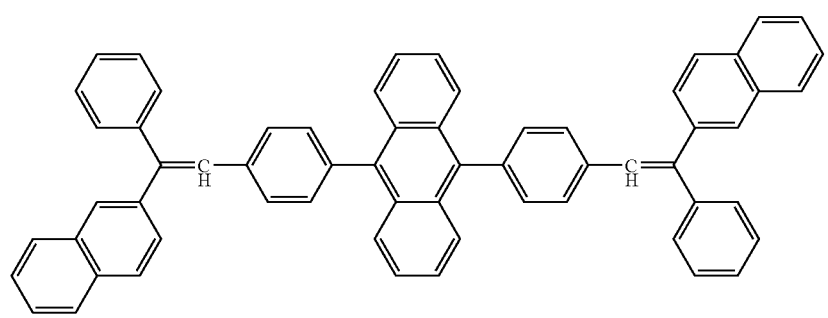

-continued
2a-51
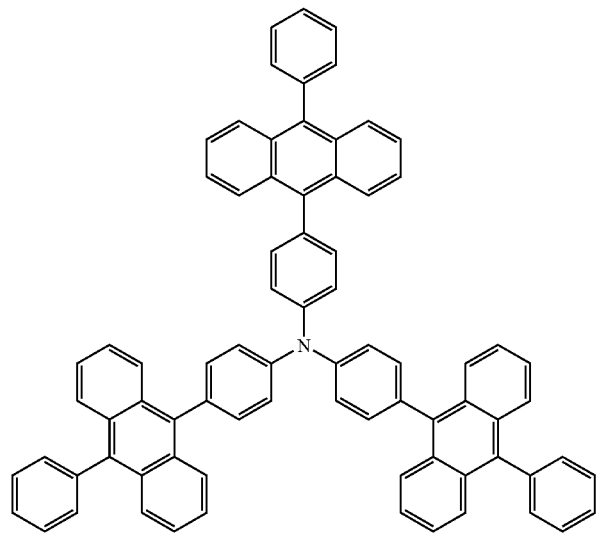
2a'-52
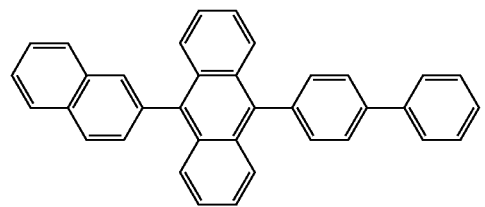
2a'-53
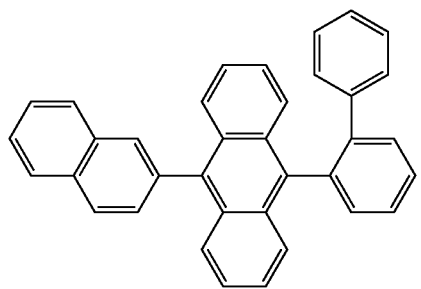
2a'-54
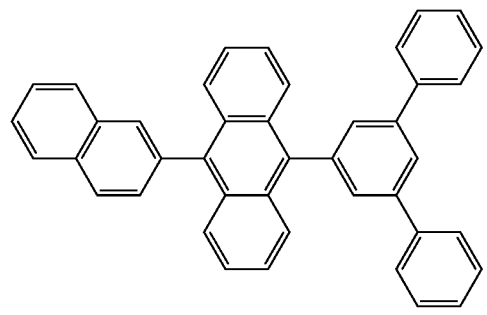
2a'-55
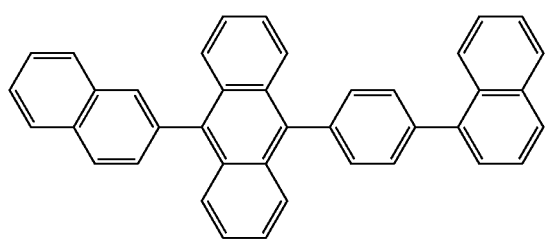
2a'-56
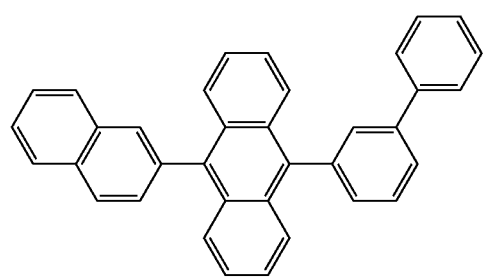
2a'-57
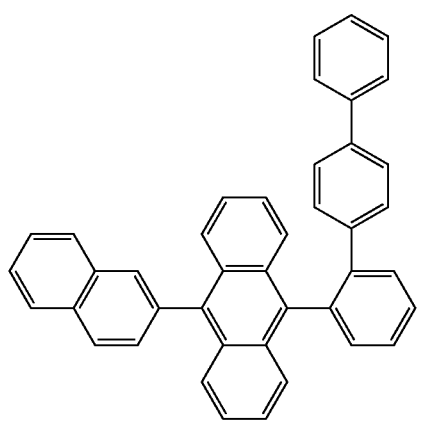
2a'-58
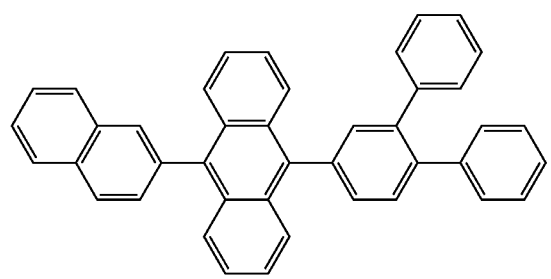

2a'-59
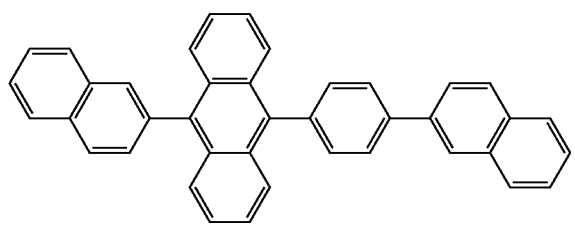
2a'-60
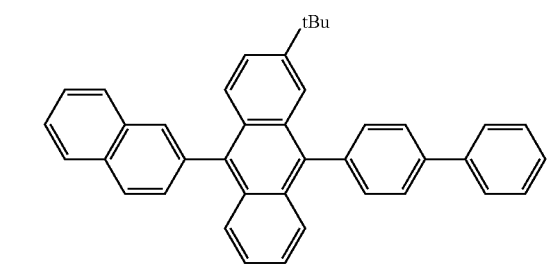
2a'-61
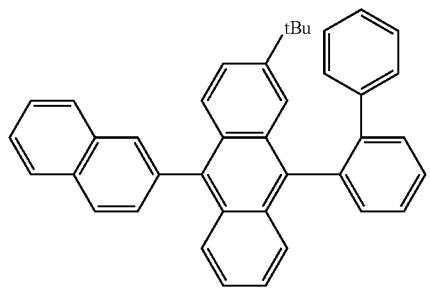
2a'-62
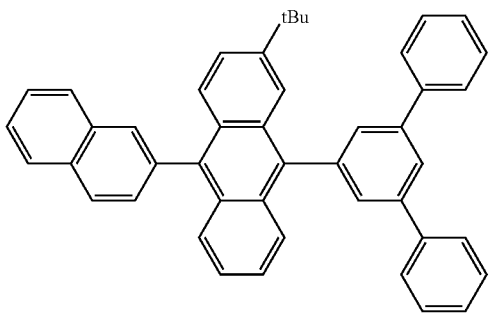
2a'-63
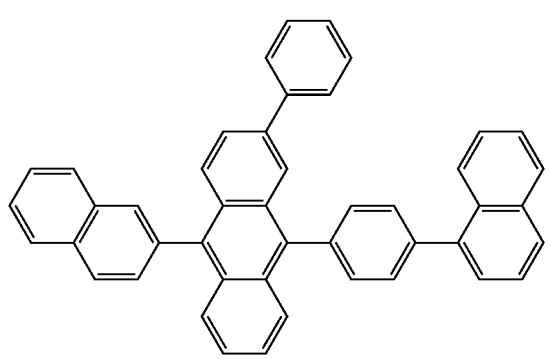
2a'-64
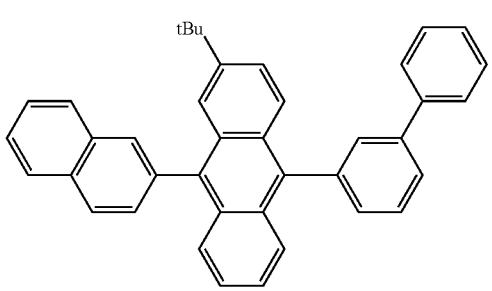
2a'-65
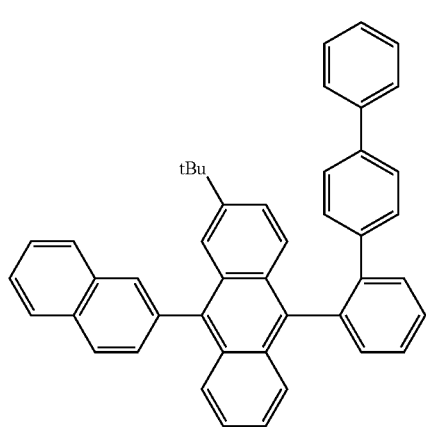
2a'-66
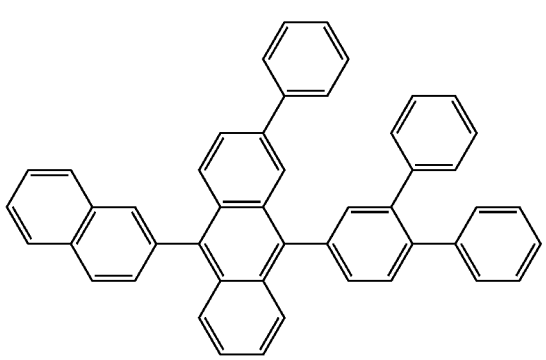

-continued
2a'-67
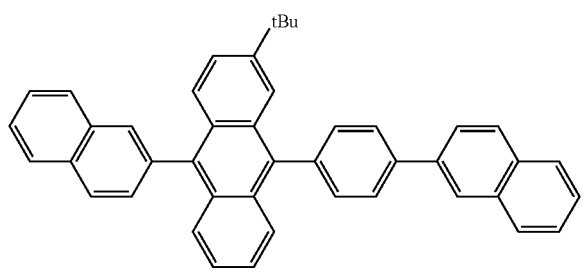
2a'-68
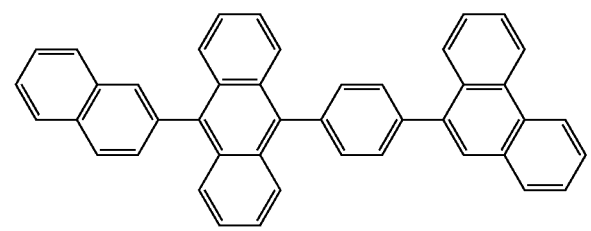
2a'-69
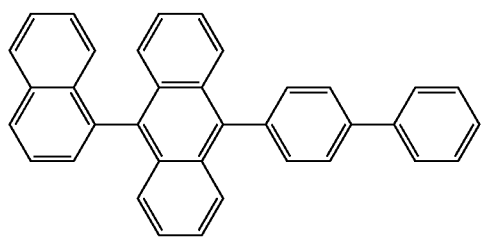
2a'-70
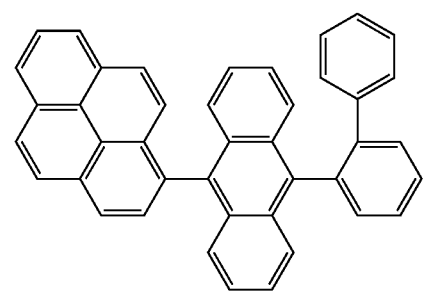
2a'-71
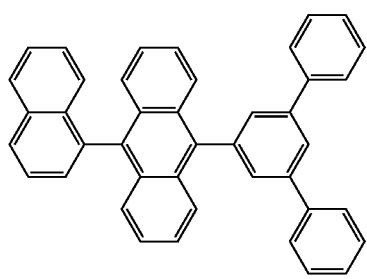
2a'-72
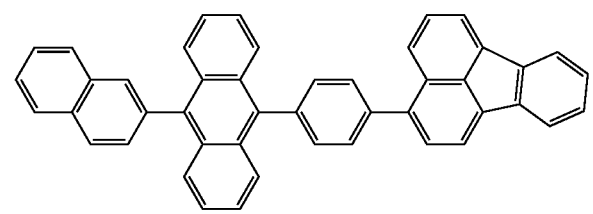
2a'-73
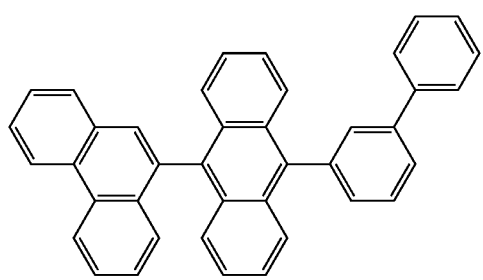
2a'-74
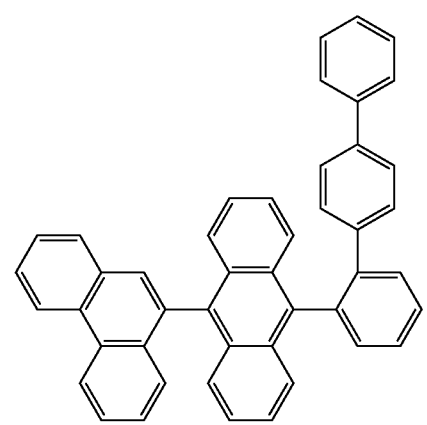

-continued
2a'-75
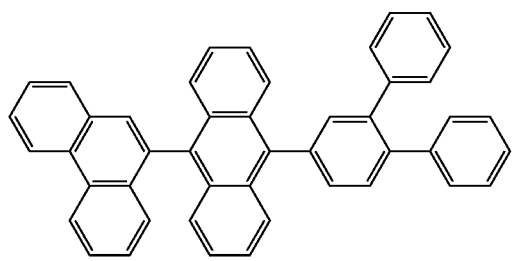
2a'-76
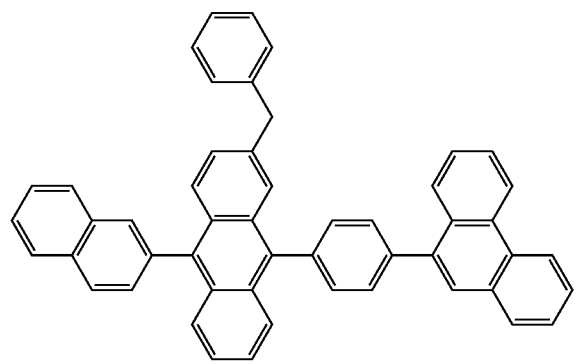
2a'-77
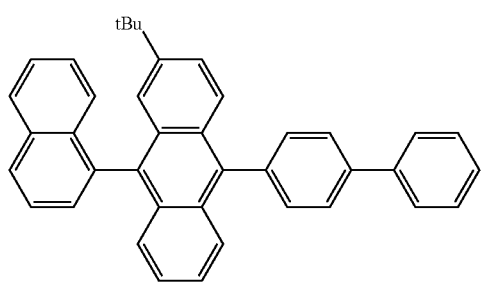
2a'-78
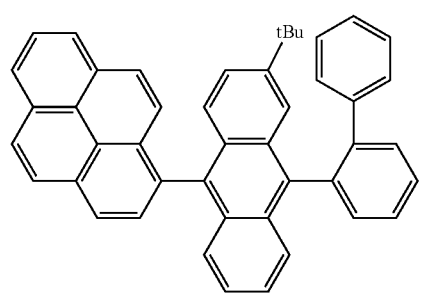
2a'-79
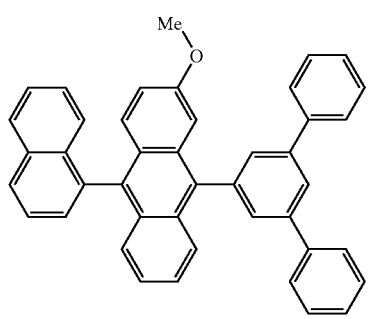
2a'-80
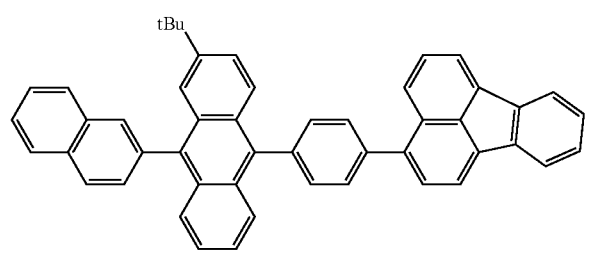
2a'-81
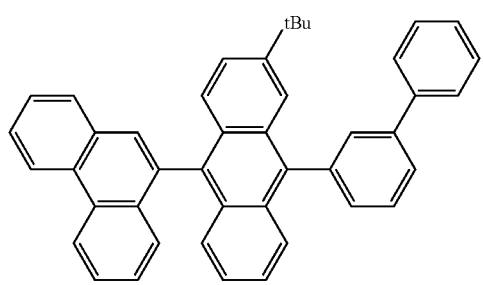
2a'-82
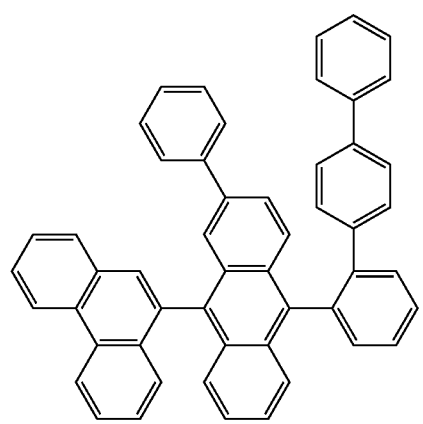

-continued
2a'-83
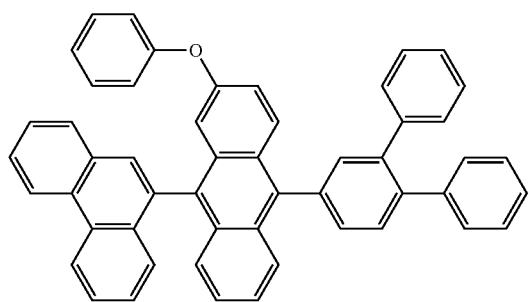
2a'-84
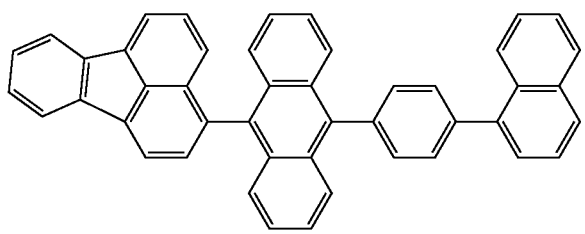
2a'-85
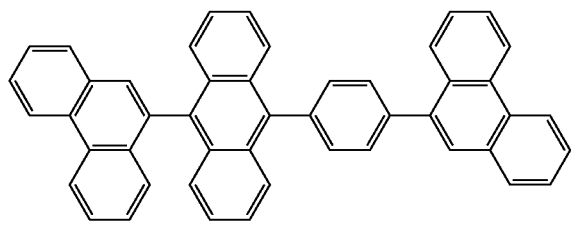
2a'-86
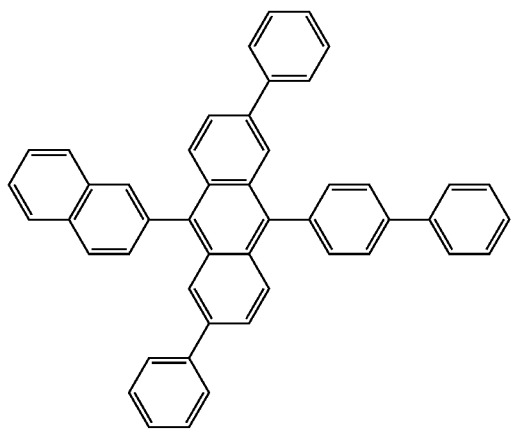
2a'-87
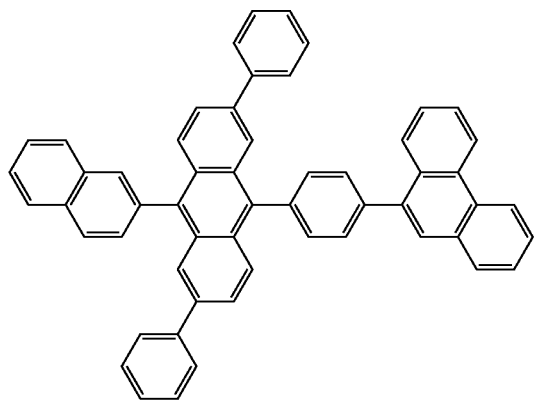
2a'-88
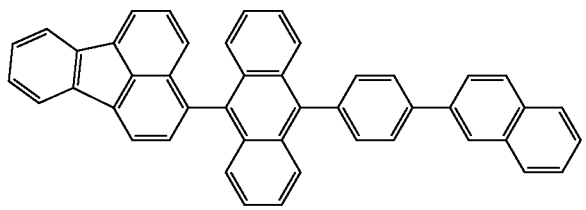
2a'-89
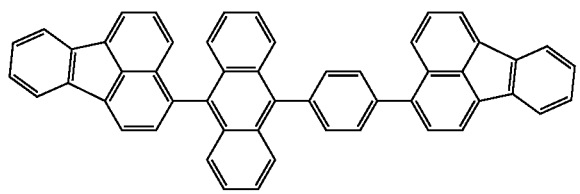
2a'-90
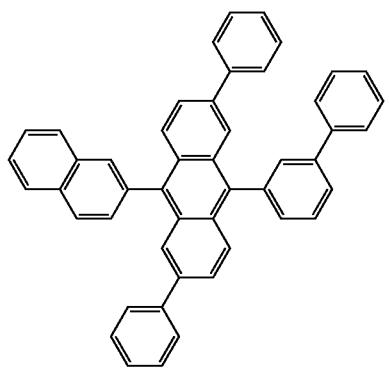

2a′-91
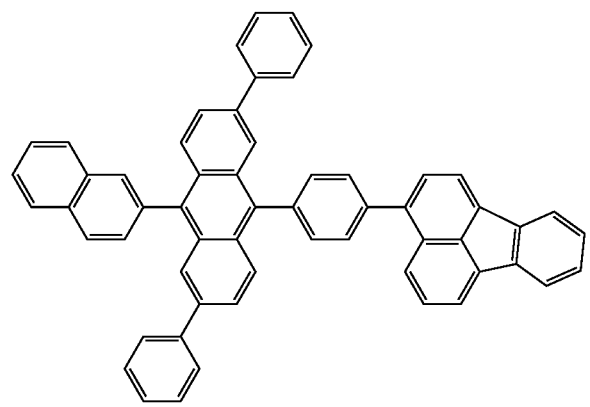
2a′-92
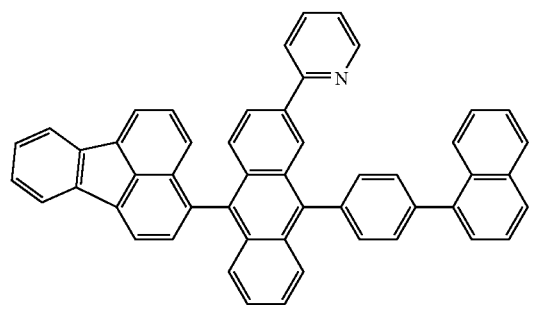
2a′-93
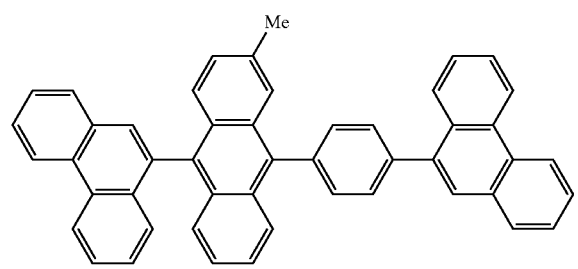
2a′-94
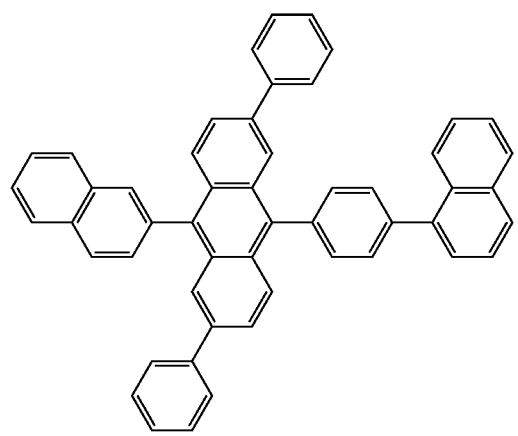
2a′-95
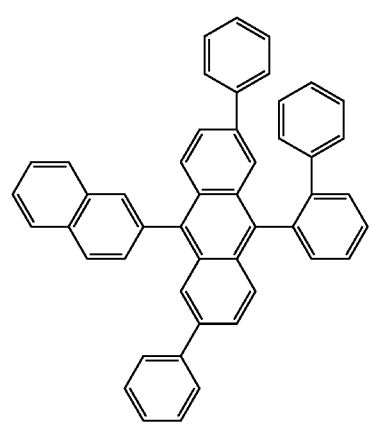
2a′-96
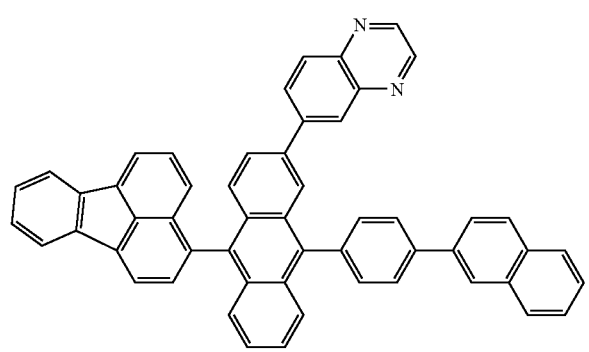

2a'-97
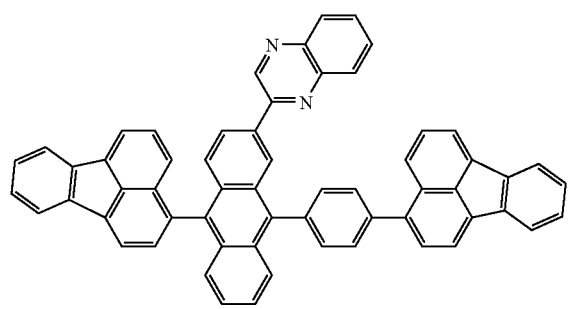
2a'-98
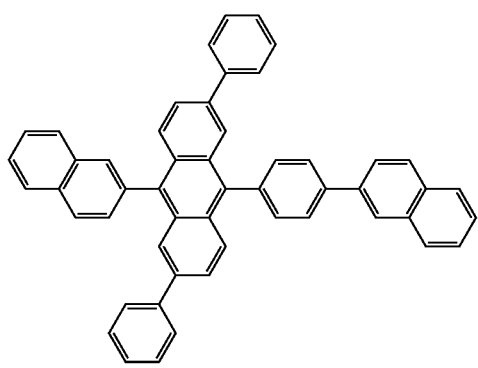
2a'-99
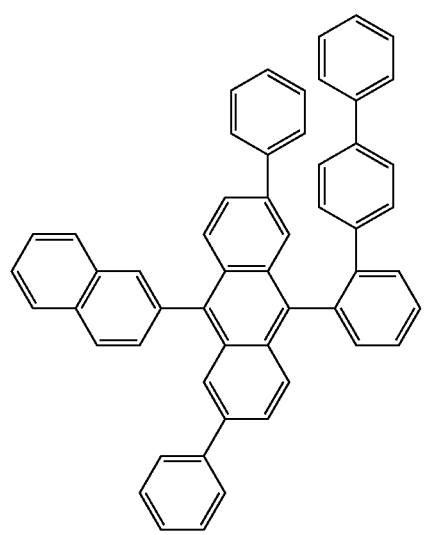
2a'-100
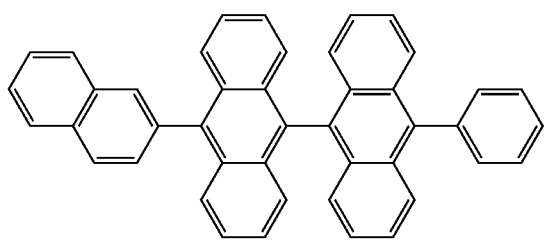
2a'-101
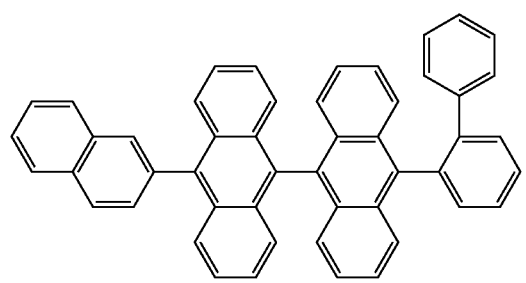
2a'-102
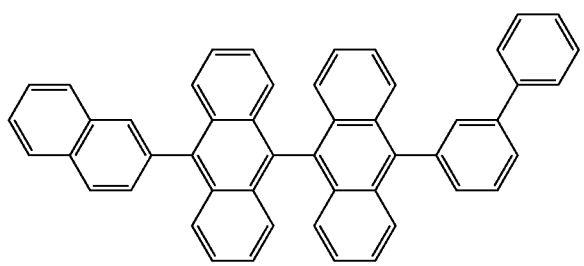
2a'-103
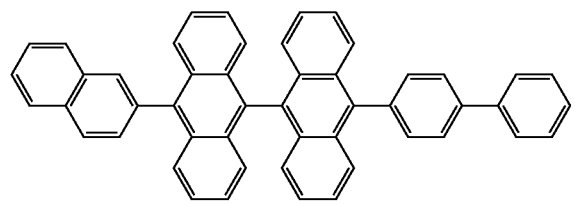
2a'-104
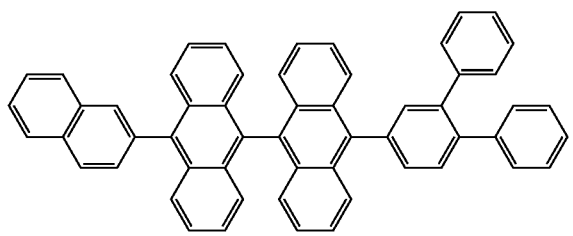

-continued
2a'-105
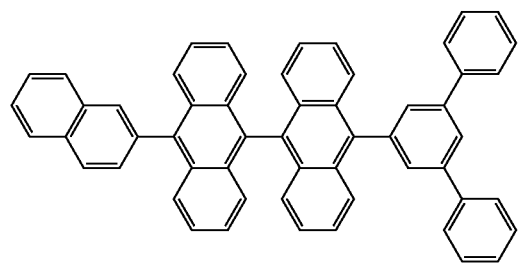
2a'-106
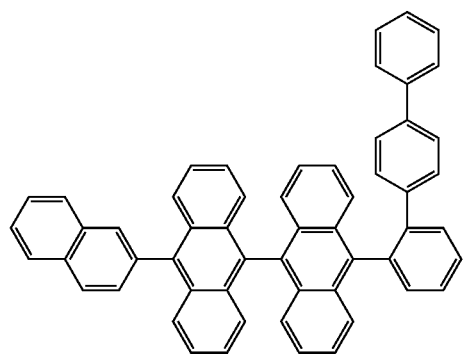
2a'-107
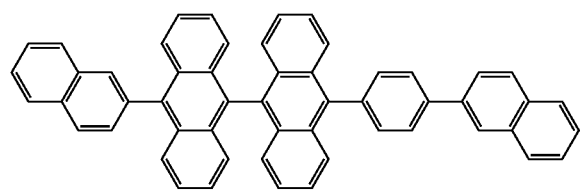
2a'-108
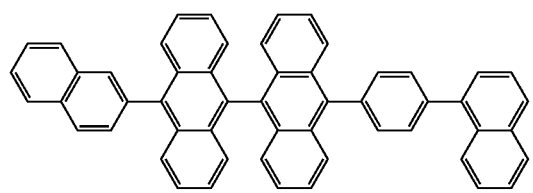
2a'-109
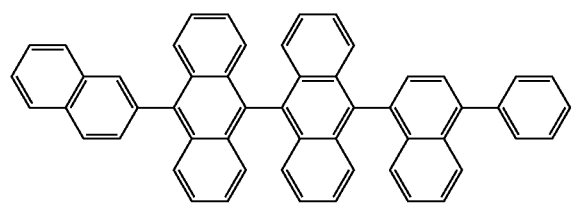
2a'-110
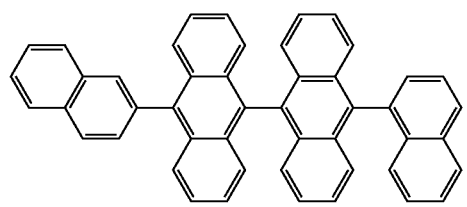
2a'-111
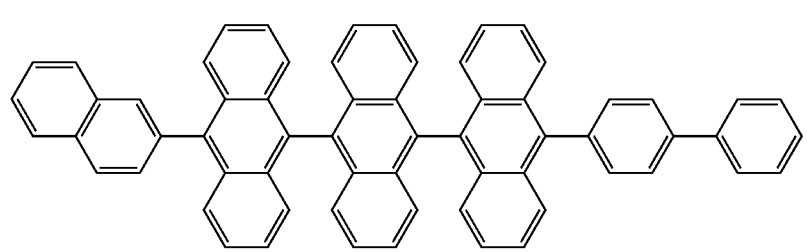
2a'-112
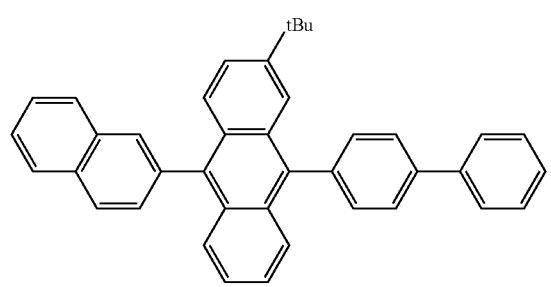
2a'-113
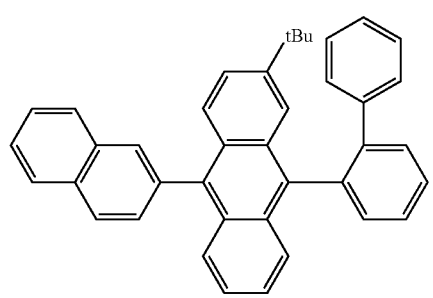

-continued
2a'-114
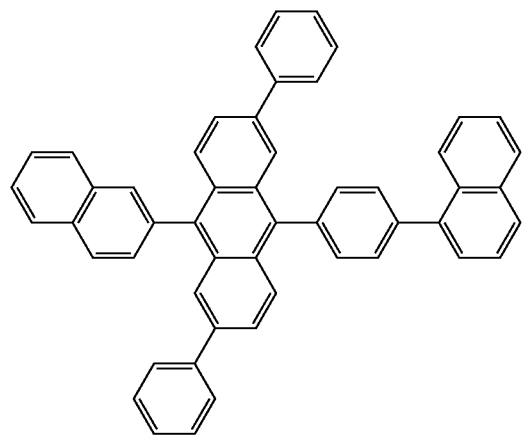
2a'-115
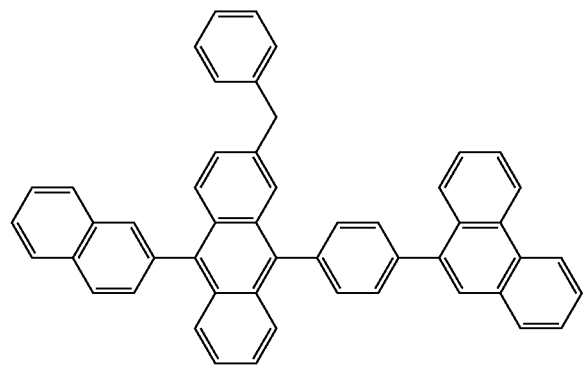
2a'-116
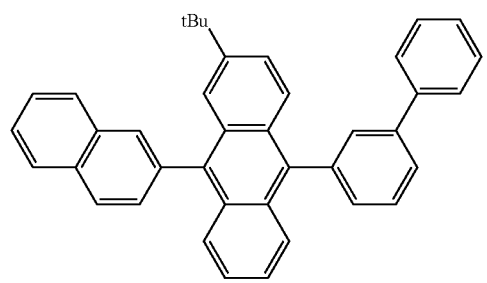
2a'-117
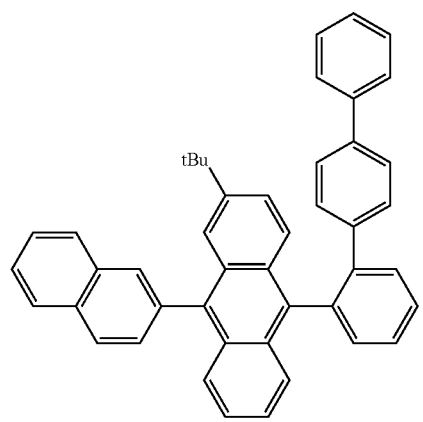
2a'-118
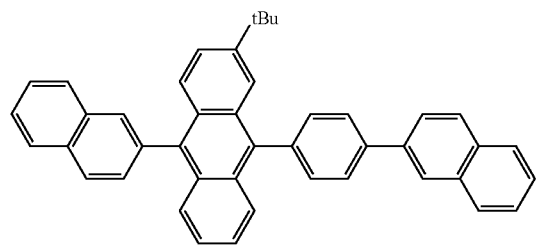
2a'-119
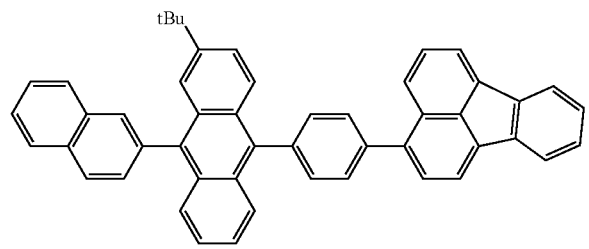
2a'-120
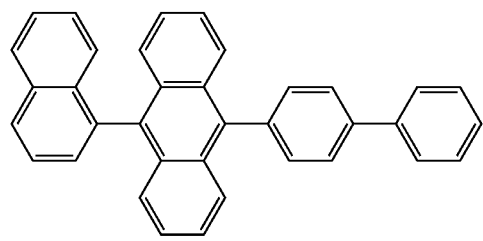
2a'-121
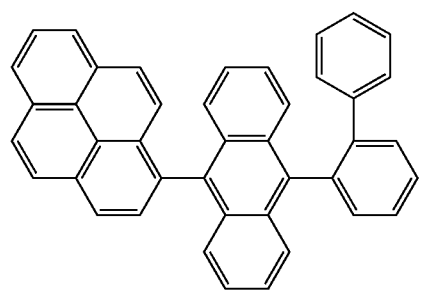

-continued
2a'-122 2a'-123
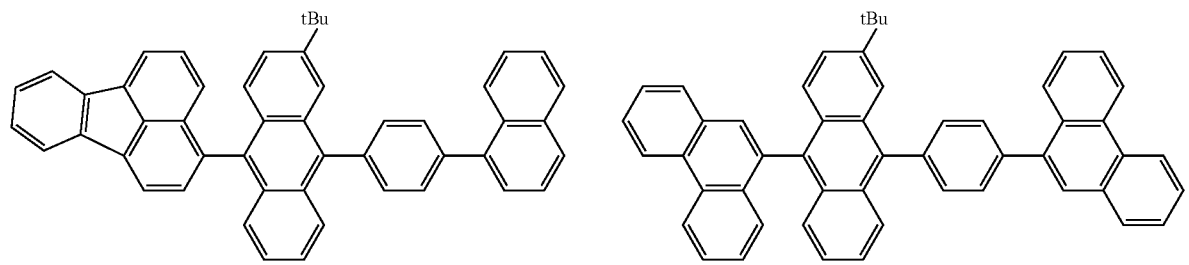
2a'-124 2a'-125
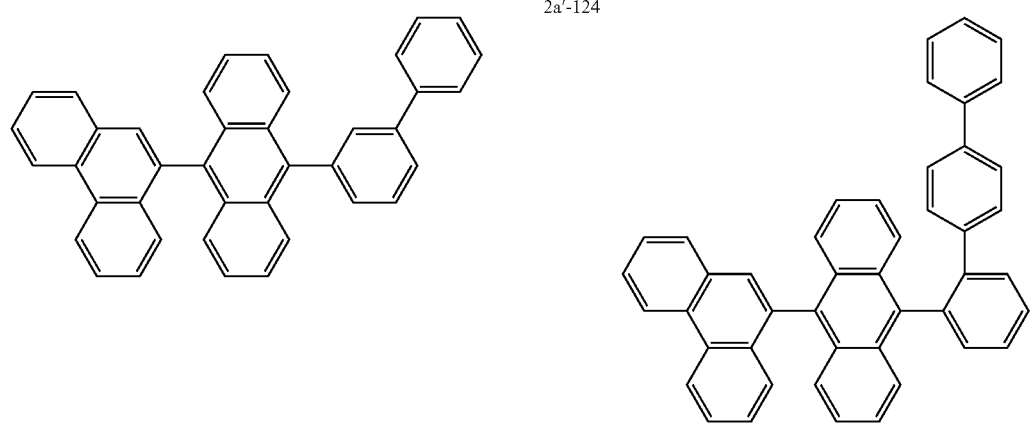
2a'-126 2a'-127
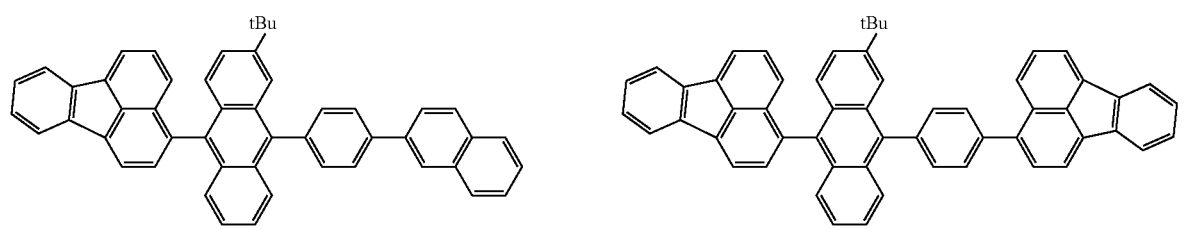
2a'-128 2a'-129
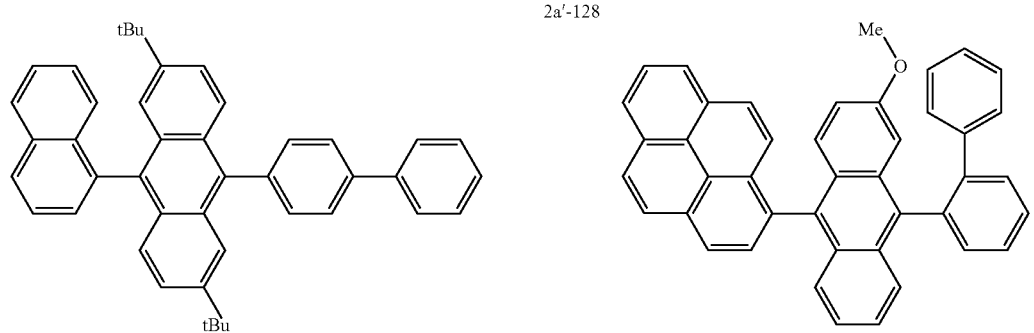
2a'-130 2a'-131
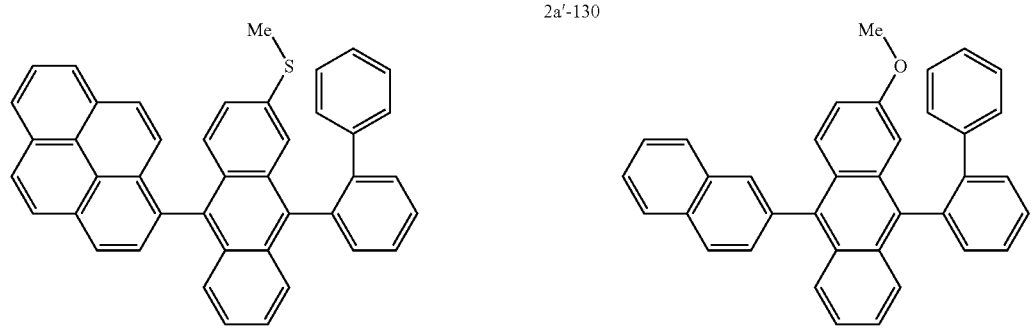

-continued
2a'132
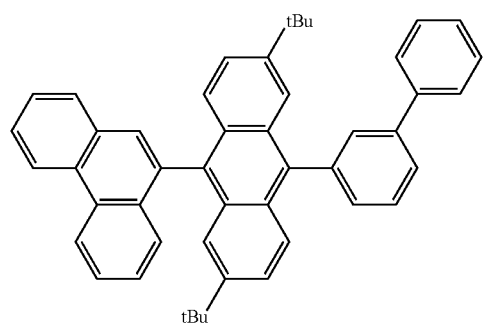
2a'-133
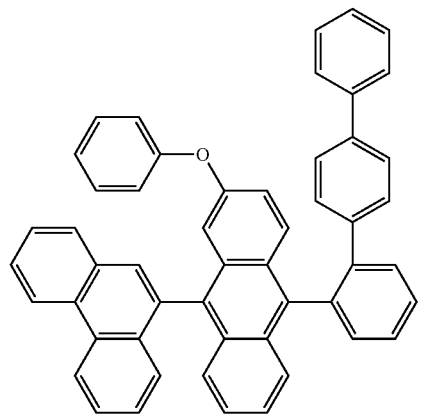
2a'-134
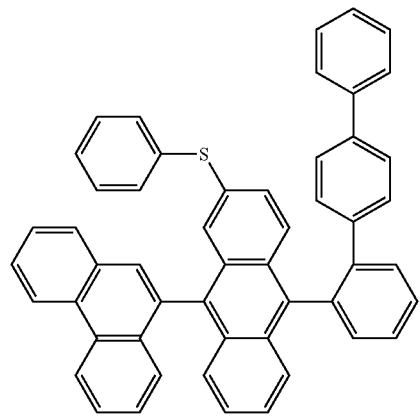
2a'-135
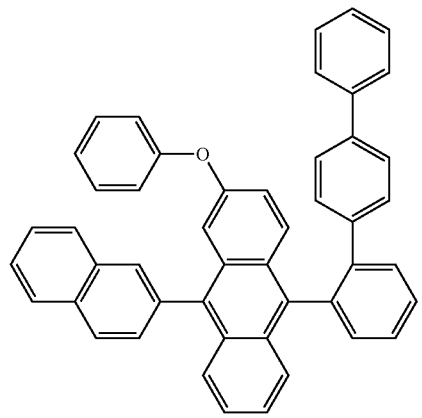
2a'-136
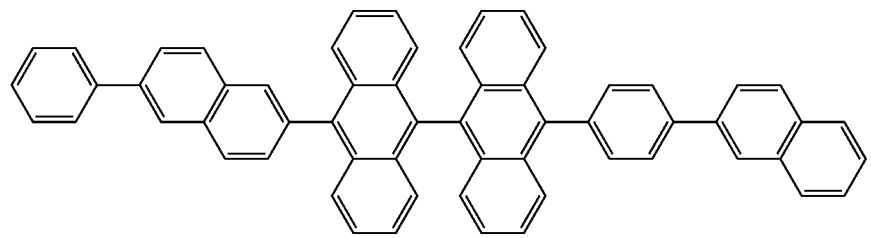
2a'-137
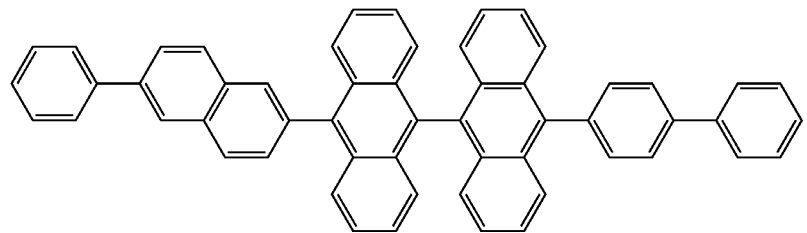
2a'-138
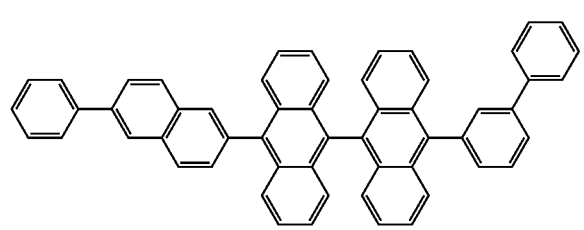
2a'-139
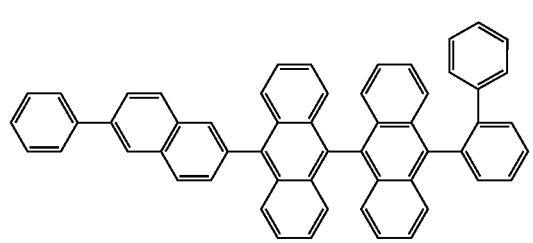

-continued

2a′-140

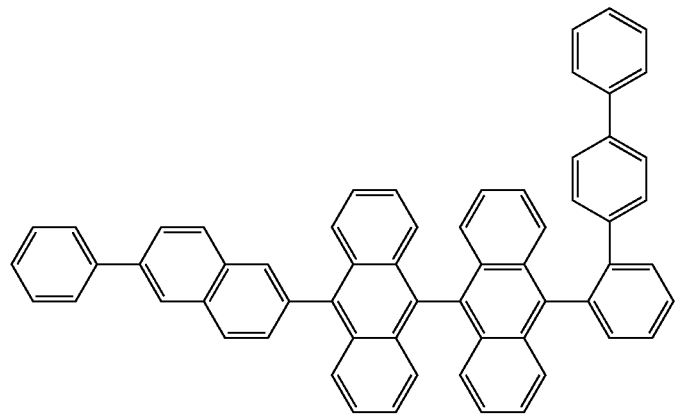

2a′-141

2a′-142

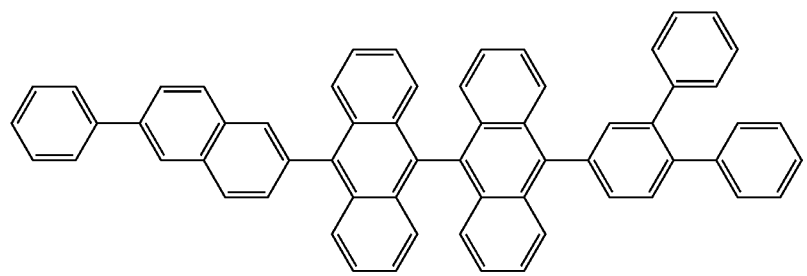

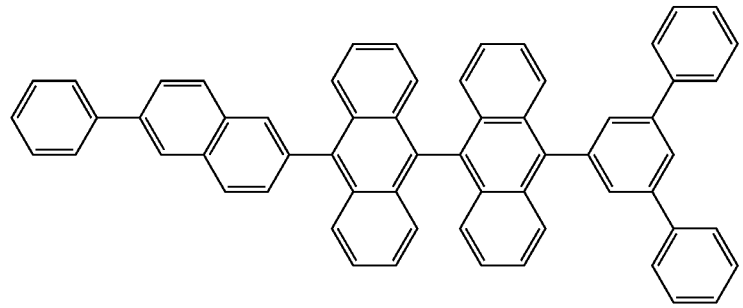

2a′-143

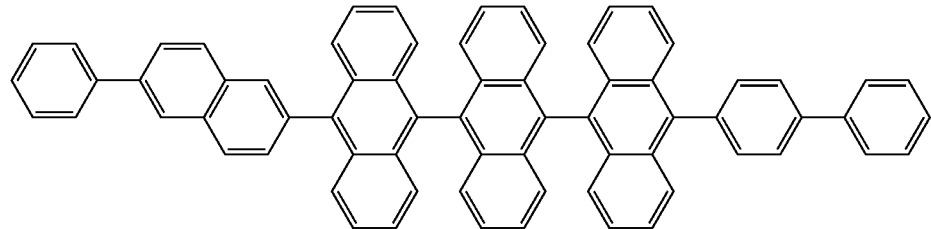

General Formula (2b)

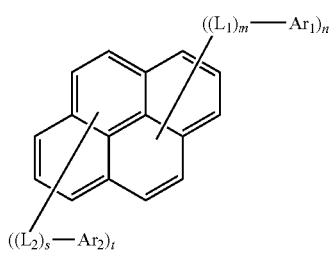

(2b)

where: $Ar_1$ and $Ar_2$ each independently represent a substituted or unsubstituted aryl group having 6 to 50 ring carbon atoms;

$L_1$ and $L_2$ are each independently selected from a substituted or unsubstituted phenylene group, a substituted or unsubstituted naphthalenylene group, a substituted or unsubstituted fluorenylene group, and a substituted or unsubstituted dibenzosilolylene group;

m represents an integer of 0 to 2, n represents an integer of 1 to 4, s represents an integer of 0 to 2, and t represents an integer of 0 to 4; and $L_1$ or $Ar_1$ is bonded to any one of 1- to 5-positions of pyrene, and $L_2$ or $Ar_2$ is bonded to any one of 6- to 10-positions of pyrene.

Examples of the aryl group having 6 to 50 carbon ring atoms represented by $Ar_1$ and $Ar_2$ in the general formula (2b)

include a phenyl group, a 1-naphthyl group, a 2-naphthyl group, a 1-anthryl group, a 2-anthryl group, a 9-anthryl group, a 9-(10-phenyl)anthryl group, a 9-(10-naphthyl-1-yl)anthryl group, a 9-(10-naphthyl-2-yl)anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a 3-methyl-2-napthyl group, a 4-methyl-1-napthyl group, and a 4-methyl-1-anthryl group. The aromatic ring group having 6 to 16 carbon ring atoms is preferred. Especially, a phenyl group, a 1-naphthyl group, a 2-naphthyl group, a 9-(10-phenyl)anthryl group, a 9-(10-naphthyl-1-yl)anthryl group, a 9-(10-naphthyl-2-yl)anthryl group, a 9-phenanthryl group, a 1-pyrenyl group, a 2-pyrenyl group, a 4-pyrenyl group, a 2-biphenylyl group, a 3-biphenylyl group, a 4-biphenylyl group, an o-tolyl group, a m-tolyl group, a p-tolyl group, and a p-t-butylphenyl group.

Further, the alkyl group may be substituted by substituents. Examples of the substituents include an alkyl group (such as a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, and the like); alkoxy groups each having 1 to 6 carbon atoms (such as an ethoxy group, a methoxy group, an i-propoxy group, an n-propoxy group, an s-butoxy group, a t-butoxy group, a pentoxy group, a hexyloxy group, a cyclopentoxy group, and a cyclohexyloxy group); aryl groups each having 5 to 40 ring atoms; amino groups each substituted by an aryl group having 5 to 40 ring atoms; ester groups each having an aryl group having 5 to 40 ring atoms; ester groups each having an alkyl group having 1 to 6 carbon atoms; a cyano group; a nitro group; and a halogen atom.

$L_1$ and $L_2$ in the general formula (2b) are each preferably selected from a substituted or unsubstituted phenylene group, and a substituted or unsubstituted fluorenylene group.

In addition, examples of a substituent for each of $L_1$ and $L_2$ include examples similar to those described for the aromatic group.

m in the general formula (2b) preferably represents an integer of 0 or 1. n in the general formula (2b) preferably represents an integer of 1 or 2. s in the general formula (2b) preferably represents an integer of 0 or 1.

t in the general formula (2b) preferably represents an integer of 0 to 2.

Specific examples of the pyrene derivative represented by the general formula (2b) to be used in the organic EL device of the present invention include asymmetric pyrene described in paragraphs [0020] to [0023] of WO 2005/115950. Alternatively, symmetric pyrene can be used as a material for the organic EL device of the present invention. Representative specific examples are shown below:

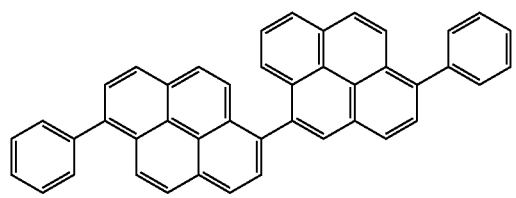

2b-1

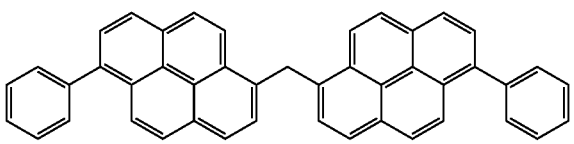

2b-2

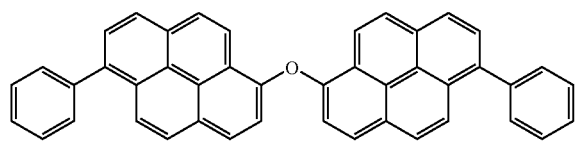

2b-3

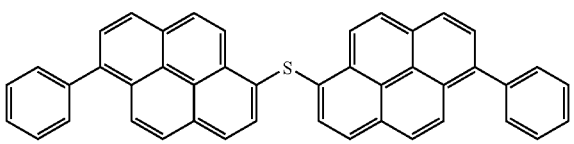

2b-4

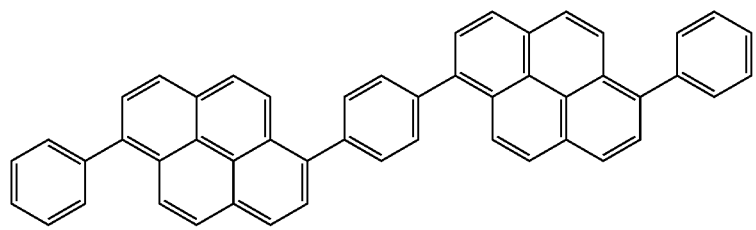
2b-5
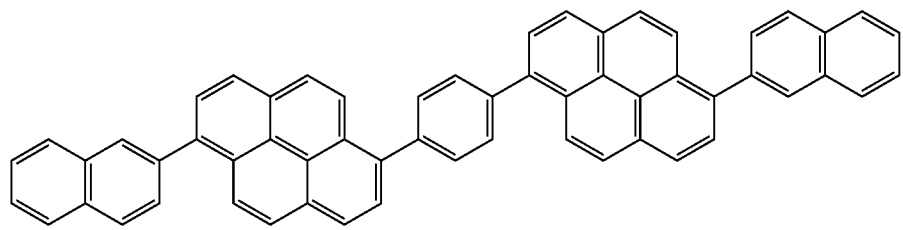
2b-6
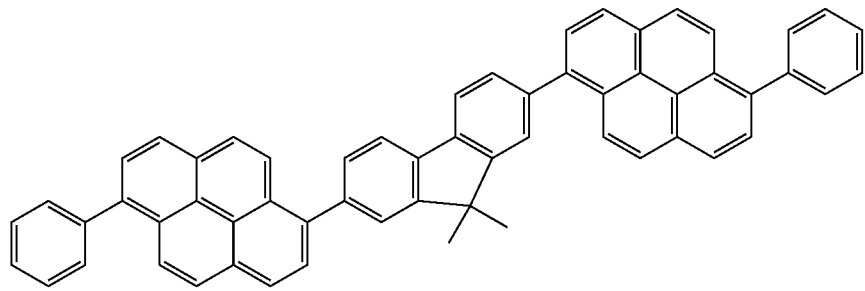
2b-7
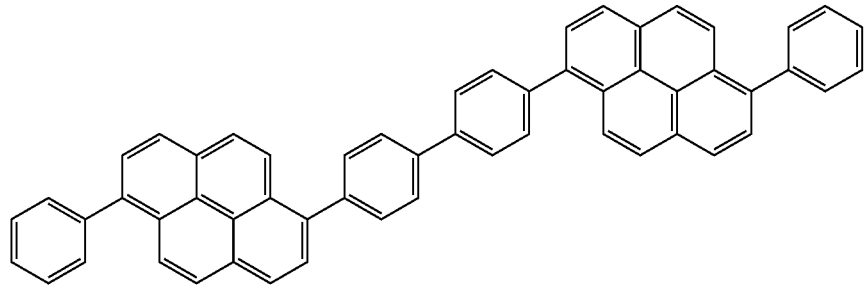
2b-8
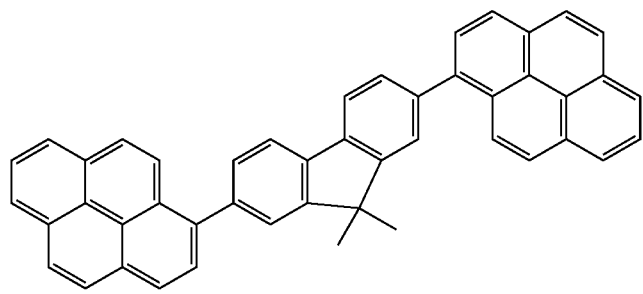
2b-9
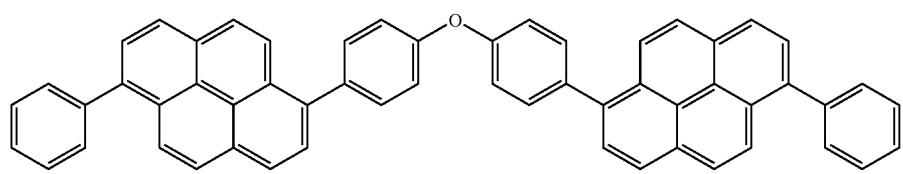
2b-10

-continued
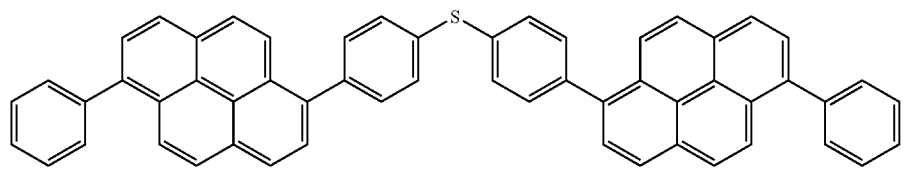
2b-11
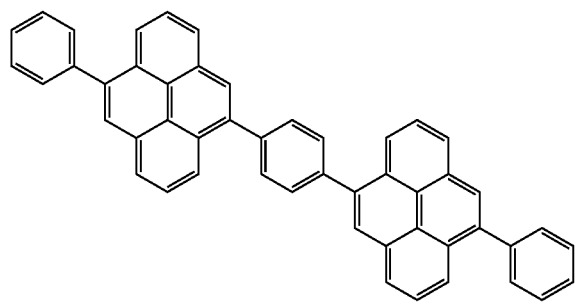
2b-12
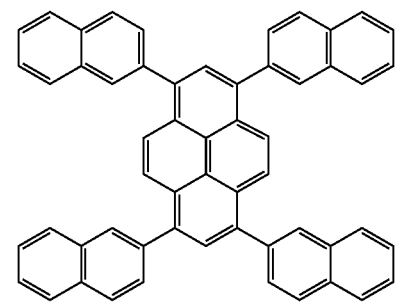
2b-13
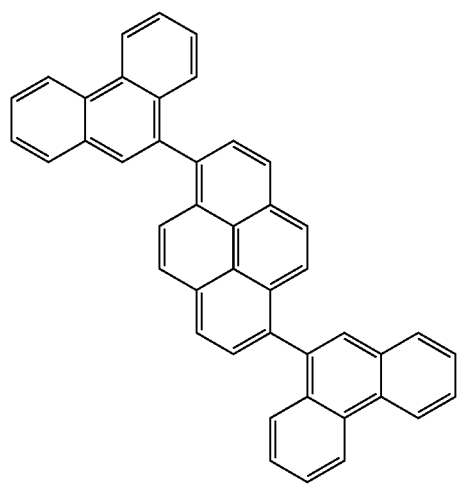
2b-14
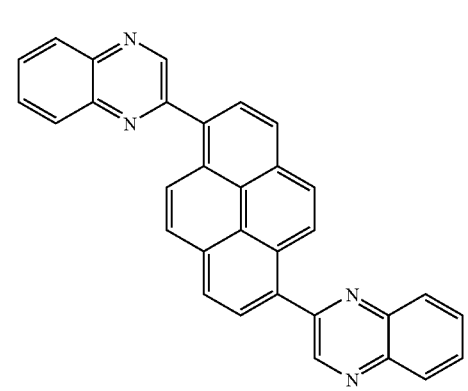
2b-15
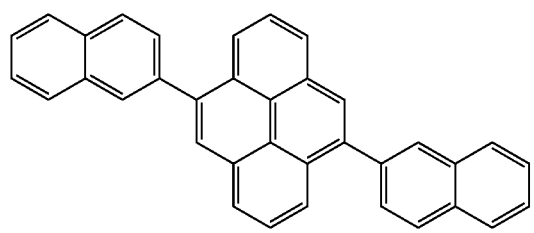
2b-16
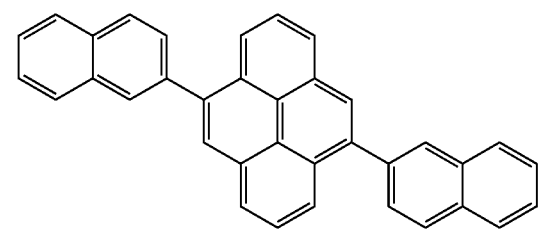
2b-17
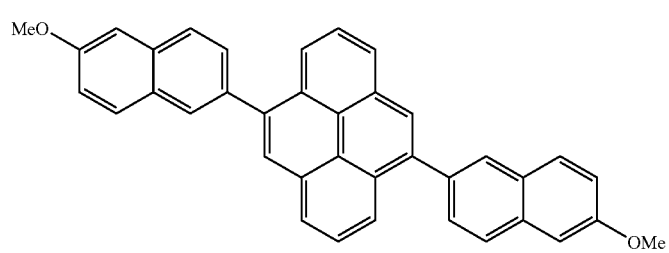
2b-18

2b-19
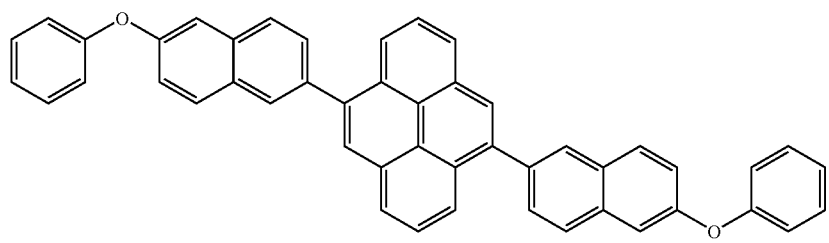
2b-20
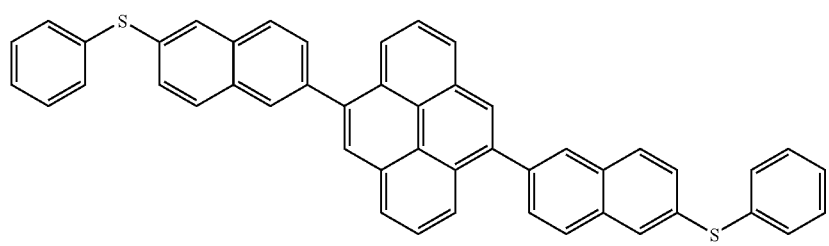
2b-21
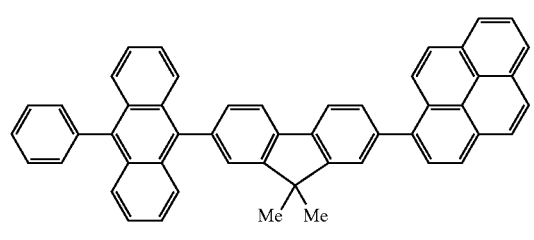
2b-22
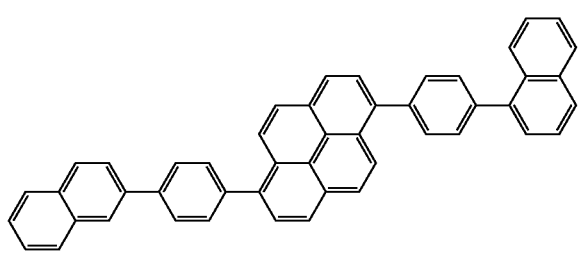
2b-23
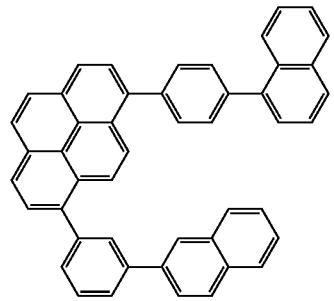
2b-24
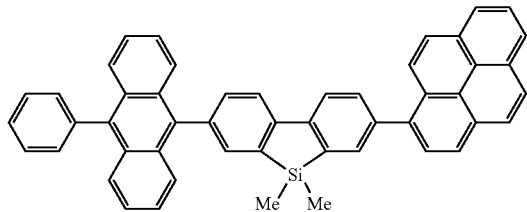
2b-25
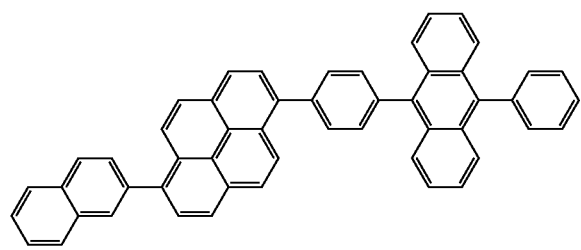
2b-26
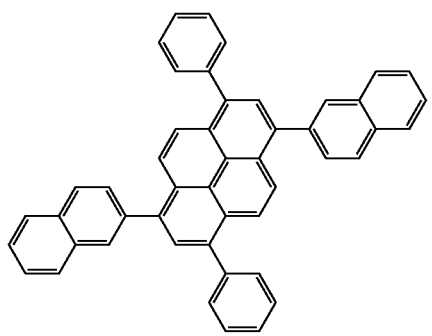

-continued
2b-27
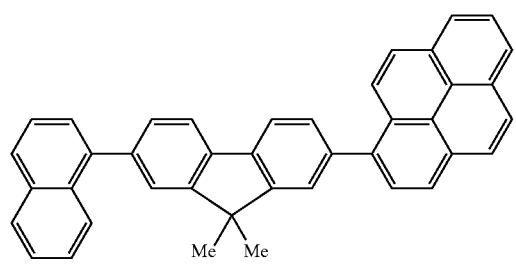
2b-28
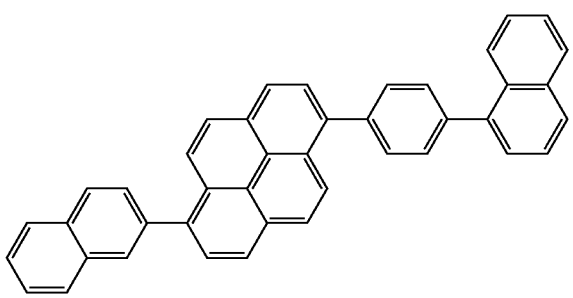
2b-29
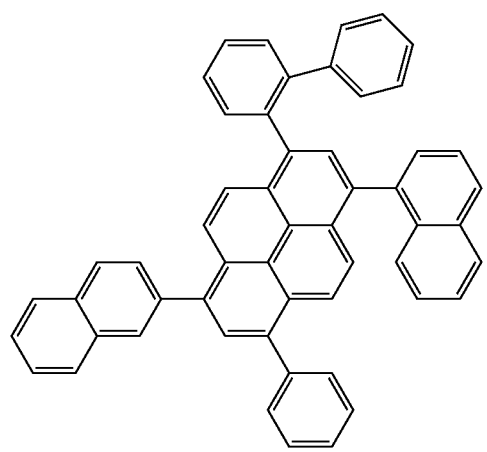
2b-30
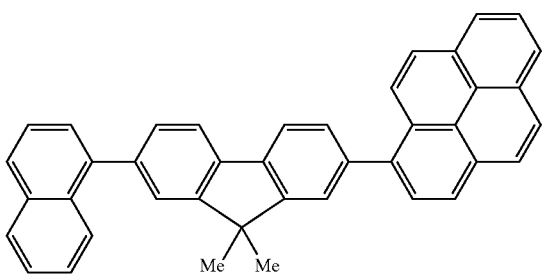
2b-31
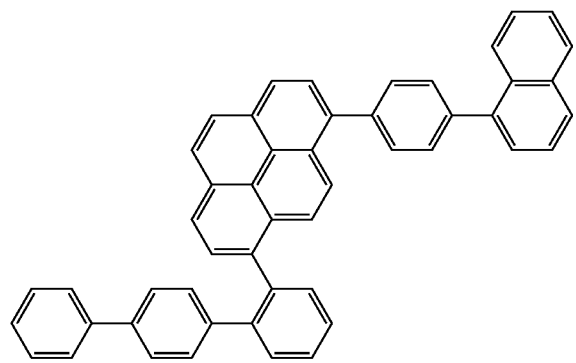
2b-32
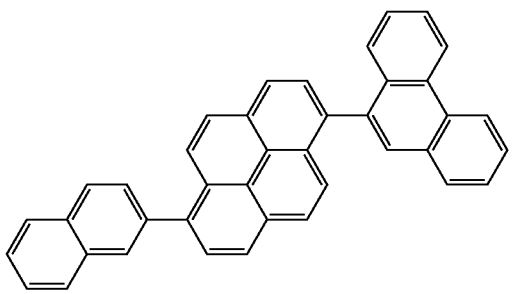
2b-33
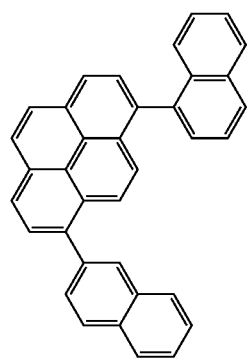
2b-34
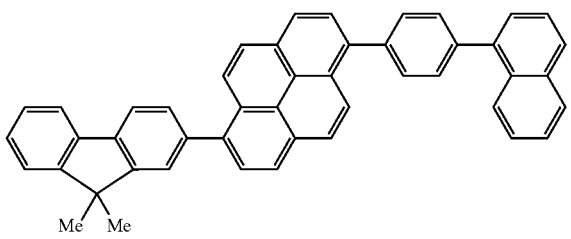

-continued 2b-35
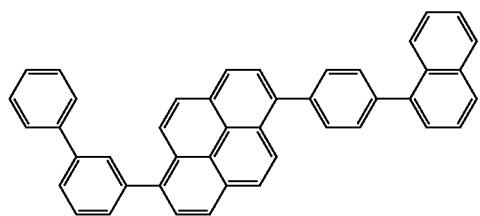

2b-36
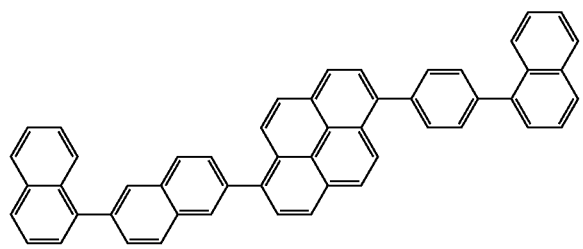

2b-37
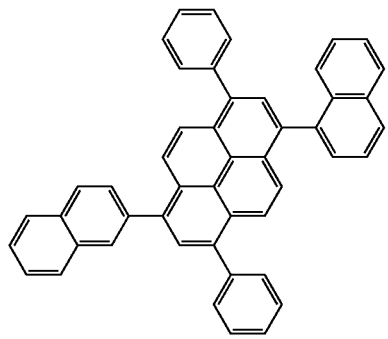

2b-38
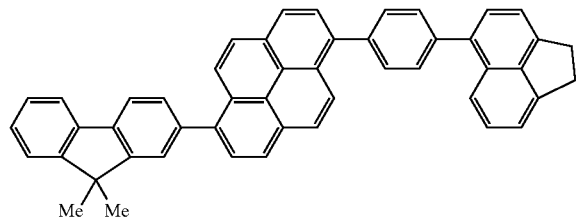

2b-39
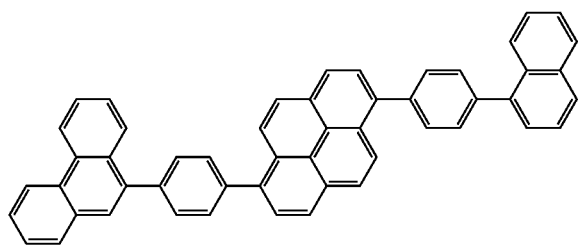

2b-40
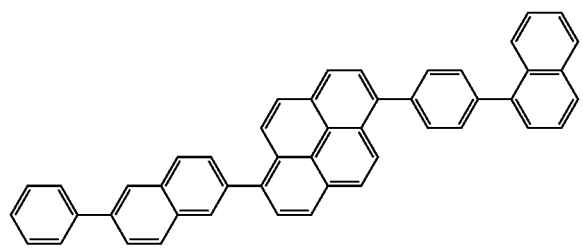

2b-41
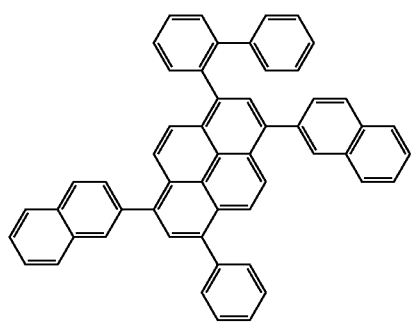

2b-42
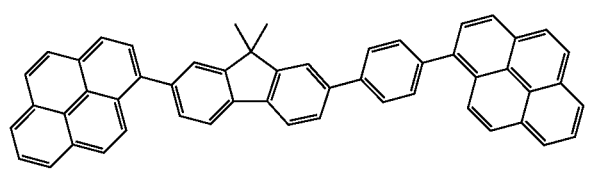

General Formula (2c)

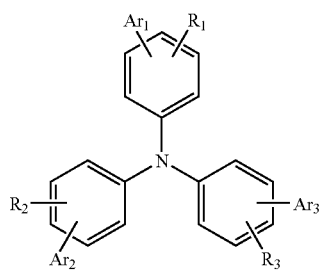

(2c)

where: $Ar_1$, $Ar_2$, and $Ar_3$ are each independently selected from a group having an anthracene structure, a group having a phenanthrene structure, and a group having a pyrene structure; and $R_1$, $R_2$, and $R_3$ each independently represent a hydrogen atom or a substituent.

$Ar_1$, $Ar_2$, and $Ar_3$ in the general formula (2c) are each chosen from preferably a substituted or unsubstituted anthrylphenyl group, an anthryl group, a phenanthrenyl group, a perylenyl group, and a pyrenyl group, more preferably an alkyl-substituted or unsubstituted anthrylphenyl group, a phenanthryl group, and a pyrenyl group, or particularly preferably a pyrenyl group and a phenanthryl group.

Examples of any one of $R_1$, $R_2$, and $R_3$ in the general formula (2c) include: a hydrogen atom; an alkyl group (having preferably 1 to 30, more preferably 1 to 20, or particularly preferably 1 to 10 carbon atoms such as a methyl, ethyl, isopropyl, t-butyl, n-octyl, n-decyl, n-hexadecyl, cyclopropyl, cyclopentyl, or cyclohexyl group); an alkenyl group (having preferably 2 to 30, more preferably 2 to 20, or particularly preferably 2 to 10 carbon atoms such as a vinyl, allyl, 2-butenyl, or 3-pentenyl group); an alkynyl group (having preferably 2 to 30, more preferably 2 to 20, or particularly preferably 2 to 10 carbon atoms such as a propargyl or 3-pentynyl group), an aryl group (having preferably 6 to 30, more preferably 6 to 20, or particularly preferably 6 to 12 carbon atoms, such as phenyl, p-methylphenyl, naphthyl, or anthranyl); an amino group (having preferably 0 to 30, more preferably 0 to 20, or particularly preferably 0 to 10 carbon atoms, such as amino, methylamino, dimethylamino, diethylamino, dibenzylamino, diphenylamino, or ditolylamino); an alkoxy group (having preferably 1 to 30, more preferably 1 to 20, or particularly preferably 1 to 10 carbon atoms, such as methoxy, ethoxy, butoxy, or 2-ethylhexyloxy); an aryloxy group (having preferably 6 to 30, more preferably 6 to 20, or particularly preferably 6 to 12 carbon atoms, such as phenyloxy, 1-naphthyloxy, or 2-naphthyloxy); an heteroaryloxy group (having preferably 1 to 30, more preferably 1 to 20, or particularly preferably 1 to 12 carbon atoms, such as pyridyloxy, pyradyloxy, pyrimidyloxy, or quinolyloxy); an acyl group (having preferably 1 to 30, more preferably 1 to 20, or particularly preferably 1 to 12 carbon atoms, such as acetyl, benzoyl, formyl, or pivaloyl); an alkoxycarbonyl group (having preferably 2 to 30, more preferably 2 to 20, or particularly preferably 2 to 12 carbon atoms, such as methoxycarbonyl or ethoxycarbonyl); an aryloxycarbonyl group (having preferably 7 to 30, more preferably 7 to 20, or particularly preferably 7 to 12 carbon atoms, such as phenyloxycarbonyl); an acyloxy group (having preferably 2 to 30, more preferably 2 to 20, or particularly preferably 2 to 10 carbon atoms, such as acetoxy or benzoyloxy); an acylamino group (having preferably 2 to 30, more preferably 2 to 20, or particularly preferably 2 to 10 carbon atoms, such as acetylamino or benzoylamino); an alkoxycarbonylamino group (having preferably 2 to 30, more preferably 2 to 20, or particularly preferably 2 to 12 carbon atoms, such as methoxycarbonylamino); an aryloxycarbonylamino group (having preferably 7 to 30, more preferably 7 to 20, or particularly preferably 7 to 12 carbon atoms, such as phenyloxycarbonylamino); a sulfonylamino group (having preferably 1 to 30, more preferably 1 to 20, or particularly preferably 1 to 12 carbon atoms, such as methane sulfonylamino or benzene sulfonylamino); a sulfamoyl group (having preferably 0 to 30, more preferably 0 to 20, or particularly preferably 0 to 12 carbon atoms, such as sulfamoyl, methylsulfamoyl, dimethylsulfamoyl, or phenylsulfamoyl); a carbamoyl group (having preferably 1 to 30, more preferably 1 to 20, or particularly preferably 1 to 12 carbon atoms, such as carbamoyl, methylcarbamoyl, diethylcarbamoyl, or phenylcarbamoyl); an alkylthio group (having preferably 1 to 30, more preferably 1 to 20, or particularly preferably 1 to 12 carbon atoms, such as methylthio or ethylthio); an arylthio group (having preferably 6 to 30, more preferably 6 to 20, or particularly preferably 6 to 12 carbon atoms, such as a phenylthio group); a heteroarylthio group (having preferably 1 to 30, more preferably 1 to 20, or particularly preferably 1 to 12 carbon atoms, such as pyridylthio, 2-benzoimizolylthio, 2-benzoxazolylthio, or 2-benzthiazolylthio); a sulfonyl group (having preferably 1 to 30, more preferably 1 to 20, or particularly preferably 1 to 12 carbon atoms, such as mesyl or tosyl); a sulfinyl group (having preferably 1 to 30, more preferably 1 to 20, or particularly preferably 1 to 12 carbon atoms, such as methanesulfinyl or benzenesulfinyl); a ureido group (having preferably 1 to 30, more preferably 1 to 20, or particularly preferably 1 to 12 carbon atoms, such as ureido, methylureido, or phenylureido); a phosphoric amide group (having preferably 1 to 30, more preferably 1 to 20, or particularly preferably 1 to 12 carbon atoms, such as diethylphosphoric amide or phenylphosphoric amide); a hydroxyl group; a mercapto group; a halogen atom (such as a fluorine atom, a chlorine atom, a bromine atom, or an iodine atom); a cyano group; a sulfo group; a carboxyl group; a nitro group; a hydroxamic group; a sulfino group; a hydrazino group; an imino group; and a heterocyclic group (having preferably 1 to 30, or more preferably 1 to 12 carbon atoms and containing, as a hetero atom, a nitrogen atom, an oxygen atom, or a sulfur atom, specifically an imidazolyl, pyridyl, quinolyl, furyl, thienyl, piperidyl, morpholino, benzoxazolyl, benzimidazolyl, benzothiazolyl, or the like); and a silyl group (having preferably 3 to 40, more preferably 3 to 30, or particularly preferably 3 to 24 carbon atoms, such as a trimethylsilyl group or a triphenylsilyl group). Each of those substituents may be additionally substituted.

The substituents $R^1$, $R^2$, and $R^3$ in the general formula (2c) are each preferably selected from an alkyl group and an aryl group.

Specific examples of the amine derivative represented by the general formula (2c) to be used in the organic EL device of the present invention include various known amine derivatives such as an amine derivative described in paragraphs [0079] to [0083] of Japanese Patent Application Laid-Open No. 2002-324678. Representative specific examples are shown below:

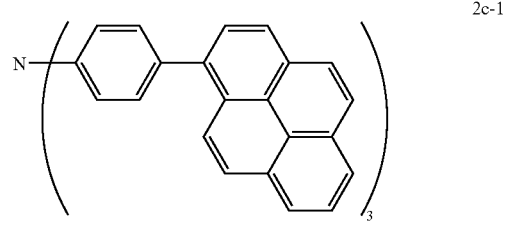

2c-1

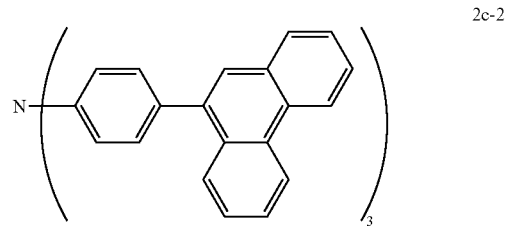

2c-2

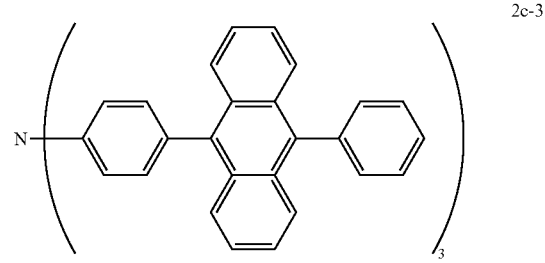

2c-3

-continued
2c-4
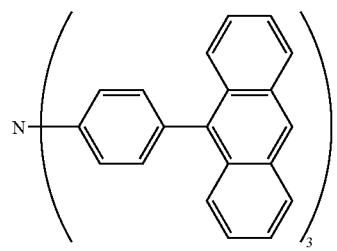
2c-5
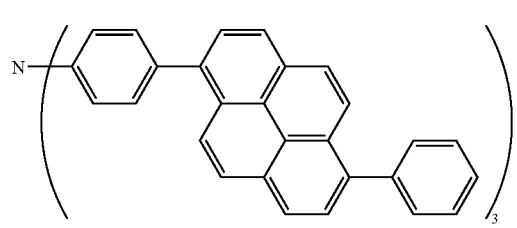
2c-6
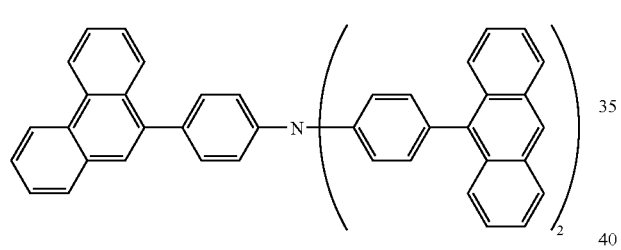
2c-8
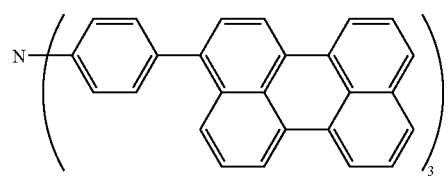
2c-10
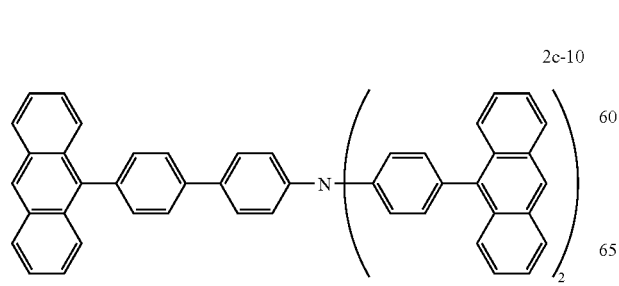
-continued
2c-11
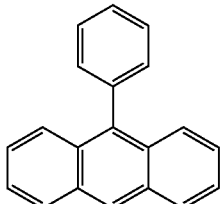
2c-12
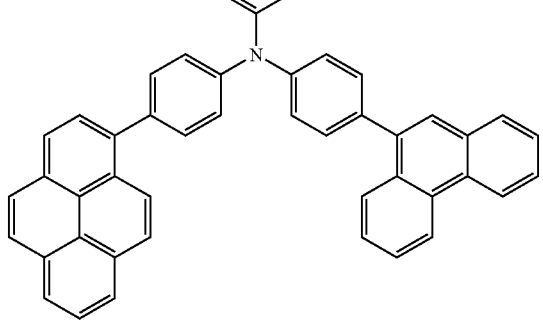
2c-13
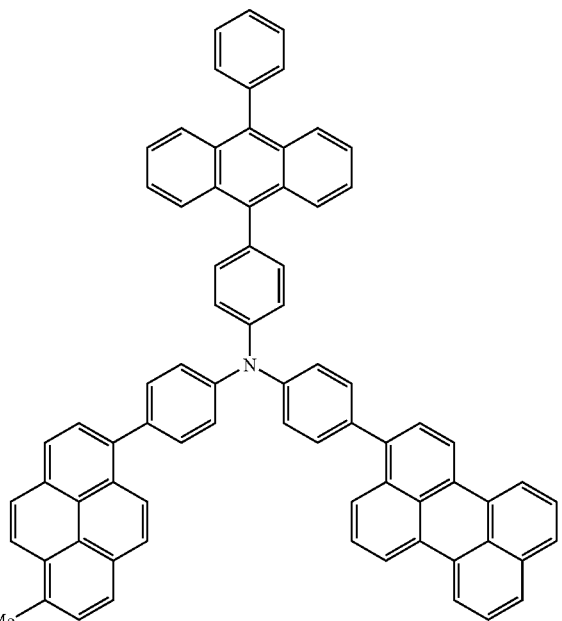

-continued

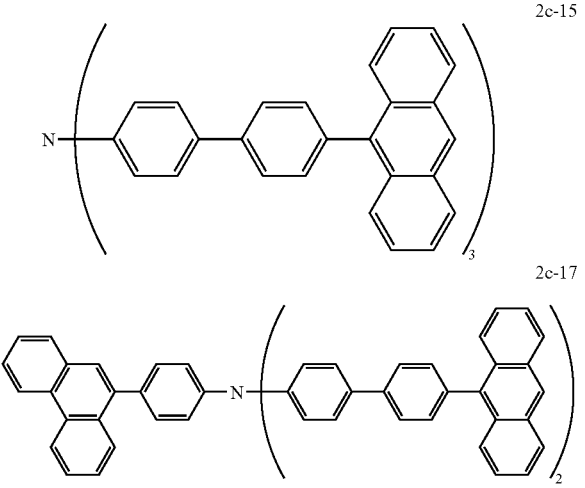

General Formula (2d)

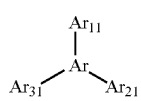
(2d)

where: $Ar_{11}$, $Ar_{21}$, and $Ar_{31}$ each independently represent an aryl group having 6 to 50 ring carbon atoms, and the aryl group may be substituted by at least one substituent;

at least one of $Ar_{11}$, $Ar_{21}$, $Ar_{31}$, and substituents possessed by these aryl groups has a fused ring aryl structure having 10 to 20 ring carbon atoms, or a fused ring heteroaryl structure having 6 to 20 ring carbon atoms; and Ar represents a trivalent group derived from an aromatic ring or from a heterocyclic aromatic ring.

The aryl group having 6 to 50 ring carbon atoms represented by any one of $Ar_{11}$, $Ar_{21}$, and $Ar^{31}$ in the general formula (2d) has preferably 6 to 30, more preferably 6 to 20, or still more preferably 6 to 16 ring carbon atoms. Examples of the aryl group include a phenyl group, a naphthyl group, an anthryl group, a phenanthrenyl group, a pyrenyl group, a perylenyl group, a fluorenyl group, a biphenylyl group, a terphenylyl group, a rubrenyl group, a chrysenyl group, a triphenylenyl group, a benzoanthryl group, a benzophenanthrenyl group, and a diphenylanthryl group. Each of those aryl groups may additionally have a substituent.

Examples of the substituent in aryl groups include: an alkyl group (having preferably 1 to 30, more preferably 1 to 20, or particularly preferably 1 to 10 carbon atoms, such as methyl, ethyl, isopropyl, t-butyl, n-octyl, n-decyl, n-hexadecyl, cyclopropyl, cyclopentyl, or cyclohexyl); an alkenyl group (having preferably 2 to 30, more preferably 2 to 20, or particularly preferably 2 to 10 carbon atoms, such as vinyl, allyl, 2-butenyl, or 3-pentenyl); an alkynyl group (having preferably 2 to 30, more preferably 2 to 20, or particularly preferably 2 to 10 carbon atoms, such as propargyl or 3-pentynyl); an aryl group (having preferably 6 to 30, more preferably 6 to 20, or particularly preferably 6 to 12 carbon atoms, such as phenyl, p-methylphenyl, naphthyl, or anthranyl); an amino group (having preferably 0 to 30, more preferably 0 to 20, or particularly preferably 0 to 10 carbon atoms, such as amino, methylamino, dimethylamino, diethylamino, dibenzylamino, diphenylamino, or ditolylamino); an alkoxy group (having preferably 1 to 30, more preferably 1 to 20, or particularly preferably 1 to 10 carbon atoms, such as methoxy, ethoxy, butoxy, or 2-ethylhexyloxy); an aryloxy group (having preferably 6 to 30, more preferably 6 to 20, or particularly preferably 6 to 12 carbon atoms, such as phenyloxy, 1-naphthyloxy, or 2-naphthyloxy); a heteroaryloxy group (having preferably 1 to 30, more preferably 1 to 20, or particularly preferably 1 to 12 carbon atoms, such as pyridyloxy, pyradyloxy, pyrimidyloxy, or quinolyloxy); an acyl group (having preferably 1 to 30, more preferably 1 to 20, or particularly preferably 1 to 12-carbon atoms, such as acetyl, benzoyl, formyl, or pivaloyl); an alkoxycarbonyl group (having preferably 2 to 30, more preferably 2 to 20, or particularly preferably 2 to 12 carbon atoms, such as methoxycarbonyl or ethoxycarbonyl); an aryloxycarbonyl group (having preferably 7 to 30, more preferably 7 to 20, or particularly preferably 7 to 12 carbon atoms, such as phenyloxycarbonyl); an acyloxy group (having preferably 2 to 30, more preferably 2 to 20, or particularly preferably 2 to 10 carbon atoms, such as acetoxy or benzoyloxy); an acylamino group (having preferably 2 to 30, more preferably 2 to 20, or particularly preferably 2 to 10 carbon atoms, such as acetylamino or benzoylamino); an alkoxycarbonylamino group (having preferably 2 to 30, more preferably 2 to 20, or particularly preferably 2 to 12 carbon atoms, such as methoxycarbonylamino); an aryloxycarbonylamino group (having preferably 7 to 30, more preferably 7 to 20, or particularly preferably 7 to 12 carbon atoms, such as phenyloxycarbonylamino); a sulfonylamino group (having preferably 1 to 30, more preferably 1 to 20, or particularly preferably 1 to 12 carbon atoms, such as methanesulfonylamino or benzenesulfonylamino); a sulfamoyl group (having preferably 0 to 30, more preferably 0 to 20, or particularly preferably 0 to 12 carbon atoms, such as sulfamoyl, methylsulfamoyl, dimethylsulfamoyl, or phenylsulfamoyl); a carbamoyl group (having preferably 1 to 30, more preferably 1 to 20, or particularly preferably 1 to 12 carbon atoms, such as carbamoyl, methylcarbamoyl, diethylcarbamoyl, or phenylcarbamoyl); an alkylthio group (having preferably 1 to 30, more preferably 1 to 20, or particularly preferably 1 to 12 carbon atoms, such as methylthio group or ethylthio group); an arylthio group (having preferably 6 to 30, more preferably 6 to 20, or particularly preferably 6 to 12 carbon atoms, such as phenylthio); a heteroarylthio group (having preferably 1 to 30, more preferably 1 to 20, or particularly preferably 1 to 12 carbon atoms, such as pyridylthio, 2-benzoimizolylthio, benzoxazolylthio, or 2-benzthiazolylthio); a sulfonyl group (having preferably 1 to 30, more preferably 1 to 20, or particularly preferably 1 to 12 carbon atoms, such as mesyl or tosyl); a sulfinyl group (having preferably 1 to 30, more preferably 1 to 20, or particularly preferably 1 to 12 carbon atoms, such as methanesulfinyl or benzenesulfinyl); a ureido group (having preferably 1 to 30, more preferably 1 to 20, or particularly preferably 1 to 12 carbon atoms, such as ureido, methylureido, or phenylureido); a phosphoric amide group (having preferably 1 to 30, more preferably 1 to 20, or particularly preferably 1 to 12 carbon atoms, such as diethylphosphoric amide or phenylphosphoric amide); a hydroxy group; a mercapto group; a halogen atom (such as a fluorine atom, a chlorine atom, a bromine atom, or an iodine atom); a cyano group; a sulfo group; a carboxyl group; a nitro group; a hydroxamic group;

a sulfino group; a hydrazino group; an imino group; a heterocyclic group (having preferably 1 to 30, or more preferably 1 to 12 carbon atoms and containing, as a hetero atom, a nitrogen atom, an oxygen atom, or a sulfur atom, specifically imidazolyl, pyridyl, quinolyl, furyl, thienyl, piperidyl, morpholino, benzoxazolyl, benzimidazolyl, benzothiazolyl, carbazolyl, or azepinyl); and a silyl group (having preferably 3 to 40, more preferably 3 to 30, or particularly preferably 3 to 24 carbon atoms, such as trimethylsilyl or triphenylsilyl). Each of those substituents may be additionally substituted.

Examples of the fused ring aryl structure having 10 to 20 ring carbon atoms possessed by at least one of $Ar_{11}$, $Ar_{21}$, and $Ar_{31}$ in the general formula (2d), and substituents possessed by these aryl groups include a naphthalene structure, an anthracene structure, a phenanthrene structure, a pyrene structure, and a perylene structure. Of those, a naphthalene structure, an anthracene structure, a pyrene structure, or a phenanthrene structure is preferable, a phenanthrene structure or an aryl structure with four or more rings is more preferable, and a pyrene structure is particularly preferable.

Examples of the fused ring heteroaryl structure having 6 to 20 ring carbon atoms possessed by at least one of $Ar_{11}$, $Ar_{21}$, and $Ar_{31}$ in the general formula (2d), and substituents possessed by these aryl groups include a quinoline structure, a quinoxaline structure, a quinazoline structure, an acridine structure, a phenanthridine structure, a phthalazine structure, and a phenanthroline structure. Of those, a quinoline structure, a quinoxaline structure, a quinazoline structure, a phthalazine structure, or a phenanthroline structure is preferable.

The trivalent group derived from an aromatic ring represented by Ar in the general formula (2d) has preferably 6 to 30, more preferably 6 to 20, or still more preferably 6 to 16 carbon atoms. Specific examples of the trivalent group include trivalent groups each derived from benzene, naphthalene, anthracene, phenanthrene, pyrene, or triphenylene.

The trivalent group derived from a heterocyclic aromatic ring represented by Ar in the general formula (2d) contains, as a hetero atom, preferably an atom selected from a nitrogen atom, a sulfur atom, and an oxygen atom, or more preferably a nitrogen atom. In addition, the trivalent group has preferably 2 to 30, more preferably 3 to 20, or still more preferably 3 to 16 carbon atoms. Specific examples of the trivalent group include trivalent groups each derived from pyridine, pyrazine, thiopyran, quinoline, quinoxaline, or triazine. Each of those trivalent groups each derived from an aromatic ring or from a heterocyclic aromatic ring may have a substituent. Examples of the substituent include groups exemplified for a substituent on the aryl group represented by the substituent $Ar_{11}$. Ar preferably represents a benzenetolyl, naphthalenetolyl, anthracenetolyl, or pyrenetolyl group, or a trivalent group derived from triphenylene, more preferably represents a benzenetolyl group, or still more preferably represents an unsubstituted ($Ar_{11}$, $Ar_{21}$, and $Ar_{31}$ are each substituted) benzenetolyl group or an alkyl-substituted benzenetolyl group.

Specific examples of the benzene derivative represented by the general formula (2d) to be used in the organic EL device of the present invention include various known benzene derivatives such as a benzene derivative described in paragraphs [0079] to [0083] of Japanese Patent Application Laid-Open No. 2002-324678. Representative specific examples are shown below.

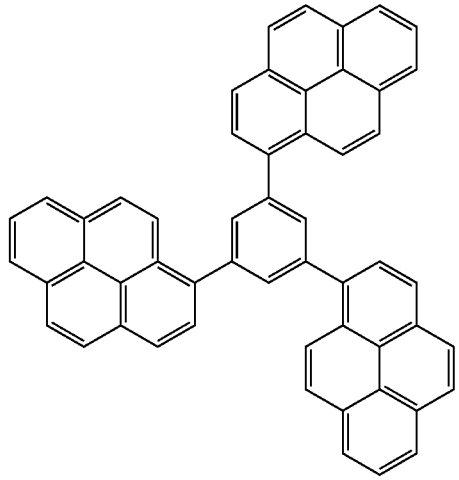

2d-1

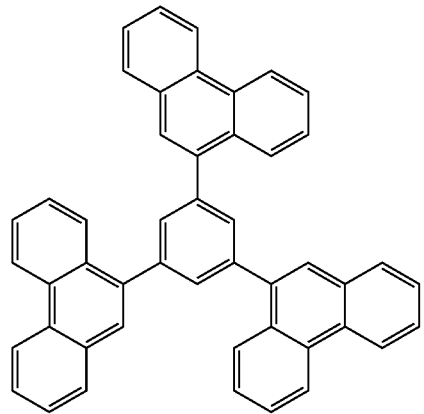

2d-2

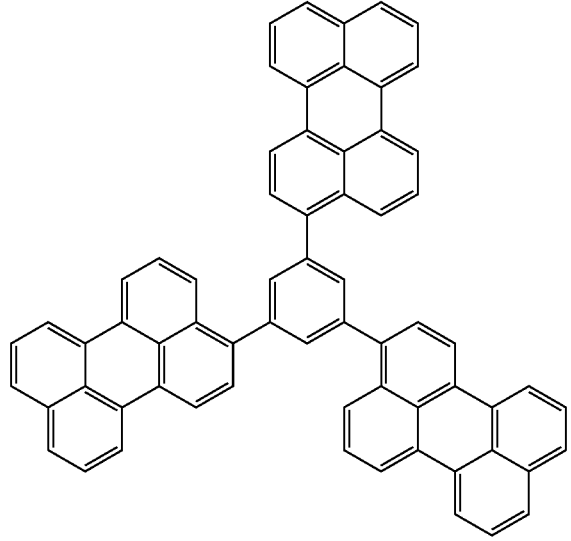

2d-3

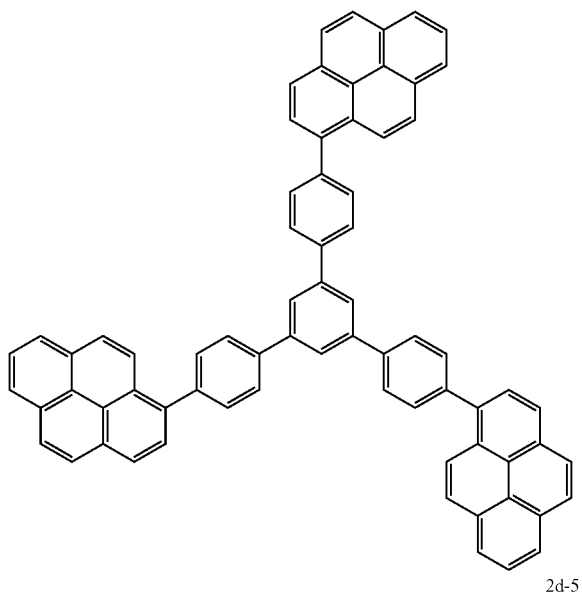
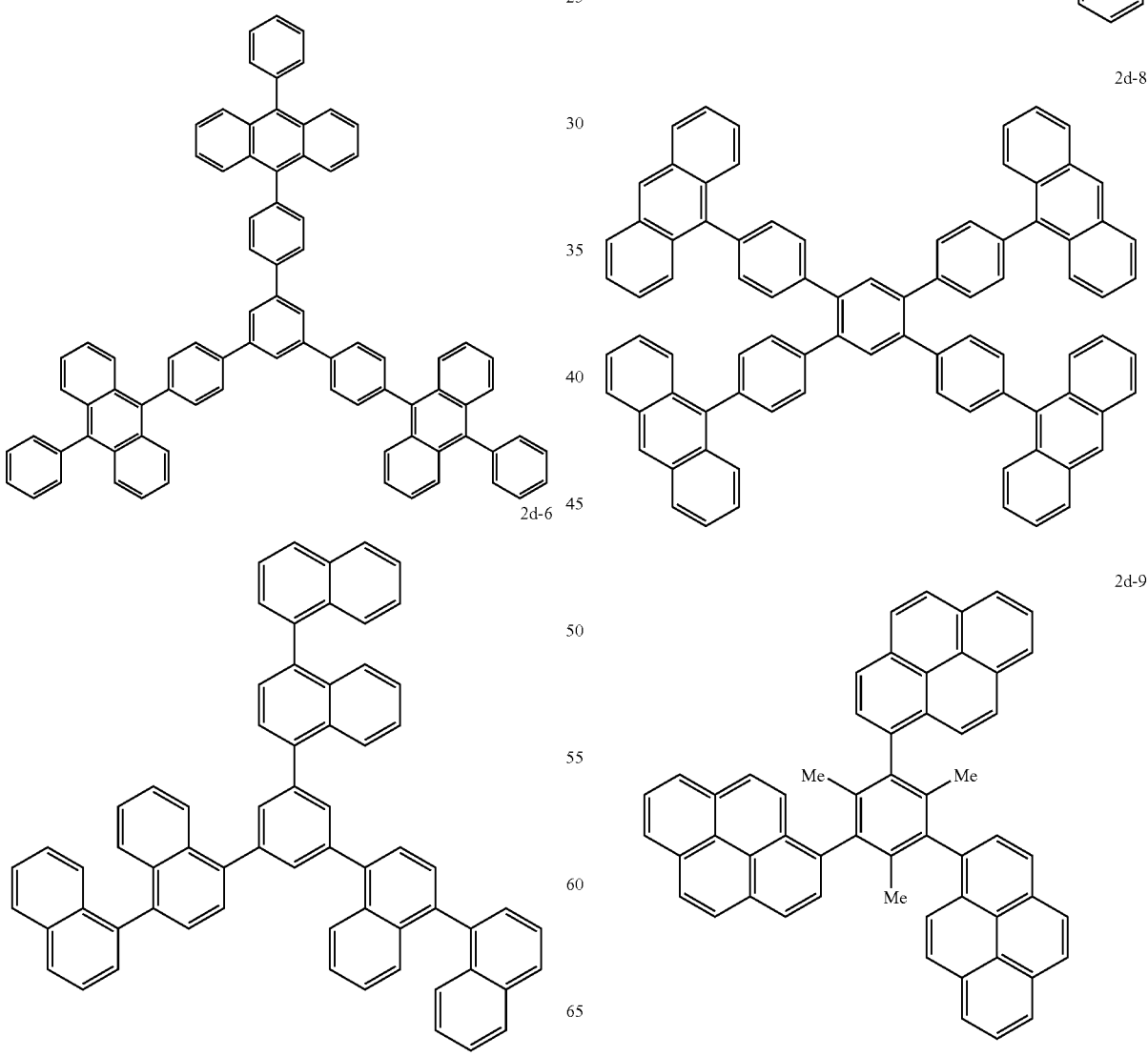

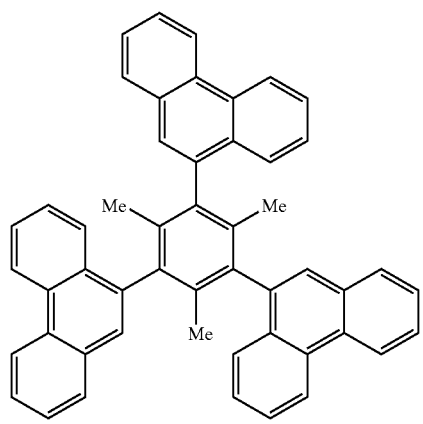
2d-10
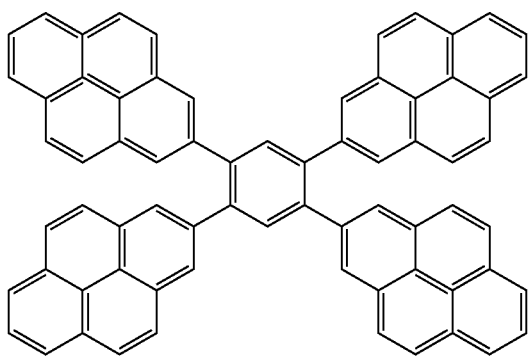
2d-13
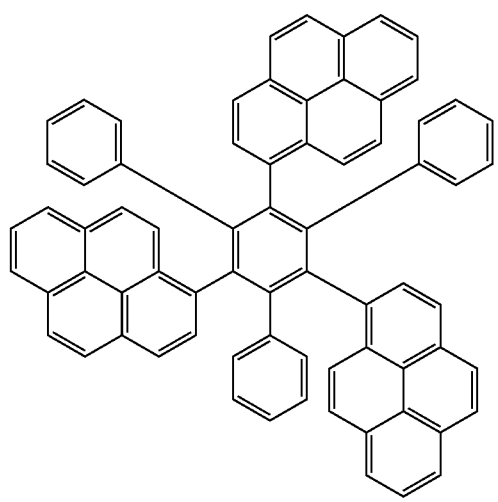
2d-11
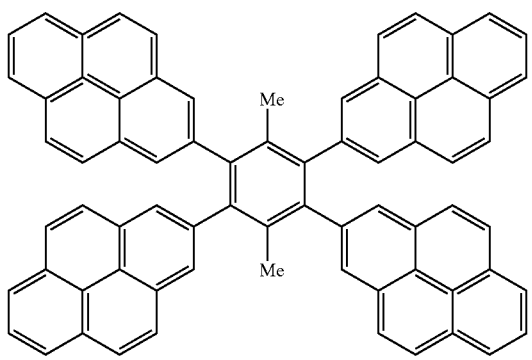
2d-14
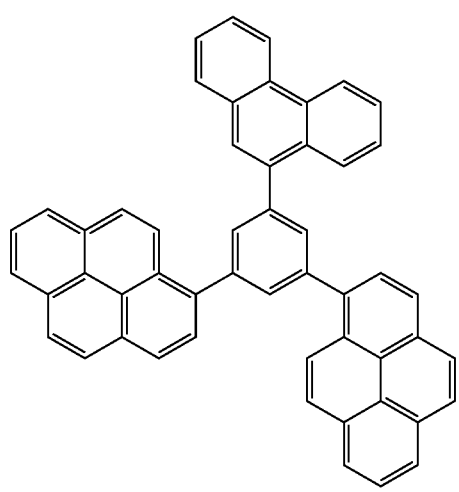
2d-12
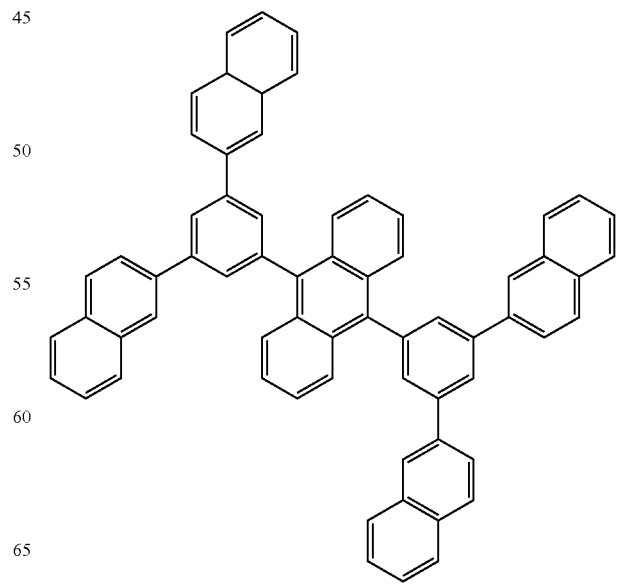
2d-15

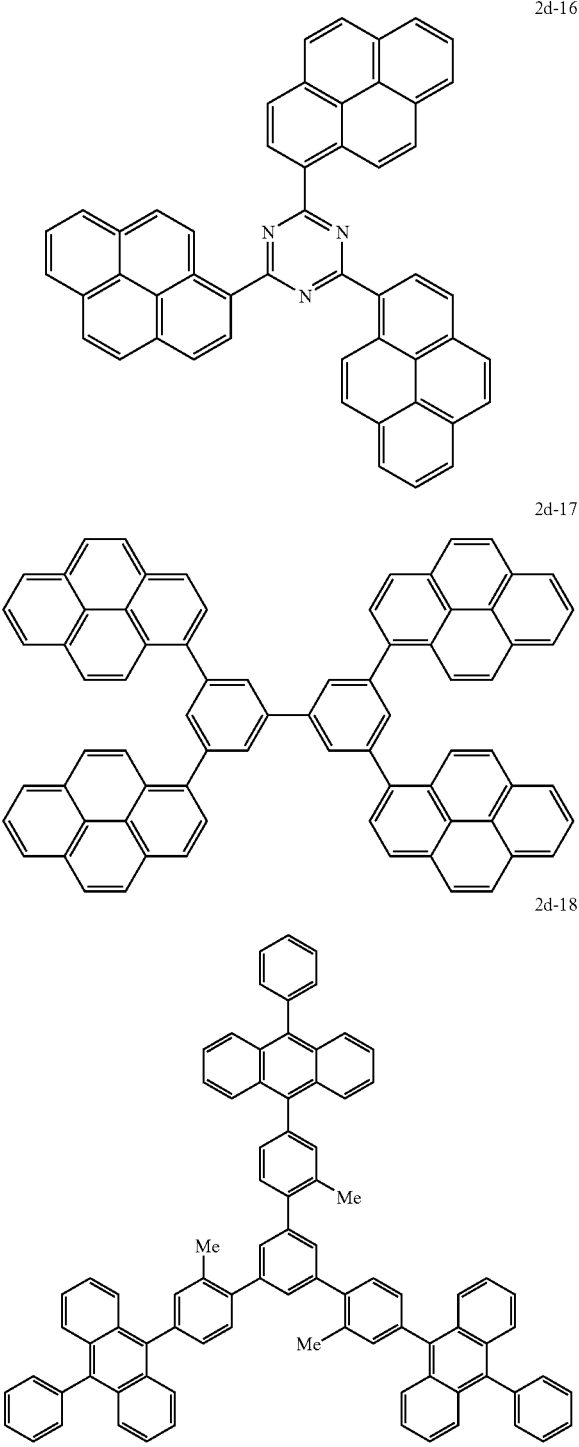

In the present invention, the organic EL device having multiple organic thin film layers is a laminate having, for example, an (anode/hole injecting layer/light emitting layer/cathode), (anode/light emitting layer/electron injecting layer/cathode), or (anode/hole injecting layer/light emitting layer/electron injecting layer/cathode) constitution.

In addition to the aromatic amine derivative of the present invention, an additional known light emitting material, doping material, hole injecting material, or electron injecting material can be used as required in the multiple layers. When the organic EL device has the multiple organic thin film layers, a reduction in luminance or lifetime due to quenching can be prevented. If needed, a light emitting material, a doping material, a hole injecting material, and an electron injecting material can be used in combination. In addition, a doping material can provide improvements in emission luminance and luminous efficiency, and red or blue light emission. In addition, each of the hole injecting layer, the light emitting layer, and the electron injecting layer may be formed of a layer constitution having two or more layers. At that time, in the case of the hole injecting layer, a layer for injecting a hole from the electrode is referred to as a hole injecting layer, and a layer for receiving the hole from the hole injecting layer and transporting the hole to the light emitting layer is referred to as a hole transporting layer. In the same manner, in the case of the electron injecting layer, a layer for injecting an electron from the electrode is referred to as an electron injecting layer, and a layer for receiving the electron from the electron injecting layer and transporting the electron to the light emitting layer is referred to as an electron transporting layer. Each of those layers is selected and used depending on factors such as the energy level of a material, heat resistance, and adhesiveness between the layer and an organic layer or a metal electrode.

Examples of a host material or a doping material other than those in the above general formulae (IV) to (VI) which can be used in the light emitting layer together with the aromatic amine derivative of the present invention include, but are not limited to: large amounts of fused aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracene)benzene and derivatives thereof; organic metal complexes such as tris(8-quinolinolato)aluminum or bis-(2-methyl-8-quinolinolato)-4-(phenylphenolinato)aluminum; a triarylamine derivative, a styrylamine derivative, a stilbene derivative, a coumarin derivative, a pyrane derivative, an oxazone derivative, a benzothiazole derivative, a benzoxazole derivative, a benzimidazole derivative, a pyrazine derivative, a cinnamate derivative, a diketopyrrolopyrrole derivative, an acridone derivative, and quinacridone derivative.

A compound having an ability of transporting a hole, having hole injection efficiency from an anode and excellent hole injection efficiency to a light emitting layer or a light emitting material, an ability of preventing the migration of an exciton generated in the light emitting layer to an electron injecting layer or an electron injecting material, and having excellent thin film-formability is preferable as a hole injecting material. Specific examples of the compound include, but not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, additional effective hole injecting materials are an aromatic tertiary amine derivative and a phthalocyanine derivative.

Examples of the aromatic tertiary amine derivative include, but not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, or N,N-bis(4-di-4-tolylaminophenyl)-4-phenyl-cyclohexane, or an oligomer or a polymer having those aromatic tertiary amine skeletons.

Examples of the phthalocyanine (Pc) derivative include, but not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc, and naphthalocyanine derivatives.

In addition, the organic EL device of the present invention is preferably formed of a layer containing each of those aromatic tertiary amine derivatives and/or each of phthalocyanine derivatives, for example, the hole transporting layer or the hole injecting layer between a light emitting layer and an anode.

A compound having an ability of transporting electrons, having electron injection efficiency from a cathode and excellent electron injection efficiency to a light emitting layer or a light emitting material, an ability of preventing the migration of an exciton generated in the light emitting layer to the hole injecting layer, and having excellent thin film-formability is preferable as an electron injecting material. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. In addition, an electron-accepting substance can be added to the hole injecting material or an electron-donating substance can be added to the electron injecting material to thereby intensify the hole injecting material or the electron injecting material, respectively.

In the organic EL device of the present invention, additional effective electron injecting materials are a metal complex compound and a nitrogen-containing five-membered ring derivative.

Examples of the metal complex compound include, but not limited to, 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium.

Examples of the preferred nitrogen-containing five-membered derivative include, an oxazole derivative, a thiazole derivative, an oxadiazole derivative, a thiadiazole derivative, and a triazole derivative. Specific examples of the derivative include, but not limited to, 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4'-biphenyl)-1,3,4-triazole, 2,5-bis(1-naphthyl)-1,3,4-triazole, and 1,4-bis[2-(5-phenyltriazolyl)]benzene.

In the organic EL device of the present invention, in addition to at least one kind of aromatic amine derivative selected from the general formulae (I), (II), and (III), at least one kind of a light emitting material, a doping material, a hole injecting material, and an electron injecting material may be incorporated into any one of the light emitting layers. In addition, the surface of the organic EL device obtained according to the present invention can be provided with a protective layer, or the entire device can be protected with silicone oil, a resin, or the like with a view to improving the stability of the device against temperature, humidity, an atmosphere, or the like.

A conductive material having a work function larger than 4 eV is suitably used in the anode of the organic EL device of the present invention. Examples of an available conductive material include, but not limited to: carbon, aluminum, vanadium, iron, cobalt, nickel, tungsten, silver, gold, platinum, and palladium, and alloys thereof; metal oxides such as tin oxide and indium oxide to be used in an ITO substrate and an NESA substrate; and organic conductive resins such as polythiophene and polypyrrole. A conductive substance having a work function smaller than 4 eV is suitably used in the cathode of the device. Examples of an available conductive substance include, but not limited to, magnesium, calcium, tin, lead, titanium, yttrium, lithium, ruthenium, manganese, aluminum, and lithium fluoride, and alloys thereof. Representative examples of the alloys include, but not limited to, a magnesium/silver alloy, a magnesium/indium alloy, and a lithium/aluminum alloy. A ratio between the components of an alloy is controlled depending on, for example, the temperature of a deposition source, an atmosphere, and the degree of vacuum, and is selected to be an appropriate ratio. Each of the anode and the cathode may be formed in a layer constitution having two or more layers if needed.

It is desirable that at least one surface of the organic EL device of the present invention is sufficiently transparent in the luminous wavelength region of the device so that the device can efficiently emit light. A substrate is also desirably transparent. A transparent electrode is formed by any one of the above conductive materials, and is set by a method such as deposition or sputtering in such a manner that desired translucency is secured. The light transmittance of an electrode on a light emitting surface is desirably 10% or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyetherimide, polyimide, and polypropylene.

Any one of: dry film forming methods such as vacuum deposition, sputtering, plasma, and ion plating; and wet film forming methods such as spin coating, dipping, and flow coating is applicable to the formation of each layer of the organic EL device according to the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, so sufficient emission luminance cannot be obtained even when an electric field is applied. In general, the thickness is in the range of preferably 5 nm to 10 µm, or more preferably 10 nm to 0.2 µm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used. In addition, an appropriate resin or additive may be used in each of the organic thin film layers for, for example, improving film formability or preventing a pin hole in the layer. Examples of an available resin include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. Examples of the additive include an antioxidant, a UV absorber, and a plasticizer.

The organic EL device of the present invention can find use in applications including: a flat luminous body such as the flat panel display of a wall hanging television; a light source for the backlight, meters, or the like of a copying machine, a printer, or a liquid crystal display; a display panel; and a signal lamp. In addition, the material of the present invention can be used in not only the field of an organic EL device but also the fields of an electrophotographic photosensitive member, a photoelectric conversion element, a solar cell, and an image sensor.

EXAMPLES

Synthesis Example 1 (D-2-2)

(1-1) Synthesis of 1,2-bis(4-bromo)ethene

In a stream of argon, 61.6 g (0.2 mol) of 4-bromo-benzylphosphonic acid diethyl ester, 37 g (0.2 mol) of 4-bromobenzaldehyde, 23.5 g (0.21 mol) of t-butoxypotassium, and 500 mL of THF were added to a 1-L three-necked flask provided with a cooling pipe, and the whole was stirred at room temperature for 8 hours. After the completion of the reaction, 500 mL of water were charged into the resultant, and the precipitated crystal was taken by filtration and washed with 500 mL of hexane, whereby 64 g of a white powder were obtained (in 95% yield).

(1-2) Synthesis of 1,2-bis(4-(4'-chlorophenyl)phenyl) ethene

In a stream of argon, 15 g (44.7 mmol) of 1,2-bis(4-bromo) ethene, 16.7 g (107 mmol) of 4-chlorophenylboronic acid, 2 g (1.8 mmol) of tetrakistriphenylphosphinepalladium, a 2-M solution prepared by dissolving 21.3 g (201 mmol) of sodium carbonate in 100 mL of water, and 100 mL of dimethoxyethane were added to a 1-L three-necked flask provided with a cooling pipe, and then the whole was stirred under heat at 110° C. for 8 hours. After the completion of the reaction, the precipitated crystal was taken by filtration, and was washed with 100 mL of water and 100 mL of methanol, whereby 16 g of a pale yellow powder were obtained (in 89% yield).

(1-3) Synthesis of D-2-2

In a stream of argon, 4 g (10 mmol) of 1,2-bis(4-(4'-chlorophenyl)phenyl)ethene, 5.4 g (25 mmol) of bis(2-naphthyl) amine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 6.1 g of a pale yellow powder were obtained. The powder was identified as Compound (D-2-2) (in 80% yield) by $^1$H-NMR spectroscopy and field desorption mass spectroscopy (FD-MS). It should be noted that the $^1$H-NMR spectrum of the compound was measured by using a DRX-500 (heavy methylene chloride solvent) manufactured by Brucker. The maximum absorption wavelength and maximum fluorescence wavelength of the resultant compound measured in a toluene solution were 389 nm and 445 nm, respectively.

Synthesis Example 2 (D-2-4)

In a stream of argon, 4 g (10 mmol) of) 1,2-bis(4-(4'-chlorophenyl)phenyl)ethene, 5.6 g (25 mmol) of bis(2,4-dimethylphenyl)amine, 0.03 g (1.5 mol %) of palladiumacetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 6.6 g of a pale yellow powder were obtained. The powder was identified as Compound (D-2-2) (in 85% yield) by $^1$H-NMR spectroscopy (FIG. 1) and FD-MS. It should be noted that the $^1$H-NMR spectrum of the compound was measured by using a DRX-500 (heavy methylene chloride solvent) manufactured by Brucker. The maximum absorption wavelength and maximum fluorescence wavelength of the resultant compound measured in a toluene solution were 383 nm and 441 nm, respectively.

Synthesis Example 3 (D-4-4)

Figure 2:
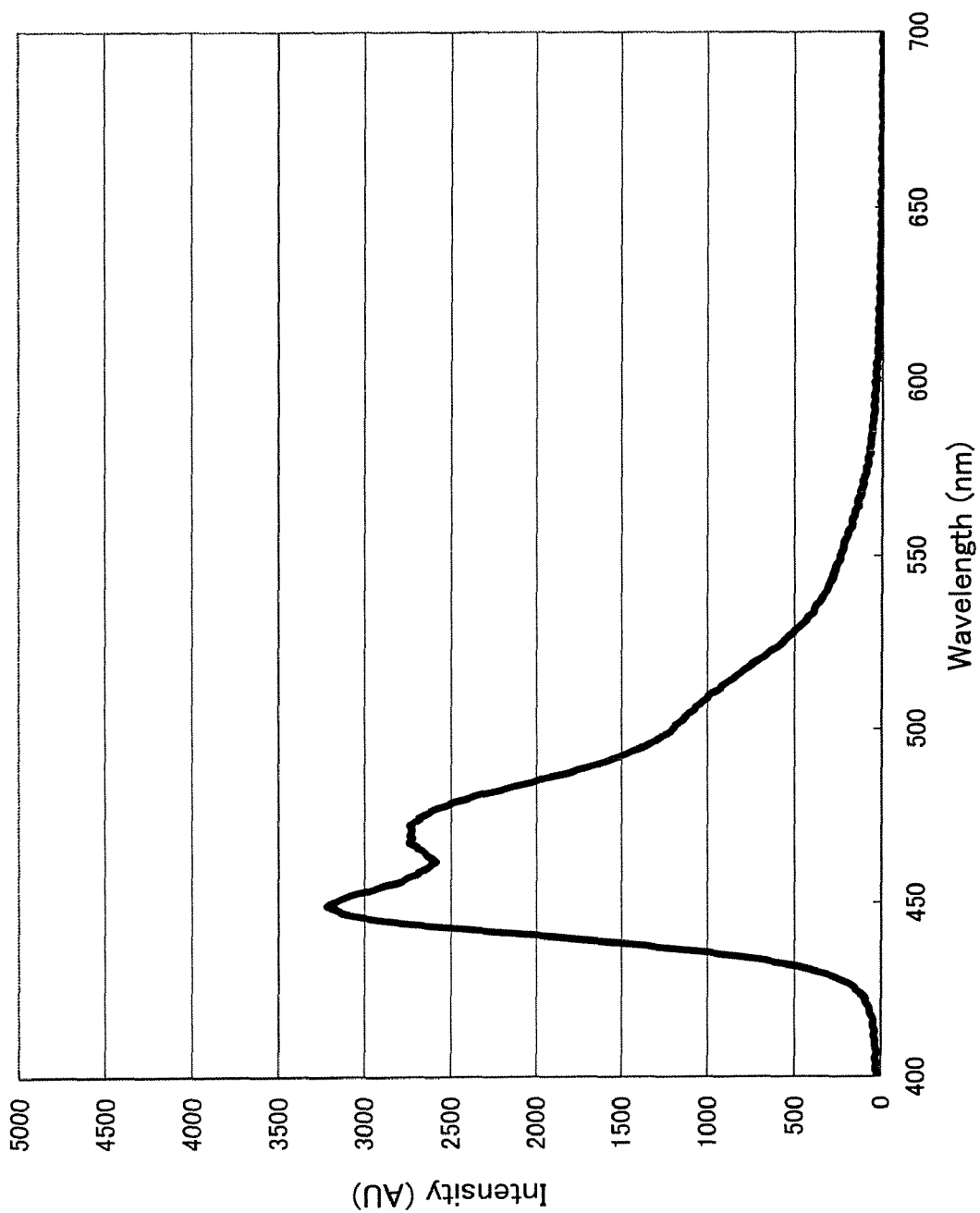
FIG. 2 is a view showing an emission spectrum of the aromatic amine derivative of the present invention obtained in Synthesis Example 2.

In a stream of argon, 4.1 g (10 mmol) of 4-bromo-4' (p-bromophenyl)-(E)-1,2-stilbene, 5.4 g (25 mmol) of bis(2-naphthyl)amine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 7.1 g of a pale yellow powder were obtained. The powder was identified as Compound (D-4-4) (in 90% yield) by FD-MS. The maximum absorption wavelength and maximum fluorescence wavelength of the resultant compound measured in a toluene solution were 397 nm and 446 nm, respectively. The emission spectrum is shown in FIG. 2.

Synthesis Example 4D-2-6

In a stream of argon, 4 g (10 mmol) of 1,2-bis(4-(4'-chlorophenyl)phenyl)ethene, 7.8 g (25 mmol) of bis(4-trimethylphenyl)amine, 0.03 g (1.5 mol %) of palladiumacetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 7.6 g of a pale yellow powder were obtained. The powder was identified as Compound (D-2-6) (in 80% yield) by $^1$H-NMR spectroscopy and FD-MS. The maximum absorption wavelength and maximum fluorescence wavelength of the resultant compound measured in a toluene solution were 381 nm and 439 nm, respectively.

Synthesis Example 5D-2-8

In a stream of argon, 4 g (10 mmol) of 1,2-bis(4-(4'-chlorophenyl)phenyl)ethene, 6.3 g (25 mmol) of 4-cyclohexyl diphenylamine, 0.03 g (1.5 mol %) of palladium acetate, 0.06 g (3 mol %) of tri-t-butylphosphine, 2.4 g (25 mmol) of t-butoxy sodium, and 100 mL of dry toluene were added to a 300-mL three-necked flask provided with a cooling pipe, and then the whole was stirred under heat at 100° C. overnight. After the completion of the reaction, the precipitated crystal was taken by filtration, and was washed with 50 mL of toluene and 100 mL of methanol, whereby 7.7 g of a pale yellow powder were obtained. The powder was identified as Compound (D-2-8) (in 93% yield) by $^1$H-NMR spectroscopy and FD-MS. The maximum absorption wavelength and maximum fluorescence wavelength of the resultant compound measured in a toluene solution were 384 nm and 443 nm, respectively.

Example 1

(1) Production of Organic EL Device

A transparent electrode composed of an indium tin oxide and having a thickness of 130 nm was provided on a glass substrate measuring 25 mm wide, 75 mm long, and 1.1 mm thick. The glass substrate was subjected to ultrasonic cleaning with isopropyl alcohol, and was then washed by being irradiated with ultraviolet light and ozone.

Next, the glass substrate provided with the transparent electrode was mounted on a substrate holder in the deposition tank of a vacuum deposition device, and the degree of vacuum in the vacuum tank was reduced to $1 \times 10^{-3}$ Pa.

First, N',N"-bis[4-(diphenylamino)phenyl]-N',N"-diphenylbiphenyl-4,4'-diamine was formed into a film having a thickness of 60 nm at a deposition rate of 2 nm/sec on the surface on the side where the transparent electrode was formed so as to cover the transparent electrode. The film functions as a hole injecting layer.

Next, N,N,N',N'-tetra(4-biphenylyl)benzidine was formed into a film having a thickness of 20 nm at a deposition rate of 2 nm/sec on the hole injecting layer. The film functions as a hole transporting layer.

Compound (2a'-55) [Light Emitting Material 1] and Compound (D-2-1) [Light Emitting Material 2] described above were simultaneously deposited from the vapor at a deposition rate of 2 nm/sec and a deposition rate of 0.2 nm/sec, respectively to form a film having a thickness of 40 nm and containing the compounds at a weight ratio (2a'-55):(D-2-1) of 40:2 on the hole transporting layer. The film functions as a light emitting layer.

Tris(8-hydroxyquinolino)aluminum was deposited from the vapor at a deposition rate of 2 nm/sec to form an electron transporting layer having a thickness of 20 nm on the resultant.

Further, lithium fluoride was formed into an electron injecting layer having a thickness of 1 nm at a deposition rate of 0.1 nm/sec.

Finally, aluminum was formed into a cathode layer having a thickness of 200 nm at a deposition rate of 2 nm/sec, whereby an organic EL device was produced.

(2) Evaluation of Organic EL Device

Next, the device was subjected to a current test. As a result, the device showed an emission luminance of 900 cd/m$^2$ at a voltage of 6.3 V. The emission peak wavelength (EL $\lambda_{max}$) and chromaticity of the device were measured. As a result, it was confirmed that the luminescent color of the device was blue. In addition, the device was driven at a constant current with its initial emission luminance set to 100 cd/m$^2$. As a result, the device had a half lifetime of 10,000 hours or longer. The result confirmed that the device was sufficient for practical use. Table 1 shows the obtained results.

Examples 2 to 5

Organic EL devices were each produced in the same manner as in Example 1 except that: Compounds (2a'-55) and (D-2-5) were used in Example 2 instead of Compounds (2a'-55) and (D-2-1) in Example 1, Compounds (2a'-55) and (D-4-4) were used in Example 3 instead of Compounds (2a'-55) and (D-2-1) in Example 1, Compounds (2a'-59) and (D-5-1) were used in Example 4 instead of Compounds (2a'-55) and (D-2-1) in Example 1, and Compounds (2a'-59) and (D-5-5) were used in Example 5 instead of Compounds (2a'-55) and (D-2-1) in Example 1.

Each of the organic EL devices was evaluated in the same manner as in Example 1. As a result, each of the devices was observed to emit blue light as shown in Table 1. Each of the devices showed an emission luminance of 750 to 900 cd/m$^2$, and had a half lifetime of 10,000 hours or longer. The result confirmed that the devices were sufficient for practical use.

Examples 6 to 9

Organic EL devices were each produced in the same manner as in Example 1 except that: Compounds (2a-7) and (D-5-6) were used in Example 6 instead of Compounds (2a'-55) and (D-2-1) in Example 1, Compounds (2b-8) and (1-13) were used in Example 7 instead of Compounds (2a'-55) and (D-2-1) in Example 1, Compounds (2a-17) and (D-1-4) were used in Example 8 instead of Compounds (2a'-55) and (D-2-1) in Example 1, and Compounds (2a-33) and (D-5-3) were used in Example 9 instead of Compounds (2a'-55) and (D-2-1) in Example 1.

[Table 1]

TABLE 1-1

| | Example 1 | Example 2 | Example 3 | Example 4 | Example 5 |
|---|---|---|---|---|---|
| Light Emitting Material 1 | 2a'-55 | 2a'-55 | 2a'-55 | 2a'-59 | 2a'-59 |
| Light Emitting Material 2 | D-2-1 | D-2-5 | D-4-4 | D-5-1 | D-5-5 |
| Voltage at which device is driven (V) | 6.3 | 6.3 | 6.3 | 6.3 | 6.3 |
| EL $\lambda_{max}$ | 465 | 463 | 455 | 459 | 460 |
| Emission luminance (cd/m$^2$) | 900 | 890 | 750 | 790 | 800 |
| Half lifetime (hr) | >10,000 | >10,000 | >10,000 | >10,000 | >10,000 |

[Table 2]

TABLE 1-2

| | Example 6 | Example 7 | Example 8 | Example 9 | Comparative Example 1 | Comparative Example 2 |
|---|---|---|---|---|---|---|
| Light Emitting Material 1 | 2a-7 | 2b-9 | 2a-17 | 2a-33 | 2a'-59 | 2a'-59 |
| Light Emitting Material 2 | D-4-8 | D-5-6 | D-1-4 | D-5-3 | Compound A | Compound B |
| Voltage at which device is driven (V) | 6.3 | 6.3 | 6.3 | 6.5 | 6.3 | 6.3 |
| EL λmax (nm) | 450 | 469 | 460 | 451 | 444 | 455 |
| Emission luminance (cd/m$^2$) | 550 | 790 | 700 | 600 | 300 | 600 |
| Half lifetime (hr) | 9,000 | 7,500 | 8,000 | 7,000 | 3,000 | 4,500 |

Comparative Example 1

An organic EL device was produced in the same manner as in Example 1 except that Compound (A) shown below was used in Comparative Example 1 instead of Compound (1-3) in Example 1.

The organic EL device was evaluated in the same manner as in Example 1. As a result, the device was observed to emit blue light as shown in Table 1-2. However, the device showed an emission luminance of 300 cd/m$^2$. This means that the device had low current efficiency. In addition, the device had a short half lifetime, specifically, 3,000 hours or shorter.

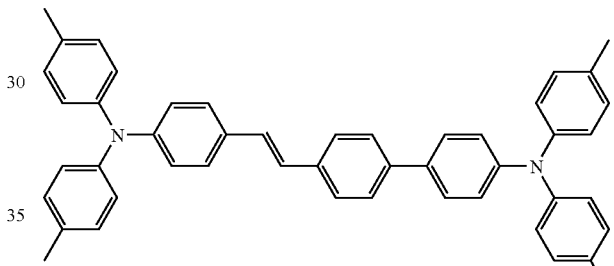

Compound B

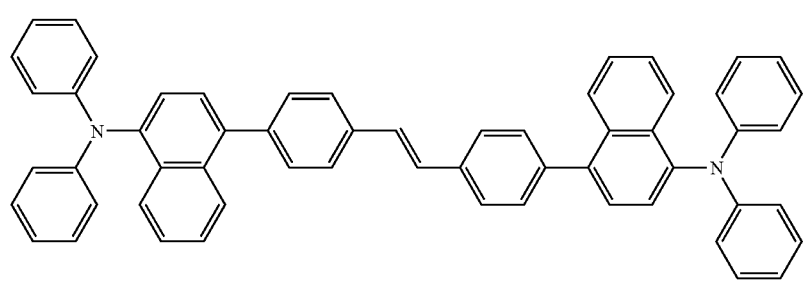

Compound A

Comparative Example 2

An organic EL device was produced in the same manner as in Example 1 except that Compound (B) shown below was used in Comparative Example 2 instead of Compound (1-3) in Example 1.

The organic EL device was evaluated in the same manner as in Example 1. As a result, the device was observed to emit blue light as shown in Table 1-2. However, the device had a short half lifetime, specifically, 4,500 hours or shorter.

Example 10

(1) Production of Organic EL Device

A transparent electrode composed of an indium tin oxide and having a thickness of 130 nm was provided on a glass substrate measuring 25 mm wide, 75 mm long, and 1.1 mm thick. The glass substrate was subjected to ultrasonic cleaning with isopropyl alcohol, and was then washed by being irradiated with ultraviolet light and ozone.

Next, the glass substrate provided with the transparent electrode was mounted on a substrate holder in the deposition tank of a vacuum deposition device, and the degree of vacuum in the vacuum tank was reduced to $1 \times 10^{-3}$ Pa.

First, N',N'''-bis[4-(diphenylamino)phenyl]-N',N'''-diphenylbiphenyl-4,4'-diamine was formed into a film having a thickness of 60 nm at a deposition rate of 2 nm/sec on the surface on the side where the transparent electrode was formed so as to cover the transparent electrode. The film functions as a hole injecting layer.

Next, N,N,N',N'-tetra(4-biphenylyl)benzidine was formed into a film having a thickness of 20 nm at a deposition rate of 2 nm/sec on the hole injecting layer. The film functions as a hole transporting layer.

Compound (2a-31) [Light Emitting Material 1] and Compound (D-2-6) [Light Emitting Material 2] described above were simultaneously deposited from the vapor at a deposition rate of 1 nm/sec and a deposition rate of 0.2 nm/sec, respectively, to form a film having a thickness of 40 nm and containing the compounds at a weight ratio (2a-31):(D-2-6) of 40:2 on the hole transporting layer. The film functions as a light emitting layer.

Tris(8-hydroxyquinolino)aluminum was deposited from the vapor at a deposition rate of 2 nm/sec to form an electron transporting layer having a thickness of 20 nm on the resultant.

Further, lithium fluoride was formed into an electron injecting layer having a thickness of 1 nm at a deposition rate of 0.1 nm/sec.

Finally, aluminum was formed into a cathode layer having a thickness of 200 nm at a deposition rate of 2 nm/sec, whereby an organic EL device was produced.

(2) Evaluation of Organic EL Device

Next, the device was subjected to a current test. As a result, the device showed an emission luminance of 600 cd/m² at a voltage of 6.3 V. The emission peak wavelength (EL $\lambda_{max}$) and chromaticity of the device were measured. As a result, it was confirmed that the luminescent color of the device was blue. In addition, the device was driven at a constant current with its initial emission luminance set to 100 cd/m². As a result, the device had a half lifetime of 9,000 hours.

Examples 11 and 12

Organic EL devices were each produced in the same manner as in Example 8 except that: a compound ratio (2a-31):(D-2-6) was set to 40:3 in Example 11 instead of a compound ratio (2a-31):(D-2-6)=40:2 in Example 10, and a compound ratio (2a-31):(D-2-6) was set to 40:4 in Example 12 instead of a compound ratio (2a-31) (D-2-6)=40:2 in Example 10.

Each of the organic EL devices was evaluated in the same manner as in Example 10. As a result, each of the devices was observed to emit blue light. The device of Example 11 showed an emission luminance of 620 cd/m², and the device of Example 12 showed an emission luminance of 625 cd/m². Both the devices had a half lifetime of 10,000 hours or longer. The foregoing result confirmed that a device containing 5 to 10 wt % of the aromatic amine derivative of the present invention in its light emitting layer had sufficiently high practical performance.

INDUSTRIAL APPLICABILITY

As described above in detail, the organic EL device using the aromatic amine derivative of the present invention provides emission luminance sufficient for practical use even at a low applied voltage, has high luminous efficiency, hardly deteriorates even after long-term use, and has a long lifetime. Therefore, the organic EL device is useful as a light source such as a flat luminous body of a wall television or a backlight for a display.

The invention claimed is:

1. An aromatic amine represented by the formula (IV):

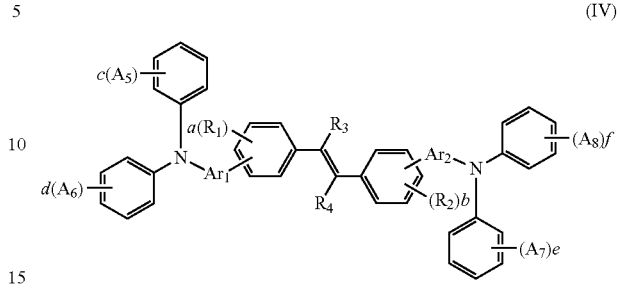

(IV)

wherein:
$R_1$ and $R_2$ each independently represent:
a substituted or unsubstituted alkyl group having 1 to 50 carbon atoms,
a substituted or unsubstituted aryl group having 5 to 50 carbon atoms,
a substituted or unsubstituted aralkyl group having 1 to 50 carbon atoms,
a substituted or unsubstituted cycloalkyl group having 5 to 50 carbon atoms,
a substituted or unsubstituted alkoxyl group having 1 to 50 carbon atoms,
a substituted or unsubstituted aryloxy group having 5 to 50 carbon atoms,
a substituted or unsubstituted arylamino group having 5 to 50 carbon atoms,
a substituted or unsubstituted alkylamino group having 1 to 20 carbon atoms,
a substituted or unsubstituted silyl group having 1 to 20 carbon atoms, or
a substituted or unsubstituted heterocyclic group having 5 to 50 carbon atoms;
a and b each independently represent an integer of 0 to 4, wherein when a represents 2 or more, multiple $R_1$s may be identical to or different from each other, and when b represents 2 or more, multiple $R_2$s may be identical to or different from each other;
$R_3$ and $R_4$ each independently represent:
a hydrogen atom,
a substituted or unsubstituted alkyl group having 1 to 50 carbon atoms,
a substituted or unsubstituted aryl group having 5 to 50 carbon atoms,
a substituted or unsubstituted aralkyl group having 1 to 50 carbon atoms,
a substituted or unsubstituted cycloalkyl group having 5 to 50 carbon atoms,
a substituted or unsubstituted alkoxyl group having 1 to 50 carbon atoms,
a substituted or unsubstituted aryloxy group having 5 to 50 carbon atoms,
a substituted or unsubstituted arylamino group having 5 to 50 carbon atoms,
a substituted or unsubstituted alkylamino group having 1 to 20 carbon atoms,
a substituted or unsubstituted silyl group having 1 to 20 carbon atoms, or
a substituted or unsubstituted heterocyclic group having 5 to 50 carbon atoms;

Ar₁ represents:
  a substituted or unsubstituted aryl group having 5 to 50 carbon atoms, or
  a substituted or unsubstituted heterocyclic group having 5 to 50 carbon atoms;
Ar₂ represents:
  a substituted or unsubstituted aryl group having 5 to 50 carbon atoms, or
  a substituted or unsubstituted heterocyclic group having 5 to 50 carbon atoms;
$A_5$ to $A_8$ each independently represent:
  a hydrogen atom,
  a substituted or unsubstituted alkyl group having 1 to 50 carbon atoms,
  a substituted or unsubstituted aryl group having 5 to 50 carbon atoms,
  a substituted or unsubstituted aralkyl group having 1 to 50 carbon atoms,
  a substituted or unsubstituted cycloalkyl group having 3 to 50 carbon atoms,
  a substituted or unsubstituted alkoxyl group having 1 to 50 carbon atoms,
  a substituted or unsubstituted aryloxy group having 5 to 50 carbon atoms,
  a substituted or unsubstituted arylamino group having 5 to 50 carbon atoms,
  a substituted or unsubstituted alkylamino group having 1 to 20 carbon atoms,
  a substituted or unsubstituted silyl group having 1 to 20 carbon atoms, or
  a substituted or unsubstituted heterocyclic group having 5 to 50 carbon atoms; and
c, d, e, and f each independently represent an integer of 0 to 5, wherein when any one of c, d, e, and f represents 2 or more, corresponding multiple $A_5$s, $A_6$s, $A_7$s, or $A_8$s may be identical to or different from each other, or may be coupled with each other to form a saturated or unsaturated ring, and $A_5$ and $A_6$, or $A_7$ and $A_8$ may be coupled with each other to form a saturated or unsaturated ring,
provided that at least one of $A_5$ and $A_6$, and at least one of $A_7$ and $A_8$ each represent a substituted or unsubstituted silyl group having 1 to 20 carbon atoms.

2. An organic electroluminescence device, comprising
an organic thin film layer comprising one or more layers comprising at least a light emitting layer and interposed between a cathode and an anode,
wherein at least one layer of the organic thin film layer comprises the aromatic amine according to claim 1 alone or as a component of a mixture.

3. An organic electroluminescence device, comprising an organic thin film layer comprising one or more layers comprising at least a light emitting layer and interposed between a cathode and an anode,
wherein the light emitting layer comprises the aromatic amine according to claim 1 alone or as a component of a mixture.

4. The organic electroluminescence device according to claim 2 or 3, wherein the light emitting layer comprises the aromatic amine and a compound having a structure having an anthracene central skeleton and represented by the formula (2a):

(2a)

wherein: $A_1$ and $A_2$ each independently represent a substituted or unsubstituted aromatic ring having 6 to 20 ring carbon atoms;
the aromatic ring may, optionally, be substituted by at least one substituent;
the at least one substituent is selected from:
  a substituted or unsubstituted aryl group having 6 to 50 ring carbon atoms,
  a substituted or unsubstituted alkyl group having 1 to 50 carbon atoms,
  a substituted or unsubstituted cycloalkyl group having 3 to 50 carbon atoms,
  a substituted or unsubstituted alkoxy group having 1 to 50 carbon atoms,
  a substituted or unsubstituted aralkyl group having 6 to 50 carbon atoms,
  a substituted or unsubstituted aryloxy group having 5 to 50 ring atoms,
  a substituted or unsubstituted arylthio group having 5 to 50 ring atoms,
  a substituted or unsubstituted alkoxycarbonyl group having 1 to 50 carbon atoms,
  a substituted or unsubstituted silyl group,
  a carboxyl group,
  a halogen atom,
  a cyano group,
  a nitro group,
  a hydroxyl group,
  and combinations thereof;
wherein, when the aromatic ring is substituted by two or more substituents, the substituents may be identical to or different from each other, and adjacent substituents may be bonded to each other to form a saturated or unsaturated cyclic structure; and
$R_1$ to $R_8$ are each independently selected from:
  a hydrogen atom,
  a substituted or unsubstituted aryl group having 6 to 50 ring carbon atoms,
  a substituted or unsubstituted heteroaryl group having 5 to 50 ring atoms,
  a substituted or unsubstituted alkyl group having 1 to 50 carbon atoms,
  a substituted or unsubstituted cycloalkyl group having 3 to 50 carbon atoms,
  a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group.

5. The organic electroluminescence device according to claim 4, wherein, in the formula (2a), $A_1$ and $A_2$ represent different groups.

6. The organic electroluminescence device according to claim 2 or 3, wherein the light emitting layer comprises the aromatic amine and a compound having a structure having a pyrene central skeleton and represented by the formula (2b):

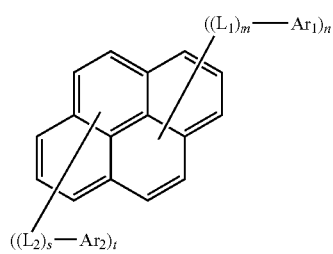

(2b)

wherein:

$Ar_1$ and $Ar_2$ each independently represent a substituted or unsubstituted aryl group having 6 to 50 ring carbon atoms;

$L_1$ and $L_2$ are each independently selected from:

a substituted or unsubstituted phenylene group, a substituted or unsubstituted naphthalenylene group, a substituted or unsubstituted fluorenylene group, or a substituted or unsubstituted dibenzosilolylene group;

m represents an integer of 0 to 2, n represents an integer of 1 to 4, s represents an integer of 0 to 2, t represents an integer of 0 to 4; and $L_1$ or $Ar_1$ is bonded to any one of 1- to 5-positions of pyrene, and $L_2$ or $Ar_2$ is bonded to any one of 6- to 10-positions of pyrene.

7. The organic electroluminescence device according to claim 2 or 3, wherein the light emitting layer comprises the aromatic amine and a compound having a structure having a triphenylamine skeleton and represented by the formula (2c):

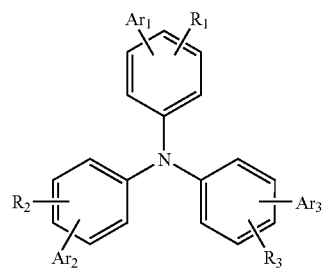

(2c)

wherein:

$Ar_1$, $Ar_2$, and $Ar_3$ are each independently selected from a group having an anthracene structure, a group having a phenanthrene structure, and a group having a pyrene structure; and $R_1$, $R_2$, and $R_3$ each independently represent a hydrogen atom or a substituent.

8. The organic electroluminescence device according to claim 2 or 3, wherein the light emitting layer comprises the aromatic amine and a compound having a structure represented by the formula (2d):

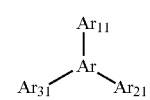

(2d)

wherein:

$Ar_{11}$, $Ar_{21}$, and $Ar_{31}$ each independently represent an aryl group having 6 to 50 ring carbon atoms;

the aryl group may optionally be substituted by at least one substituent;

at least one of $Ar_{11}$, $Ar_{21}$, $Ar_{31}$, and, optionally substituents possessed by these aryl groups, has a fused ring aryl structure having 10 to 20 ring carbon atoms, or a fused ring heteroaryl structure having 6 to 20 ring carbon atoms; and Ar represents a trivalent group from an aromatic ring or from a heterocyclic aromatic ring.

9. An organic electroluminescence material-containing solution, comprising:

organic electroluminescence materials comprising the aromatic amine according to claim 1; and a solvent.

10. An organic electroluminescence material-comprising solution comprising organic electroluminescence materials and a solvent, wherein:

the organic electroluminescence materials comprise a host material and a dopant material; and the dopant material comprises the aromatic amine according to claim 1.

11. The aromatic amine of claim 1, wherein $Ar_2$ represents the substituted or unsubstituted aryl group having 5 to 50 bonds.

12. The aromatic amine of claim 1, wherein $Ar_2$ represents the substituted or unsubstituted heterocyclic group having 5 to 50 carbons.

13. The aromatic amine of claim 1, wherein $Ar_1$ represents the substituted or unsubstituted aryl group having 5 to 50 carbon atoms.

14. An aromatic amine, which is a compound selected from
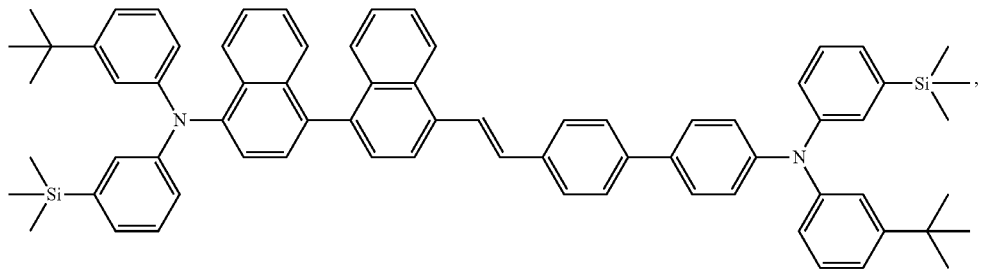
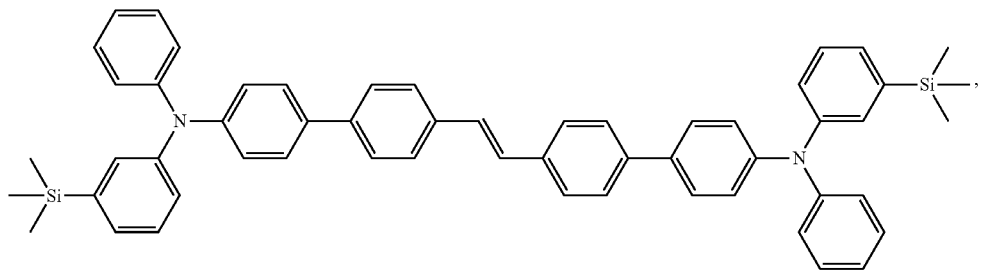
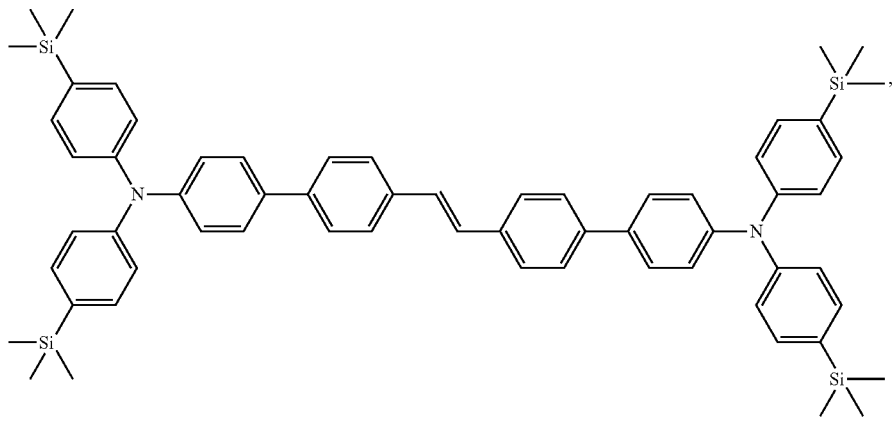
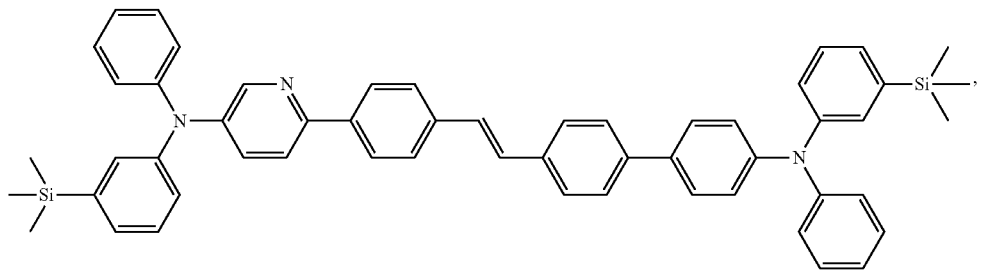
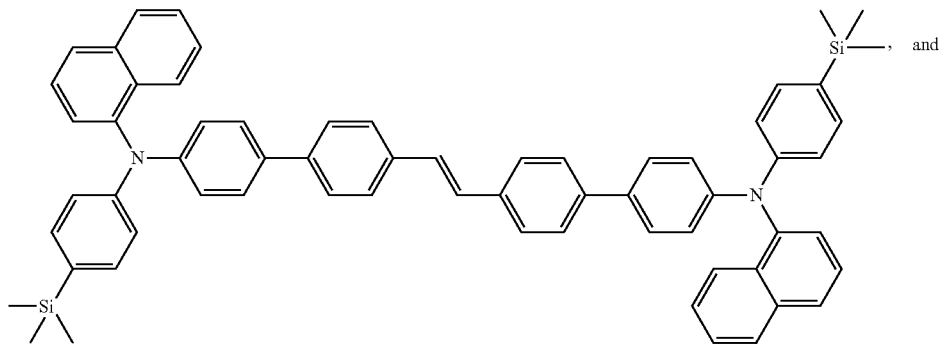

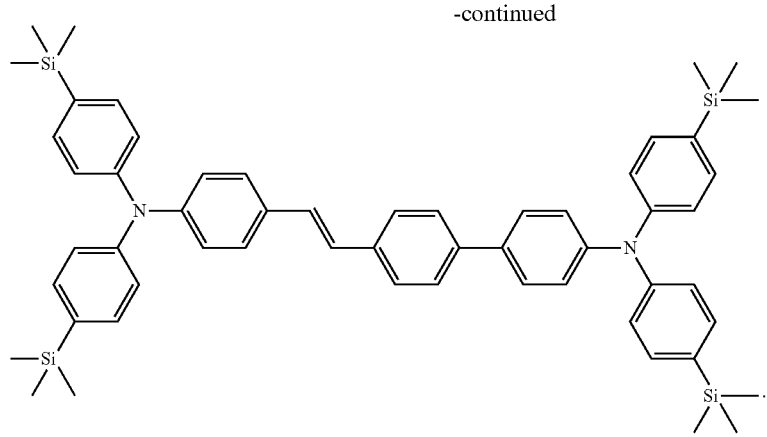
15. The aromatic amine of claim 1, comprising a group selected from a trimethylsilyl group, a triphenylsilyl group, triethylsilyl group, a tripropylsilyl group, a butyldimethylsilyl group, a propyldimethylsilyl group, a vinyldimethylsilyl group, and a t-butyldimethylsilyl group.
* * * * *